United States Patent
Hwang et al.

(10) Patent No.: US 10,369,149 B2
(45) Date of Patent: Aug. 6, 2019

(54) 4-(2-AMINO-TETRAHYDRONA-PHTHALENYL)PYRIMIDINE DERIVATIVE, PREPARATION METHOD THEREFOR, AND PHARMACEUTICAL COMPOSITION FOR PREVENTING OR TREATING CANCER, CONTAINING SAME AS ACTIVE INGREDIENT

(71) Applicant: KOREA RESEARCH INSTITUTE OF CHEMICAL TECHNOLOGY, Daejeon (KR)

(72) Inventors: Jong Yeon Hwang, Jeollabuk-do (KR); Hyoung Rae Kim, Daejeon (KR); Jae Du Ha, Daejeon (KR); Sung Yun Cho, Daejeon (KR); Hee Jung Jung, Daejeon (KR); Pilho Kim, Daejeon (KR); Chang Soo Yun, Daejeon (KR); Chong Ock Lee, Daejeon (KR); Chi Hoon Park, Daejeon (KR); Chong Hak Chae, Daejeon (KR); Sunjoo Ahn, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 26 days.

(21) Appl. No.: 15/567,224

(22) PCT Filed: Dec. 30, 2015

(86) PCT No.: PCT/KR2015/014482
§ 371 (c)(1),
(2) Date: Oct. 17, 2017

(87) PCT Pub. No.: WO2016/171372
PCT Pub. Date: Oct. 27, 2016

(65) Prior Publication Data
US 2018/0104242 A1    Apr. 19, 2018

(30) Foreign Application Priority Data
Apr. 22, 2015  (KR) .................. 10-2015-0056322

(51) Int. Cl.
| *A61K 31/506* | (2006.01) |
| *C07D 239/30* | (2006.01) |
| *C07D 239/48* | (2006.01) |
| *A23L 33/10* | (2016.01) |
| *A61P 35/00* | (2006.01) |
| *C07B 43/04* | (2006.01) |
| *C07C 13/48* | (2006.01) |

(52) U.S. Cl.
CPC .......... *A61K 31/506* (2013.01); *A23L 33/10* (2016.08); *A61P 35/00* (2018.01); *C07B 43/04* (2013.01); *C07C 13/48* (2013.01); *C07D 239/30* (2013.01); *C07D 239/48* (2013.01); *C07B 2200/07* (2013.01)

(58) Field of Classification Search
CPC .................................................... A61K 31/506
See application file for complete search history.

(56) References Cited

U.S. PATENT DOCUMENTS

2011/0190259 A1   8/2011  Michellys

FOREIGN PATENT DOCUMENTS

| WO | 2004080980 A1 | 9/2004 | |
| WO | 2008051547 A1 | 5/2008 | |
| WO | WO-2008051547 A1 * | 5/2008 | .......... C07D 239/48 |
| WO | 2009143389 A1 | 11/2009 | |
| WO | 2015038868 A1 | 3/2015 | |
| WO | WO-2015038868 A1 * | 3/2015 | .......... C07D 403/12 |

OTHER PUBLICATIONS

Grande, E., et al. "Targeting Oncogenic ALK". Molecular Cancer Therapeutics. (Apr. 2011), vol. 10, Issue 4, pp. 569-579. (Year: 2011).*
Navigating Cancer. "List of Cancer Chemotherapy Drugs." (2013). Accessed Nov. 26, 2013. Available from: < https://www.navigatingcancer.com/library/all/chemotherapy_drugs >. (Year: 2013).*
Grundt et al., "Identification of a New Scaffold for Opioid Receptor Antagonism Based on the 2-Amino-1,1-dimethyl-7-hydroxytetralin Pharmacophore", J. Med. Chem., 2004, vol. 47, No. 21, pp. 5069-5075.
Liu et al., "Design, synthesis and pharmacological evaluation of 2-(thiazol-2-amino)-4-arylaminopyrimidines as potent anaplastic lymphoma kinase (ALK) inhibitors" European Journal of Medicinal Chemistry, 2014, vol. 86, pp. 438-448.
Liu et al., "Novel 2,4-Diarylaminopyrimidine Analogues (DAAPalogues) Showing Potent c-Met/ALK Multikinase Inhibitory Activities" ACS Medicinal Chemisty Letters, 2014, vol. 5, No. 4, pp. 304-308.

(Continued)

*Primary Examiner* — Noble E Jarrell
*Assistant Examiner* — John S Kenyon
(74) *Attorney, Agent, or Firm* — Lucas & Mercanti, LLP

(57) ABSTRACT

The present invention relates to a 4-(2-amino-tetrahydronaphthaleneyl)pyrimidine derivative, a preparation method thereof, and a pharmaceutical composition for the prevention or treatment of cancer comprising the same as an active ingredient. The 4-(2-amino-tetrahydronaphthaleneyl) pyrimidine derivative, the optical isomer thereof, or the pharmaceutically acceptable salt thereof of the present invention is very effective in suppressing anaplastic lymphoma kinase (ALK) activity and as a result it can improve the effectiveness of treatment on cancer cells having anaplastic lymphoma kinase (ALK) fusion proteins such as EML4-ALK and NPM-ALK, so that it can be effectively used as a pharmaceutical composition for preventing or treating cancer.

9 Claims, 2 Drawing Sheets

(56) References Cited

OTHER PUBLICATIONS

International Search Report and Written Opinion for International Application No. PCT/KR2015/014482 (17 Pages) (dated Apr. 22, 2016).

* cited by examiner

[Figure 1]
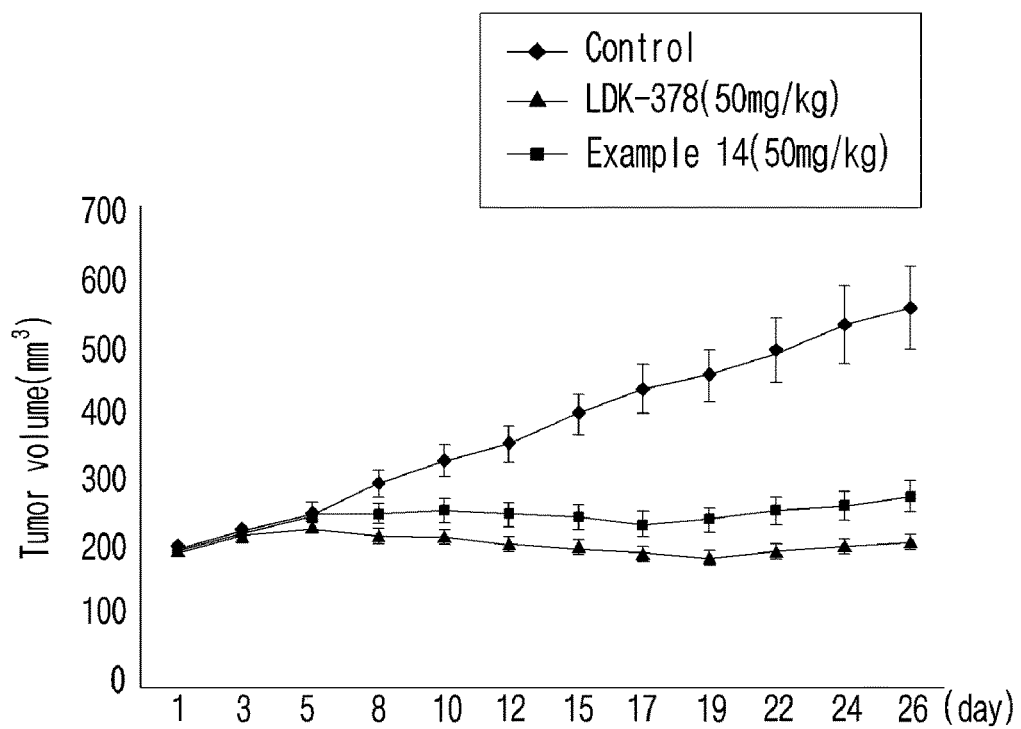

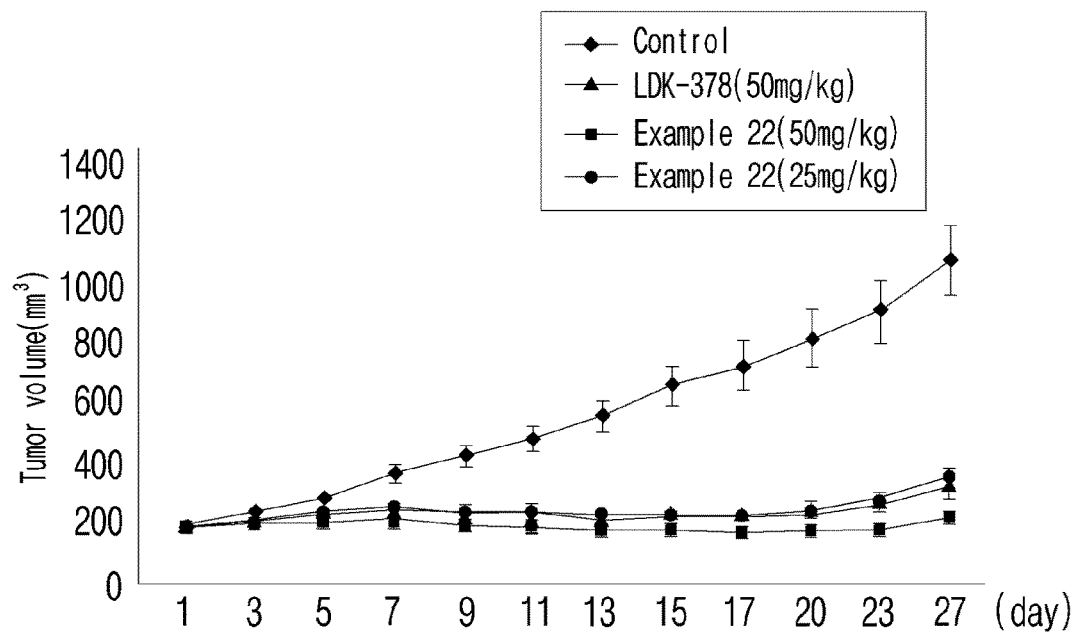
[Figure 2]

4-(2-AMINO-TETRAHYDRONA-PHTHALENYL)PYRIMIDINE DERIVATIVE, PREPARATION METHOD THEREFOR, AND PHARMACEUTICAL COMPOSITION FOR PREVENTING OR TREATING CANCER, CONTAINING SAME AS ACTIVE INGREDIENT

CROSS-REFERENCE TO RELATED APPLICATIONS

This application is a 371 of PCT/KR2015/014482, filed on Dec. 30, 2015 which claims the benefit of Korean Patent Application No. 10-2015-0056322, filed Apr. 22, 2015 the contents of each of which are incorporated herein by reference.

BACKGROUND OF THE INVENTION

1. Field of the Invention

The present invention relates to a 4-(2-amino-tetrahydronaphthaleneyl)pyrimidine derivative, a preparation method thereof, and a pharmaceutical composition for the prevention or treatment of cancer comprising the same as an active ingredient.

2. Description of the Related Art

Cells are the smallest units that make up a human body. Cells are divided and grow by the regulatory function of the cells themselves. When they reach their lifespan or become damaged, they kill themselves and maintain an overall balance of numbers. However, when the regulatory function of these cells is not functioning normally due to various reasons, the cells to be killed are abnormally proliferated and invade tissues around and other organs to form a mass, leading to the formation of a tumor.

Unlike a normal cell that is proliferated or suppressed according to a certain rule and a necessary manner, the cancer cell is unlimitedly proliferated in a tissue in disregard of such necessary rules and manners, and cancer is a cell mass made of such unlimitedly proliferating undifferentiated cells. The unlimitedly proliferating cancer cells invade into the tissues around and even to the other organs with causing a serious pain and problems and even death, so that cancer is regarded as an incurable disease.

According to the report by American Cancer Society, new patients diagnosed with cancer in 2007 world-widely were at least 12 million people, among which 7.6 million people were dead, indicating that approximately 20,000 patients were dead by cancer every day. In Korea, death of cancer was the number 1 cause of death in 2006, according to the report by Statistics Korea. Therefore, it is urgently requested to develop an anticancer agent which is excellent in cancer treating effect in order to reduce emotional and physical pain caused by cancer outbreak and experienced in the course of treating cancer and at the same time to increase quality of life of a patient.

The mechanism of normal cells being cancer cells has not been clearly understood. Cancer is developed by the combined actions of external factors such as environmental factors, chemicals, radiation, and virus and internal factors such as genetic factors and immunological factors. Genes involved in the cancer development are oncogenes and tumor suppressor genes. When the balance between the two cancer-associated genes is broken by any internal or external factors mentioned above, cancer is developed.

Cancer is largely divided into blood cancer that show abnormalities in the number of blood cells and solid cancer in the form of cell masses with constant hardness and morphology in the body. Cancer can be developed in almost every body parts, resulting in lung cancer, stomach cancer, breast cancer, oral cavity cancer, liver cancer, uterine cancer, esophageal cancer, and skin cancer, etc. Surgical operation, radiotherapy, and chemotherapy to suppress cell proliferation are the major anticancer treatment methods.

However, the chemotherapy is not the targeted therapy and the biggest problem of the conventional chemotherapy is side effect caused by cytotoxicity and drug resistance, which is the reason of failure in the treatment using an anticancer agent even after the successful early treatment with it. To overcome the limit of the chemotherapy, it is constantly required to develop a targeted agent based on the clear understanding on the anticancer mechanism of it.

Thus, studies have been undergoing with specific molecular biological factors involved in tumor formation, in order to develop a targeted agent. In particular, the molecular biological factors are used in the prediction of cancer prognosis or in making decision of chemotherapy or radiotherapy.

Recently, drugs such as Gleevec or Herceptin have been used as a targeted agent for bone marrow cancer or breast cancer. Gleevec is the drug that can suppress tyrosine kinase receptor, one of the molecular biological factors involved in cancer. Gleevec displays an anticancer effect by suppressing Bcr-Abl fusion gene formed by translocation in Philadelphia chromosome observed in chronic myelocytic leukemia, which is one of tyrosine kinase inhibitors and has been effective in treating chronic myelocytic leukemia. Gleevec is a tyrosine kinase inhibitor that is used as a targeted agent for chronic myelocytic leukemia. When Gleevec is administered to patients with chronic myelocytic leukemia, it has achieved satisfactory therapeutic results.

Other anticancer agents as a tyrosine kinase inhibitor are Gefitinib and Erlotinib which are EGFR (epidermal growth factor receptor) tyrosine kinase suppressors used in the treatment of non-small cell lung cancer, and Sorafenib and Sunitinib which are used in the treatment of renal cell carcinoma. However, these drugs display such side effects as hemorrhage, heart attack, heart failure, and liver failure, etc.

Recently, anaplastic lymphoma kinase (ALK) was identified in various tumors, so that it has been a target of study.

In the ALK-mediated cancer development, the ALK-NPM (Nucleophosmin) fusion gene found in anaplastic large cell lymphoma is known to be a key factor. Once ALK is activated by gene fusion, tyrosine kinase included in ALK starts abnormal action to cause cancer. That is, the abnormally activated anaplastic lymphoma kinase (ALK) induces cell proliferation, interrupts apoptosis in order to prevent cell death, to rearrange cytoskeleton, and accordingly to transform cell shape.

Oncogenic conversion of anaplastic lymphoma kinase (ALK) is accomplished by the interaction between ALK and its downstream molecule. The downstream molecule is a material to mediate the intracellular signal transduction. ALK interacts with normal genes or other oncogenic converted tyrosine kinase genes to activate various other pathways.

In particular, ALK gene in the lung cancer cell is fused with EML4 (Echinoderm Microtubule-Associated Protein-Like 4) gene to produce EML4-ALK, the active tyrosine kinase. At this time, the cancer inducing activity of EML4-ALK is dependent on the enzyme activity. It has been also reported by Mosse, et al that about 26% ALK gene amplification has been confirmed in 491 neuroblastoma samples. In addition, the ALK gene is found in many nonhematopoietic cell tumors including large B-cell lymphoma, systemic histiocytosis, inflammatory myofibroblastoma, esophageal squamous cell carcinoma, non-small cell lung cancer, rhabdomysarcoma, myofibroblastic tumor, breast cancer, and melanoma cell lines. In inflammatory myeloid blastoma, which is a rare disease, different kinds of anaplastic lymphoma kinase (ALK) fusion proteins are frequently observed, suggesting that such fusion proteins are involved deeply in the tumor development.

An anticancer agent targeting ALK-NPM is under development by using the method to block the ALK activation pathway. It has been recently confirmed by Pfizer that Crizotinib (PF-02341066) which is one of the small molecule tyrosine kinase inhibitors developed as a tumorigenic mutation specific inhibitor is effective in treating non-small cell lung cancer by inhibiting ATP competitive c-Met/HGFR (hepatocyte growth factor receptor) and ALK and accordingly it has been approved as a new drug by FDA in 2011. It was also confirmed that LDK-378 (Ceritinib) developed by Novartis. And clinical trials of multiple anaplastic lymphoma kinase (ALK) inhibitors are in progress.

Patent references 1~3 describe that the therapeutic agent candidates having various frames are under development in order to suppress ALK activity and a pyrimidine derivative can selectively inhibit ALK so that it can be developed as an anticancer agent.

Thus, the present inventors tried to develop a compound which is effective in suppressing anaplastic lymphoma kinase (ALK) activity. As a result, the inventors found out that a 4-(2-amino-tetrahydronaphthaleneyl) pyrimidine derivative in a specific structure was excellent in inhibiting ALK activity so that it could be used as a cancer preventive or cancer treating agent, leading to the completion of this invention.

PRIOR ART REFERENCE

Patent Reference

WO 2009143389 A1
WO 2008051547 A1
WO 2004080980 A1

SUMMARY OF THE INVENTION

It is an object of the present invention to provide a 4-(2-amino-tetrahydronaphthaleneyl)pyrimidine derivative, an optical isomer thereof, or a pharmaceutically acceptable salt of the same.

It is another object of the present invention to provide a method for preparing the said 4-(2-amino-tetrahydronaphthaleneyl)pyrimidine derivative.

It is also an object of the present invention to provide a pharmaceutical composition comprising the said 4-(2-amino-tetrahydronaphthaleneyl)pyrimidine derivative, the optical isomer thereof, or the pharmaceutically acceptable salt of the same as an active ingredient for the prevention or treatment of cancer.

It is further an object of the present invention to provide a health functional food composition comprising the said 4-(2-amino-tetrahydronaphthaleneyl)pyrimidine derivative, the optical isomer thereof, or the pharmaceutically acceptable salt of the same as an active ingredient for the prevention or improvement of cancer.

To achieve the above objects, the present invention provides a compound represented by formula 1, an optical isomer thereof, or a pharmaceutically acceptable salt of the same:

[Formula 1]

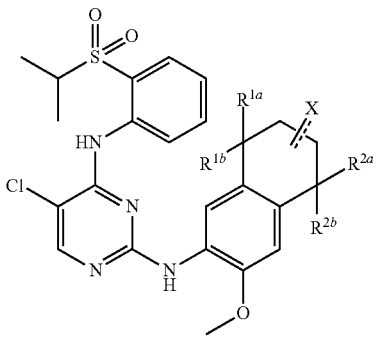

In the formula 1, $R^{1a}$, $R^{1b}$, $R^{2a}$ and $R^{2b}$ are independently hydrogen or $C_{1-5}$ straight or branched alkyl, and $R^{1a}$ and $R^{1b}$ or $R^{2a}$ and $R^{2b}$ can form oxo group (═O);

╌╌ indicates either single bond or double bond;

when ╌╌ is single bond,

X is —OH or —NR³R⁴, wherein, R³ and R⁴ are independently hydrogen, $C_{1-5}$ straight or branched alkyl, —(C═NH)—R⁵, or —(C═O)(CH₂)ₙR⁵, wherein, R⁵ is hydrogen, methyl, —OH, —N(CH₃)₂, —NH₂, or trihalomethyl, and n is an integer of 0~3, R³ and R⁴ can form 5~8 membered unsubstituted or substituted heterocycloalkyl containing one or more hetero atoms selected from the group consisting of N, O, and S along with the nitrogen atoms conjugated to the same;

when ╌╌ is double bond,

X is ═O, ═N—OH or ═N—NR⁶R⁷, wherein, R⁶ and R⁷ are independently hydrogen, $C_{1-5}$ straight or branched alkyl, —(C═O)R⁸ or —(C═NH)R⁸, wherein, R⁸ is methyl, —NH₂ or $C_{1-5}$ straight or branched alkoxy, R⁶ and R⁷ can form 5~8 membered unsubstituted or substituted heterocycloalkyl containing one or more hetero atoms selected from the group consisting of N, O, and S along with the nitrogen atoms conjugated to the same, and the substituted heterocycloalkyl can be substituted with —(C═O)CF₃ or $C_{1-5}$ straight or branched alkyl.

The present invention also provides a method for preparing the compound represented by formula 1 containing the step of preparing the compound represented by formula 1 by reacting the compound represented by formula 2 with the compound represented by formula 3 as shown in reaction formula 1 below:

[Reaction Formula 1]

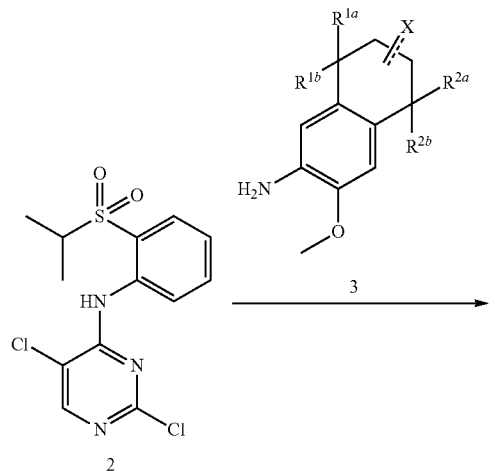

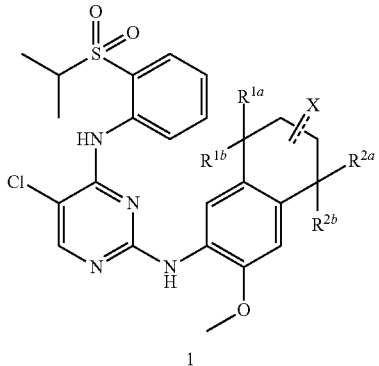

In the reaction formula 1, $R^{1a}$, $R^{1b}$, $R^{2a}$, $R^{2b}$, ----, and X are as defined in formula 1.

In addition, the present invention provides a method for preparing the compound represented by formula 1 containing the step of preparing the compound represented by formula 1b by hydrolyzing the ketone compound represented by formula 1a with the amine compound represented by formula 4 in the presence of an acid as shown in reaction formula 2 below:

[Reaction Formula 2]

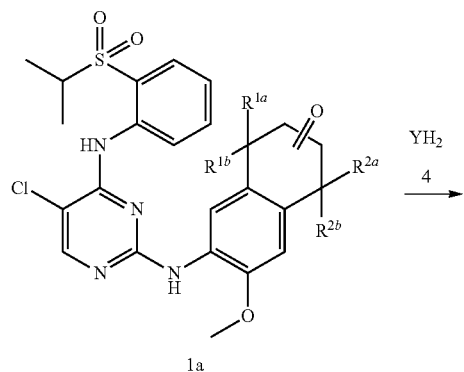

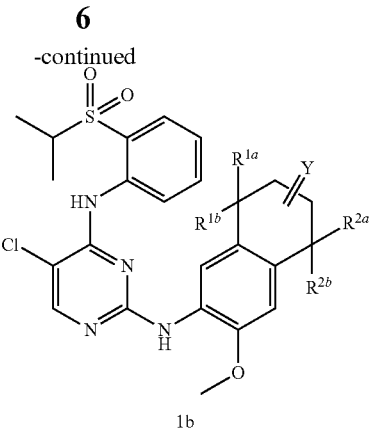

In the reaction formula 2, $R^{1a}$, $R^{1b}$, $R^{2a}$ and $R^{2b}$ are as defined in formula 1;

Y is N—OH or N—$NR^6R^7$, wherein, $R^6$ and $R^7$ are independently hydrogen, $C_{1-5}$ straight or branched alkyl, —(C═O)$R^8$ or —(C═NH)$R^8$, wherein, $R^8$ is methyl, —$NH_2$ or $C_{1-5}$ straight or branched alkoxy, $R^6$ and $R^7$ can form 5-8 membered unsubstituted or substituted heterocycloalkyl containing one or more hetero atoms selected from the group consisting of N, O, and S along with the nitrogen atoms conjugated to the same, and the substituted heterocycloalkyl can be substituted with —(C═O)$CF_3$ or $C_{1-5}$ straight or branched alkyl; and The compound represented by formula 1a or formula 1b is any one of the compounds represented by Formula 1.

The present invention also provides a pharmaceutical composition comprising the compound represented by formula 1, the optical isomer thereof, or the pharmaceutically acceptable salt of the same as an active ingredient for the prevention or treatment of cancer.

In addition, the present invention provides a health functional food composition comprising the compound represented by formula 1, the optical isomer thereof, or the pharmaceutically acceptable salt of the same as an active ingredient for the prevention or improvement of cancer.

Advantageous Effect

The 4-(2-amino-tetrahydronaphthaleneyl)pyrimidine derivative, the optical isomer thereof, or the pharmaceutically acceptable salt thereof of the present invention is very effective in suppressing anaplastic lymphoma kinase (ALK) activity and as a result it can improve the effectiveness of treatment on cancer cells having anaplastic lymphoma kinase (ALK) fusion proteins such as EML4-ALK and NPM-ALK, so that it can be effectively used as a pharmaceutical composition for preventing or treating cancer.

DESCRIPTION OF THE PREFERRED EMBODIMENTS

Hereinafter, the present invention is described in detail.

The present invention provides a compound represented by formula 1, an optical isomer thereof, or a pharmaceutically acceptable salt of the same:

[Formula 1]

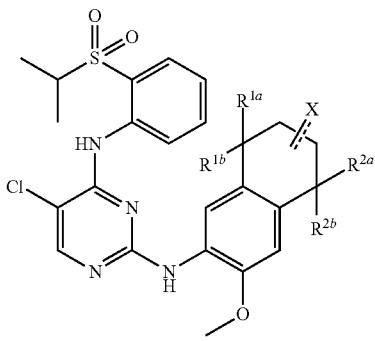

In the formula 1, $R^{1a}$, $R^{1b}$, $R^{2a}$ and $R^{2b}$ are independently hydrogen or $C_{1-5}$ straight or branched alkyl, and $R^{1a}$ and $R^{1b}$ or $R^{2a}$ and $R^{2b}$ can form oxo group (=O);

---- indicates either single bond or double bond;

when ---- is single bond,

X is —OH or —NR$^3$R$^4$, wherein, R$^3$ and R$^4$ are independently hydrogen, $C_{1-5}$ straight or branched alkyl, —(C=NH)—R$^5$, or —(C=O)(CH$_2$)$_n$R$^5$, wherein, R$^5$ is hydrogen, methyl, —OH, —N(CH$_3$)$_2$, —NH$_2$, or trihalomethyl, and n is an integer of 0~3, R$^3$ and R$^4$ can form 5~8 membered unsubstituted or substituted heterocycloalkyl containing one or more hetero atoms selected from the group consisting of N, O, and S along with the nitrogen atoms conjugated to the same, and the substituted heterocycloalkyl can be substituted with —(C=O)CF$_3$;

when ---- is double bond,

X is =O, =N—OH or =N—NR$^6$R$^7$, wherein, R$^6$ and R$^7$ are independently hydrogen, $C_{1-5}$ straight or branched alkyl, —(C=O)R$^8$ or —(C=NH)R$^8$, wherein, R$^8$ is methyl, —NH$_2$ or $C_{1-5}$ straight or branched alkoxy, R$^6$ and R$^7$ can form 5~8 membered unsubstituted or substituted heterocycloalkyl containing one or more hetero atoms selected from the group consisting of N, O, and S along with the nitrogen atoms conjugated to the same, and the substituted heterocycloalkyl can be substituted with —(C=O)CF$_3$ or $C_{1-5}$ straight or branched alkyl.

Preferably, $R^{1a}$, $R^{1b}$, $R^{2a}$ and $R^{2b}$ are independently hydrogen or $C_{1-3}$ straight or branched alkyl, and $R^{1a}$ and $R^{1b}$ can form oxo group (=O);

---- indicates either single bond or double bond;

when ---- is single bond,

X is —OH or —NR$^3$R$^4$, wherein, R$^3$ and R$^4$ are independently hydrogen, $C_{1-3}$ straight or branched alkyl, —(C=NH)—R$^5$, or —(C=O)(CH$_2$)$_n$R$^5$, wherein, R$^5$ is hydrogen, methyl, —OH, —N(CH$_3$)$_2$, or —CF$_3$, and n is an integer of 0~1, R$^3$ and R$^4$ can form 6 membered unsubstituted or substituted heterocycloalkyl containing one or more hetero atoms selected from the group consisting of N and O along with the nitrogen atoms conjugated to the same, and the substituted heterocycloalkyl can be substituted with —(C=O)CF$_3$;

when ---- is double bond,

X is =O, =N—OH or =N—NR$^6$R$^7$, wherein, R$^6$ and R$^7$ are independently hydrogen, $C_{1-3}$ straight or branched alkyl, —(C=O)R$^8$ or —(C=NH)R$^8$, wherein, R$^8$ is methyl, —NH$_2$ or $C_{1-3}$ straight or branched alkoxy, R$^6$ and R$^7$ can form 6 membered unsubstituted or substituted heterocycloalkyl containing one or more hetero atoms selected from the group consisting of N and O along with the nitrogen atoms conjugated to the same, and the substituted heterocycloalkyl can be substituted with —(C=O)CF$_3$ or $C_{1-3}$ straight or branched alkyl.

More preferably, $R^{1a}$, $R^{1b}$, $R^{2a}$ and $R^{2b}$ are independently hydrogen or methyl, and $R^{1a}$ and $R^{1b}$ can form oxo group (=O);

---- indicates either single bond or double bond;

when ---- is single bond,

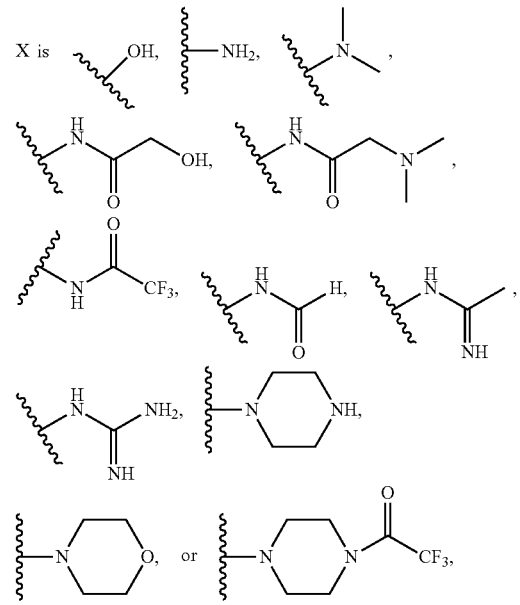

when ---- is double bond

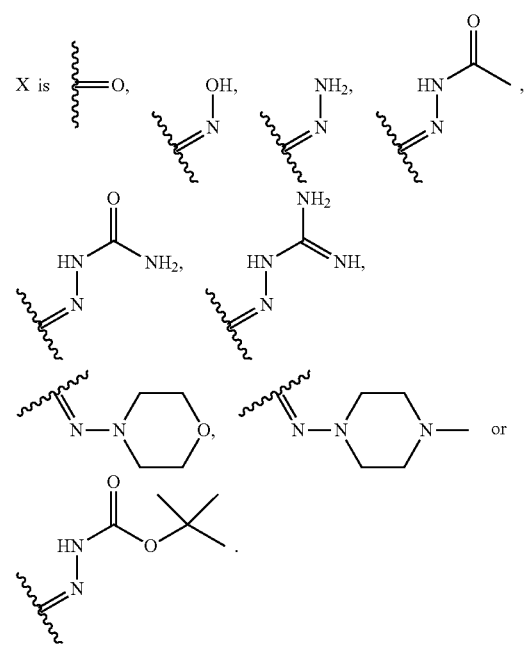

The compound represented by formula 1 of the present invention can be exemplified by the following compounds:

(1) 5-chloro-N4-(2-(isopropylsulfonyl)phenyl)-N2-(3-methoxy-6-morpholino-5,6,7,8-tetrahydronaphthalene-2-yl)pyrimidine-2,4-diamine;
(2) 5-chloro-N4-(2-(isopropylsulfonyl)phenyl)-N2-(3-methoxy-6-(piperazine-1-yl)-5,6,7,8-tetrahydronaphthalene-2-yl)pyrimidine-2,4-diamine;
(3) 7-(5-chloro-4-(2-(isopropylsulfonyl)phenylamino)pyrimidine-2-ylamino)-6-methoxy-2-morpholino-3,4-dihydronaphthalene-1(2H)-one;
(4) N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2,2,2-trifluoroacetamide;
(5) 6-(5-chloro-4-(2-(isopropylsulfonyl)phenylamino)pyrimidine-2-ylamino)-7-methoxy-1,1-dimethyl-3,4-dihydronaphthalene-2(1H)-one;
(6) 7-(5-chloro-4-(2-(isopropylsulfonyl)phenylamino)pyrimidine-2-ylamino)-6-methoxy-1,1-dimethyl-3,4-dihydronaphthalene-2(1H)-one;
(7) N-(7-(5-chloro-4-(2-(isopropylsulfonyl)phenylamino)pyrimidine-2-ylamino)-6-methoxy-1,1-dimethyl-1,2,3,4-tetrahydronaphthalene-2-yl)-2,2,2-trifluoroacetamide;
(8) (E)-6-(5-chloro-4-(2-(isopropylsulfonyl)phenylamino)pyrimidine-2-ylamino)-7-methoxy-1,1-dimethyl-3,4-dihydronaphthalene-2(1H)-one oxime;
(9) (E)-N'-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)acetohydrazide;
(10) (E)-2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrazinecarboxamide;
(11) (E)-2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrazinecarboxamideamide;
(12) (E)-tert-butyl 2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrazinecarboxylate;
(13) (E)-5-chloro-N2-(6-hydrazono-3-methoxy-5,5-dimethyl-5,6,7,8-tetrahydronaphthalene-2-yl)-N4-(2-(isopropylsulfonyl)phenyl)pyrimidine-2,4-diamine hydrochloride;
(14) (E)-5-chloro-N4-(2-(isopropylsulfonyl)phenyl)-N2-(3-methoxy-5,5-dimethyl-6-(4-methylpiperazine-1-ylimino)-5,6,7,8-tetrahydronaphthalene-2-yl)pyrimidine-2,4-diamine;
(15) (E)-5-chloro-N4-(2-(isopropylsulfonyl)phenyl)-N2-(3-methoxy-5,5-dimethyl-6-(morpholinoimino)-5,6,7,8-tetrahydronaphthalene-2-yl)pyrimidine-2,4-diamine;
(16) (E)-7-(5-chloro-4-(2-(isopropylsulfonyl)phenylamino)pyrimidine-2-ylamino)-6-methoxy-1,1-dimethyl-3,4-dihydronaphthalene-2(1H)-one oxime;
(17) (E)-5-chloro-N4-(2-(isopropylsulfonyl)phenyl)-N2-(3-methoxy-8,8-dimethyl-7-(morpholinoimino)-5,6,7,8-tetrahydronaphthalene-2-yl)pyrimidine-2,4-diamine;
(18) (E)-2-(7-(5-chloro-4-(2-(isopropylsulfonyl)phenylamino)pyrimidine-2-ylamino)-6-methoxy-1,1-dimethyl-3,4-dihydronaphthalene-2(1H)-yladene)hydrazinamideamide;
(19) (E)-5-chloro-N4-(2-(isopropylsulfonyl)phenyl)-N2-(3-methoxy-8,8-dimethyl-7-(4-methylpiperazine-1-ylimino)-5,6,7,8-tetrahydronaphthalene-2-yl)pyrimidine-2,4-diamine;
(20) (E)-N'-(7-(5-chloro-4-(2-(isopropylsulfonyl)phenylamino)pyrimidine-2-ylamino)-6-methoxy-1,1-dimethyl-3,4-dihydronaphthalene-2(1H)-yladene)acetohydrazide;
(21) (E)-2-(7-(5-chloro-4-(2-(isopropylsulfonyl)phenylamino)pyrimidine-2-ylamino)-6-methoxy-1,1-dimethyl-3,4-dihydronaphthalene-2(1H)-yladene)hydrazinecarboxamide;
(22) N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine;
(23) N2-(7-amino-3-methoxy-8,8-dimethyl-5,6,7,8-tetrahydronaphthalene-2-yl)-5-chloro-N4-(2-(isopropylsulfonyl)phenyl)pyrimidine-2,4-diamine;
(24) 6-(5-chloro-4-(2-(isopropylsulfonyl)phenylamino)pyrimidine-2-ylamino)-7-methoxy-1,1-dimethyl-1,2,3,4-tetrahydronaphthalene-2-ol;
(25) 7-(5-chloro-4-(2-(isopropylsulfonyl)phenylamino)pyrimidine-2-ylamino)-6-methoxy-1,1-dimethyl-1,2,3,4-tetrahydronaphthalene-2-ol;
(26) N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2-hydroxyacetamide;
(27) N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2-(dimethylamino)acetamide;
(28) 5-chloro-N2-(6-(dimethylamino)-3-methoxy-5,5-dimethyl-5,6,7,8-tetrahydronaphthalene-2-yl)-N4-(2-(isopropylsulfonyl)phenyl)pyrimidine-2,4-diamine;
(29) N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)formimideamide;
(30) N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)acetimideamide; and
(31) N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)guanidine.

The compound represented by formula 1 of the present invention can be used as a form of a pharmaceutically acceptable salt, in which the salt is preferably acid addition salt formed by pharmaceutically acceptable free acids.

The acid addition salt herein can be obtained from inorganic acids such as hydrochloric acid, nitric acid, phosphoric acid, sulfuric acid, hydrobromic acid, hydriodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

The present invention includes not only the compound represented by formula 1 but also a pharmaceutically acceptable salt thereof, and a solvate, an optical isomer, or a hydrate possibly produced from the same.

The present invention also provides a method for preparing the compound represented by formula 1 containing the step of preparing the compound represented by formula 1 by reacting the compound represented by formula 2 with the compound represented by formula 3 as shown in reaction formula 1 below.

represented by formula 2 with the compound represented by formula 3. Particularly, the compound represented by formula 1 was prepared by reacting the compound represented by formula 2 with the compound represented by formula 3 in the presence of an organic solvent and an acid.

At this time, the solvent used herein was selected from the group consisting of tetrahydrofuran (THF); dioxane; ether solvents including ethylether and 1,2-dimethoxyethane; lower alcohols including methanol, ethanol, propanol, and butanol; dimethylformamide (DMF), dimethylsulfoxide, and acetonitrile.

The acid used herein was selected from the group consisting of acetic acid, trifluoroacetic acid, hydrochloric acid, sulfuric acid, and toluene sulfonic acid, and hydrochloric acid or toluene sulfonic acid was preferably selected.

At this time, the reaction was preferably performed at a temperature between 0° C. and the boiling point of the solvent, and the reaction time was not particularly limited, but it was preferably 0.5~24 hours.

In addition, the present invention provides a method for preparing the compound represented by formula 1 containing the step of preparing the compound represented by formula 1b by hydrolyzing the ketone compound represented by formula 1a with the amine compound represented by formula 4 in the presence of an acid as shown in reaction formula 2 below:

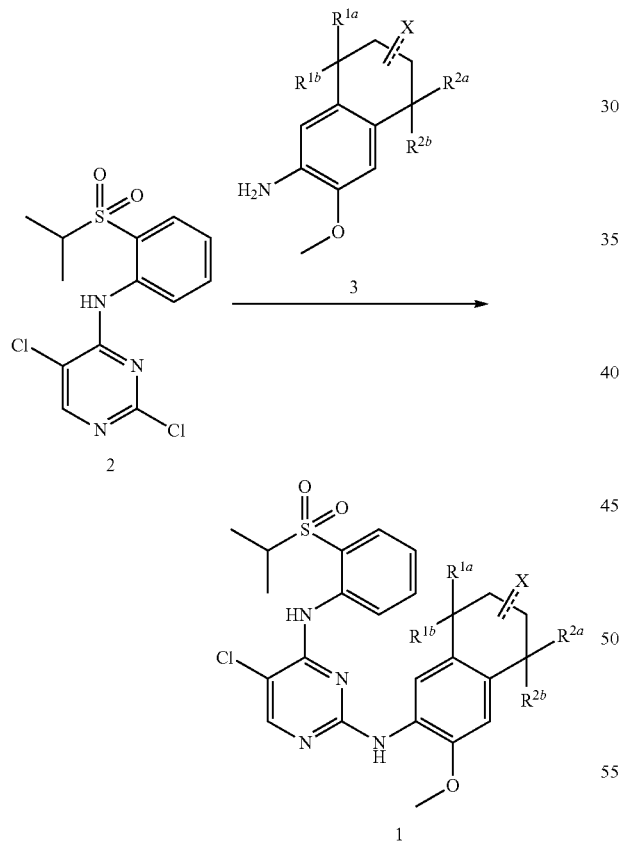

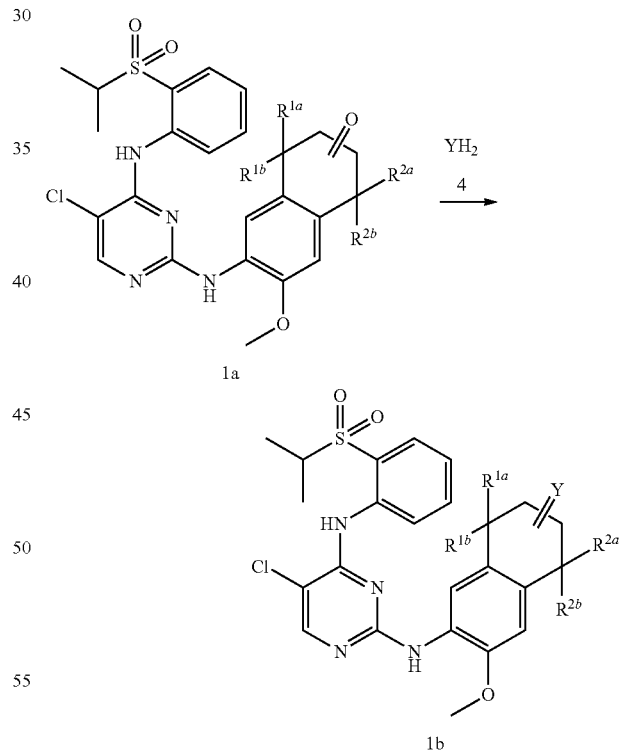

In the reaction formula 1, $R^{1a}$, $R^{1b}$, $R^{2a}$, $R^{2b}$, ====, and X are as defined in formula 1. ====

Hereinafter, the method for preparing the compound represented by formula 1 of the present invention is described in more detail.

In the method for preparing the compound represented by formula 1 of the present invention, the compound represented by formula 1 was prepared by reacting the compound In the reaction formula 2, $R^{1a}$, $R^{1b}$, $R^{2a}$ and $R^{2b}$ are as defined in formula 1;

Y is N—OH or N—NR$^6$R$^7$, wherein, $R^6$ and $R^7$ are independently hydrogen, $C_{1-5}$ straight or branched alkyl, —(C=O)R$^8$ or —(C=NH)R$^8$, wherein, $R^8$ is methyl, —NH$_2$ or $C_{1-5}$ straight or branched alkoxy, $R^6$ and $R^7$ can form 5~8 membered unsubstituted or substituted heterocycloalkyl containing one or more hetero atoms selected from the group consisting of N, O, and S along with the nitrogen atoms conjugated to the same, and the substituted heterocycloalkyl can be substituted with —(C═O)CF$_3$ or C$_{1-5}$ straight or branched alkyl; and The compound represented by formula 1a or formula 1b is any one of the compounds represented by Formula 1.

Hereinafter, the method for preparing the compound represented by formula 1 of the present invention is described in more detail.

In the method for preparing the compound represented by formula 1 of the present invention, the compound represented by formula 1b was prepared by hydrolyzing the ketone compound represented by formula 1a with the amine compound represented by formula 4 in the presence of an acid as shown in reaction formula 2.

Particularly, the compound represented by formula 1b was prepared by reacting the ketone compound represented by formula 1a with the amine compound represented by formula 4 in the presence of an organic acid, an acid, or a base.

At this time, the solvent used herein was selected from the group consisting of tetrahydrofuran (THF); dioxane; ether solvents including ethylether and 1,2-dimethoxyethane; lower alcohols including methanol, ethanol, propanol, and butanol; dimethylformamide (DMF), dimethylsulfoxide, and acetonitrile.

The acid used herein was selected from the group consisting of acetic acid, trifluoroacetic acid, hydrochloric acid, sulfuric acid, and toluene sulfonic acid, and sulfuric acid was preferably selected. The acid was preferably used in a catalytic amount.

The base used herein was selected from the group consisting of inorganic bases such as sodium acetate, sodium hydroxide, sodium carbonate, potassium carbonate, cesium carbonate, and sodium hydride; pyridine, triethylamine, N,N-diisopropylethylamine (DIPEA), and 1,8-diazabicyclo[5.4.0]-7undecene (DBU), and sodium acetate was preferably selected.

At this time, the reaction was preferably performed at a temperature between 0° C. and the boiling point of the solvent, and the reaction time was not particularly limited, but it was preferably 0.5~24 hours.

The present invention also provide a pharmaceutical composition comprising the compound represented by formula 1, the optical isomer thereof, or the pharmaceutically acceptable salt of the same as an active ingredient for the prevention or treatment of cancer. The pharmaceutical composition is characterized by the inhibition of the expression and the growth of cancer cells by suppressing the activation of anaplastic lymphoma kinase (ALK). The cancer herein is exemplified by non-small cell lung cancer, neuroblastoma, inflammatory myelofibroblastoma, rhabdomyosarcoma, myofibroblastoma, breast cancer, stomach cancer, lung cancer, and melanoma.

ALK is the gene inducing the proliferation of cancer cells, which is activated by gene fusion. At this time, a tyrosine kinase included in ALK starts acting abnormally to induce cell proliferation, interrupt apoptosis, re-arrange cytoskeleton, transform cell shape, and activates other pathways or interacts with other tyrosine kinases which are either normal or oncogenic.

Thus, experiments were performed to measure the inhibitory effect of the 4-(2-amino-tetrahydronaphthaleneyl)pyrimidine derivative represented by formula 1 of the present invention on the activity of ALK at the enzyme level. As a result, the compounds prepared in examples of the present invention were confirmed to effectively reduce the activity of ALK. In particular, the compounds prepared in examples 1, 2, 14, 21, 22, 26, 27, and 28 exhibited excellent anaplastic lymphoma kinase (IR) inhibition activity at the concentration of 0.01 μM or less (see Table 2 of Experimental Example 1).

Experiments were performed to measure the inhibitory effect of the 4-(2-amino-tetrahydronaphthaleneyl)pyrimidine derivative represented by formula 1 of the present invention on the activity of ALK at the cell level. As a result, the compounds prepared in examples of the present invention showed inhibitory effect on ALK L1196M containing ALK enzyme. In particular, the compounds prepared in examples 2, 14, 22, 26, 27, and 28 demonstrated excellent inhibitory effect on ALK L1196M containing ALK enzyme at the concentration of 0.01 μM or less (see Table 2 of Experimental Example 2).

In addition, the inhibitory activity of the compounds prepared in examples of the present invention in non-small cell lung cancer cells and EML4 (Echiinoderm Microtubule-Associated Protein-like 4)-ALK mutant form L1196M cells was also measured. As a result, the compounds prepared in examples of the present invention were confirmed to have inhibitory activity in the non-small cell lung cancer cells and EML4 (Echiinoderm Microtubule-Associated Protein-like 4)-ALK mutant form L1196M cells. In particular, the compounds prepared in examples 1, 2, 5, 13, 14, 15, 22, 24, 26, 27, and 28 displayed excellent inhibitory activity in the non-small cell lung cancer cells at the concentration between 0.01~0.1 μM. In the meantime, the compounds prepared in examples 1, 2, 14, 22, 26, 27, and 28 demonstrated excellent inhibitory activity in the EML4 (Echiinoderm Microtubule-Associated Protein-like 4)-ALK mutant form L1196M cells at the concentration between 0.01~0.1 μM (see Table 2 of Experimental Examples 3 and 4).

Therefore, the 4-(2-amino-tetrahydronaphthaleneyl)pyrimidine derivative represented by formula 1 of the present invention was confirmed to have excellent inhibitory effect on the activity of ARK, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

The compound represented by formula 1 of the present invention can be administered orally or parenterally in various formulations at the time of clinical administration. The formulations can be prepared by mixing the compound of the invention with generally used diluents or excipients such as fillers, extenders, binders, wetting agents, disintegrants, and surfactants.

The formulations for oral administration are exemplified by tablets, pills, powders, granules, capsules, and troches (candy type), etc. Such solid preparations are prepared by mixing one or more compounds of the present invention with one or more excipients such as starch, calcium carbonate, sucrose, lactose and gelatin. Except for the simple excipients, lubricants, for example magnesium stearate, talc, etc, can be used. Liquid formulations for oral administrations are suspensions, solutions (medicines dissolved or dispersed in water or organic solvents), emulsions or syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories.

Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The effective dosage of the compound of the present invention can be adjusted according to age, weight, and gender of patient, administration pathway, health condition, severity of disease, etc. For example, the effective dosage is generally 0.001~100 mg/kg/day, and preferably 0.01~35 mg/kg/day. Based on an adult patient weighing 70 kg, the effective dosage is generally 0.07~7000 mg/day, and preferably 0.7~2500 mg/day, which can be administered 1~several times a day or the dosage can be divided and administered several times a day at a regular interval according to the judgment of a doctor or a pharmacist.

In addition, the present invention provides a health functional food composition comprising the 4-(2-amino-tetrahydronaphthaleneyl)pyrimidine derivative represented by formula 1, the optical isomer thereof, or the pharmaceutically acceptable salt of the same as an active ingredient for the prevention or improvement of cancer.

Particularly, the food comprising the 4-(2-amino-tetrahydronaphthaleneyl)pyrimidine derivative represented by formula 1, the optical isomer thereof, or the pharmaceutically acceptable salt of the same as an active ingredient herein is not limited. For example, the compound of the present invention can be added to drinks, meats, sausages, breads, biscuits, rice cakes, chocolates, candies, snacks, cookies, pizza, ramyuns, flour products, gums, dairy products including ice cream, soups, beverages, vitamin complex, milk products, and milk-processing products, and in a wide sense, almost every food applicable in the production of health food can be included. The compound of the present invention can be added as it is or as mixed with other food components according to the conventional method.

The 4-(2-amino-tetrahydronaphthaleneyl)pyrimidine derivative represented by formula 1 of the present invention was confirmed to have an excellent activity to inhibit ALK activity, so that it can be effectively used as a health functional food composition for the prevention or improvement of such cancers as non-small cell lung cancer, neuroblastoma, inflammatory myelofibroblastoma, rhabdomyosarcoma, myofibroblastoma, breast cancer, stomach cancer, lung cancer, and melanoma.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1: Preparation of 3-methoxy-6-morpholino-5,6,7,8-tetrahydronaphthalene-2-amine

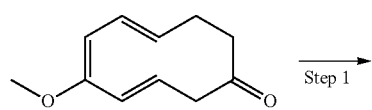
Step 1

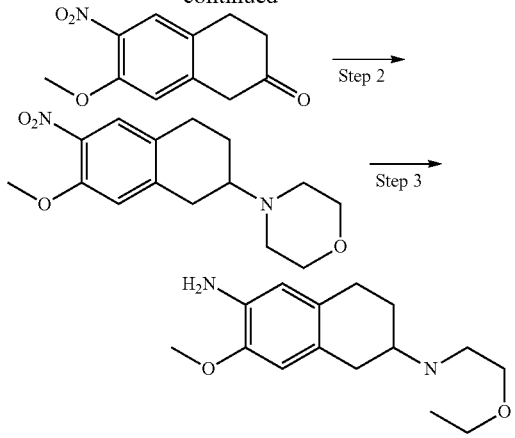

Step 1: Preparation of 7-methoxy-6-nitro-3,4-dihydronaphthalene-2(1H)-one 7-methoxy-3,4-dihydronaphthalene-2(1H)-one (2000 mg, 11.3494 mmol) was dissolved in acetonitrile (200 ml), to which trifluoroaceticanhydride (1.9 mL, 13.6193 mmol) was added. Potassium nitrate (13.6193 mmol) was added thereto at 0° C. little by little at the total amount of 1300 mg. The mixture was stirred at room temperature for 12 hours. The reaction mixture was diluted with dichloromethane, which was placed in ice water, followed by neutralization with sodium hydrogen carbonate. The extracted organic solution was dried over anhydrous magnesium sulfate to eliminate remaining moisture. The reaction mixture was concentrated, followed by recrystallization and silica gel column chromatography. As a result, the target compound 7-methoxy-6-nitro-3,4-dihydronaphthalene-2(1H)-one was obtained as a light brown solid (300 mg, 34%).

$^1$H NMR (300 MHz, CDCl$_3$) δ 7.78 (s, 1H), 6.84 (s, 1H), 3.95 (s, 3H), 3.64 (s, 2H), 3.09-3.04 (m, 2H), 2.60-2.55 (m, 2H)

Step 2: Preparation of 4-(7-methoxy-6-nitro-1,2,3,4-tetrahydronaphthalene-2-yl)morpholine 7-methoxy-6-nitro-3,4-dihydronaphthalene-2(1H)-one (100 mg, 0.4524 mmol) prepared in step 1 was dissolved in dichloroethane (3 mL), to which morpholine (102 μL, 0.9048 mmol) and acetic acid (31 μL, 0.5428 mmol) were added, followed by stirring at 50° C. The reaction mixture was cooled down at room temperature. After cooling, sodiumtriacetoxyborohydride (143 mg, 0.6786 mmol) was added to the mixture, followed by stirring. Upon completion of the reaction, the reaction mixture was neutralized with sodium hydrogen carbonate, followed by extraction with dichloromethane. The extracted organic solution was dried over anhydrous magnesium sulfate to eliminate remaining moisture. The mixture was then concentrated to give the target compound 4-(7-methoxy-6-nitro-1,2,3,4-tetrahydronaphthalene-2-yl)morpholine (70 mg, 0.2739 mmol, 75%).

$^1$H NMR (300 MHz, CDCl$_3$) δ 7.73-7.72 (m, 1H), 6.53 (s, 1H), 3.96-3.95 (m, 3H), 3.92-3.77 (m, 3H), 3.63 (s, 1H), 3.16-3.13 (m, 4H), 2.85-2.83 (m, 2H), 2.81-2.80 (m, 1H), 2.43-2.38 (m, 3H)

Step 3: Preparation of 3-methoxy-6-morpholino-5,6,7,8-tetrahydronaphthalene-2-amine 4-(7-methoxy-6-nitro-1,2,3,4-tetrahydronaphthalene-2-yl)morpholine (80 mg, 0.2739 mmol) prepared in step 2 and 10 weight % palladium/charcoal (20 mg) were hydrogenated in the presence of methanol (20 mL) solvent. Upon completion of the reaction, the reactant was filtered with celite and then washed with ethylacetate. The filtered organic solvent was concentrated under reduced pressure, followed by purification with silica gel column chromatography. As a result, the target compound 3-methoxy-6-morpholino-5,6,7,8-tetrahydronaphthalene-2-amine was obtained as a purple solid (44 mg, 0.1679 mmol, 54%).

$^1$H NMR (300 MHz, CDCl$_3$) δ 6.49 (s, 1H), 6.44 (s, 1H), 3.80-3.67 (m, 5H), 3.67-3.66 (m, 1H), 2.83-2.82 (m, 1H), 2.65-2.55 (m, 4H), 2.08-2.05 (m, 1H)

Preparative Example 2: Preparation of 1-(4-(6-amino-7-methoxy-1,2,3,4-tetrahydronaphthalene-2-yl)piperazine-1-yl)-2,2,2-trifluoroethanone

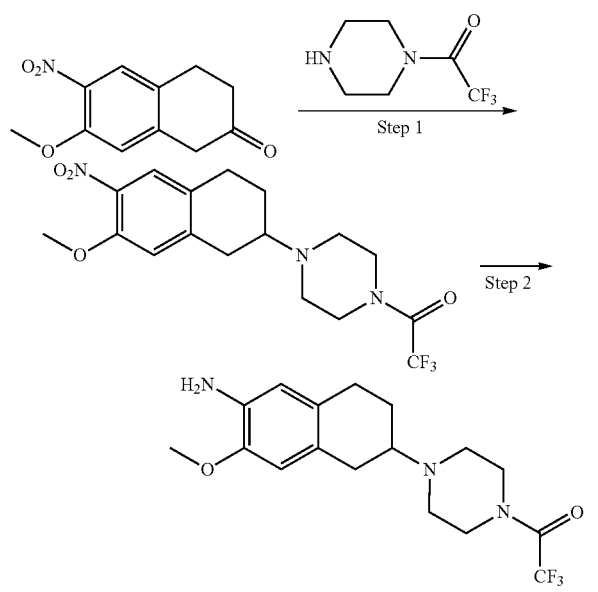

Step 1: Preparation of 2,2,2-trifluoro-1-(4-(7-methoxy-6-nitro-1,2,3,4-tetrahydronaphthalene-2-yl)piperazine-1-yl)ethanone 7-methoxy-6-nitro-3,4-dihydronaphthalene-2(1H)-one (0.1 g, 1 eq) was dissolved in dichloroethane (2 ml), to which fluoroacetylpiperazine (2 eq) was added. Then, acetic acid (catalytic amount) was added thereto, followed by stirring at 50° C. The reaction mixture was cooled down at room temperature, to which sodiumtriacetoxyborohydride (1.2 eq) was added, followed by stirring again. Upon completion of the reaction, the reactant was neutralized with sodium bicarbonate aqueous solution, followed by extraction with dichloromethane. The extracted organic solution was dried over anhydrous magnesium sulfate to eliminate remaining moisture, followed by concentration. As a result, the target compound 2,2,2-trifluoro-1-(4-(7-methoxy-6-nitro-1,2,3,4-tetrahydronaphthalene-2-yl)piperazine-1-yl)ethanone was obtained as a purple solid (54%).

$^1$H NMR (300 MHz, CDCl$_3$) δ 7.72 (s, 1H), 6.51 (s, 1H), 5.47 (s, 1H), 3.92 (s, 3H), 3.23-3.20 (m, 3H), 2.84-2.79 (m, 2H), 2.58-2.54 (m, 3H), 2.43-2.36 (m, 5H), 1.35 (s, 1H).

Step 2: Preparation of 1-(4-(6-amino-7-methoxy-1,2,3,4-tetrahydronaphthalene-2-yl)piperazine-1-yl)-2,2,2-trifluoroethanone 2,2,2-trifluoro-1-(piperazine-1-yl)ethanone (1 eq) prepared in step 1 and 10 weight % palladium/charcoal (Pd/C) were hydrogenated in the presence of methanol solvent. Upon completion of the reaction, the reactant was filtered with celite and then washed with ethylacetate. The filtered organic solvent was concentrated under reduced pressure. As a result, the target compound 1-(4-(6-amino-7-methoxy-1,2,3,4-tetrahydronaphthalene-2-yl)piperazine-1-yl)-2,2,2-trifluoroethanone was obtained (46%).

$^1$H NMR (300 MHz, CDCl$_3$) δ 7.08-7.02 (m, 1H), 6.97-6.92 (m, 1H), 3.95 (s, 3H), 3.63 (s, 1H), 3.53-3.49 (m, 1H), 3.33-3.26 (m, 2H), 2.77-2.67 (m, 3H), 2.60-2.56 (m, 1H), 2.47-2.34 (m, 3H), 2.01 (s, 1H), 2.05-2.01 (s, 1H)

Preparative Example 3: Preparation of 7-amino-6-methoxy-2-morpholino-3,4-dihydronaphthalene-1(2H)-one

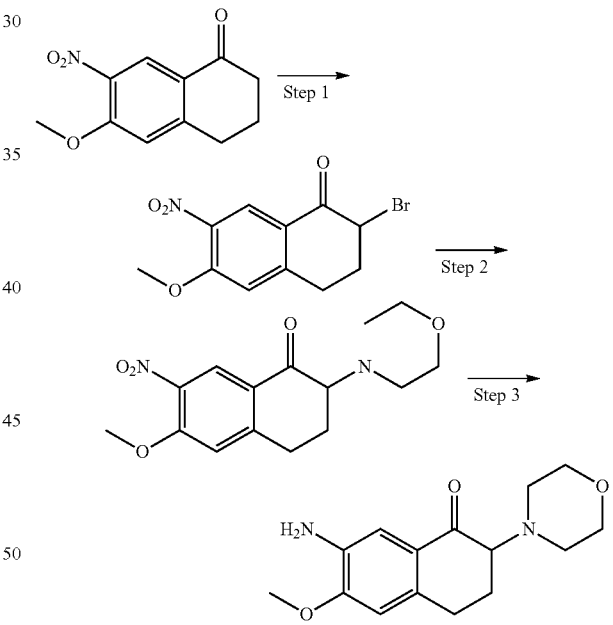

Step 1: Preparation of 2-bromo-6-methoxy-7-nitro-3,4-dihydronaphthalene-1(2H)-one 6-methoxy-7-nitro-3,4-dihydronaphthalene-1(2H)-one (0.5 g) was dissolved in acetonitrile (50 ml), to which N-bromosuccineimide (1.05 eq, 0.53 g) and p-toluenesulfonic acid (1.5 eq, 0.732 g) were added, followed by heat-reflux. Upon completion of the reaction, the reactant was extracted with ethylacetate. The extracted organic layer was dried over anhydrous magnesium sulfate to eliminate remaining moisture, followed by concentration. The concentrate was purified by silica gel column chromatography to give the target compound 2-bromo-6-methoxy-7-nitro-3,4-dihydronaphthalene-1(2H)-one (0.45 g, 85%).

$^{1}$H NMR (300 MHz, CDCl$_{3}$) δ 5.56 (s, 1H), 6.92 (s, 1H), 4.72-4.69 (m, 1H), 4.03 (s, 3H), 3.39-3.33 (m, 1H), 2.99-2.91 (m, 1H), 2.54-2.47 (m, 2H)

Step 2: Preparation of 6-methoxy-2-morpholino-7-nitro-3,4-dihydronaphthalene-1(2H)-one 2-bromo-6-methoxy-7-nitro-3,4-dihydronaphthalene-1(2H)-one (1 eq) prepared in step 1 was dissolved in acetonitrile, to which morpholine (2 eq) was added, followed by boiling for 16 hours. Upon completion of the reaction, the reactant was extracted with dichloromethane. The organic solvent was dried over anhydrous magnesium sulfate to eliminate remaining moisture, followed by concentration. The concentrated mixture was purified by silica gel column chromatography to give the target compound 6-methoxy-2-morpholino-7-nitro-3,4-dihydronaphthalene-1(2H)-one.

$^{1}$H NMR (300 MHz, CDCl$_{3}$) δ 8.48 (s, 1H), 6.87 (s, 1H), 3.99 (s, 3H), 3.78-3.73 (m, 5H), 3.34-3.13 (m, 2H), 3.07-2.90 (m, 2H), 2.80-2.70 (m, 2H), 2.68-2.57 (m, 2H), 2.34-2.22 (m, 2H)

Step 3: Preparation of 7-amino-6-methoxy-2-morpholino-3,4-dihydronaphthalene-1(2H)-one 6-methoxy-2-morpholino-7-nitro-3,4-dihydronaphthalene-1(2H)-one (1 eq) prepared in step 2 and 10 weight % palladium/charcoal (Pd/C) were hydrogenated in the presence of methanol solvent. Upon completion of the reaction, the reactant was filtered with celite and then washed with ethylacetate. The filtered organic solvent was concentrated under reduced pressure. As a result, the target compound 7-amino-6-methoxy-2-morpholino-3,4-dihydronaphthalene-1(2H)-one was obtained.

$^{1}$H NMR (300 MHz, CDCl$_{3}$) δ 7.33 (s, 1H), 6.56 (s, 1H), 3.90 (s, 3H), 3.77-3.74 (m, 5H), 3.34-3.13 (m, 2H), 3.07-2.90 (m, 2H), 2.80-2.70 (m, 2H), 2.68-2.57 (m, 2H), 2.34-2.22 (m, 2H).

Preparative Example 4: Preparation of N-(7-amino-6-methoxy-1,1-dimethyl-1,2,3,4-tetrahydronaphthalene-2-yl)-2,2,2-trifluoroacetamide

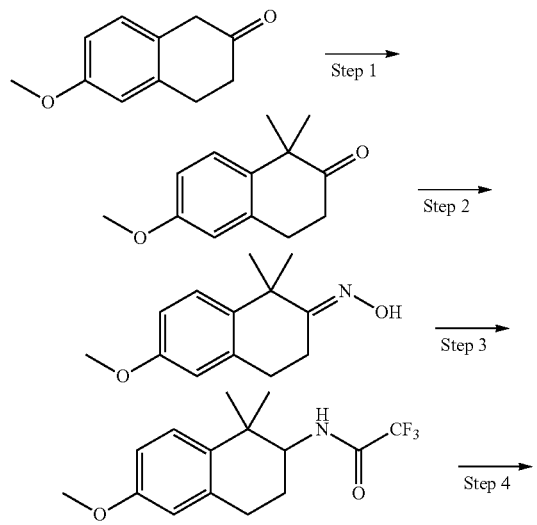

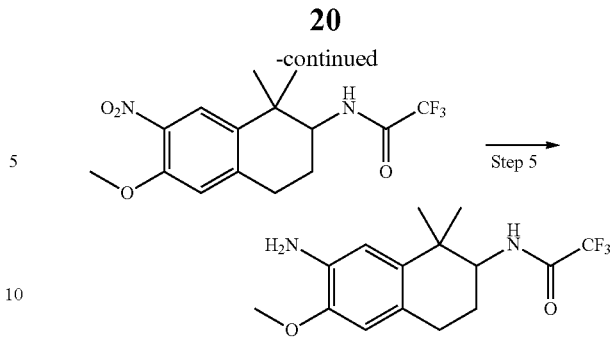

Step 1: Preparation of 6-methoxy-1,1-dimethyl-3,4-dihydronaphthalene-2(1H)-one 6-methoxy-3,4-dihydronaphthalene-2(1H)-one (2 g, 11.4 mmol) was dissolved in tetrahydrofuran, to which tetrabutylammonium sulfate (0.61 g, 1.8 mmol) and methane iodide (2.1 mL, 34.2 mmol) were added. Then, 50% potassium hydroxide solution (13 mL) was added thereto, followed by stirring for 1 hour. Upon completion of the reaction, the reaction solution was diluted with ethylacetate, followed by washing with water. The organic layer was dried over anhydrous magnesium sulfate to eliminate remaining moisture, followed by concentration. Then, purification was performed by silica gel column chromatography to give the target compound 6-methoxy-1,1-dimethyl-3,4-dihydronaphthalene-2(1H)-one (71%).

$^{1}$H NMR (300 MHz, CDCl3) δ 7.25 (d, J=8.40, 1H), 6.82 (d, J=8.40, 1H), 6.7 (s, 1H), 3.8 (s, 3H), 3.0 (t, J=6.90, 2H), 2.68 (t, J=6.90, 2H), 1.41 (s, 6H)

Step 2: Preparation of (E)-6-methoxy-1,1-dimethyl-3,4-dihydronaphthalene-2(1H)-one oxime 6-methoxy-1,1-dimethyl-3,4-dihydronaphthalene-2(1H)-one (1.7 g, 8.6 mmol) prepared in step 1 was dissolved in methanol, to which water (12.3 mL), hydroxylamine hydrochloride (1.7 g, 25.8 mmol), and sodium acetate (2.1 g, 25.8 mmol) were added, followed by stirring at 90° C. Upon completion of the reaction, the reactant was concentrated under reduced pressure, diluted with ethylacetate, and washed with water. The organic layer was dried over anhydrous magnesium sulfate to eliminate remaining moisture, followed by concentration. Then, purification was performed by silica gel column chromatography to give the target compound 6-methoxy-1,1-dimethyl-3,4-dihydronaphthalene-2(1H)-one oxime (97%).

$^{1}$H NMR (300 MHz, CDCl3) δ 7.28 (d, J=8.7, 1H), 6.78 (dd, J=8.7, 2.7, 1H), 6.67 (d, J=2.7, 1H), 3.79 (s, 3H), 2.94-2.82 (m, 4H), 1.48 (s, 6H)

Step 3: Preparation of 2,2,2-trifluoro-N-(6-methoxy-1,1-dimethyl-7-nitro-1,2,3,4-tetrahydronaphthalene-2-yl)-acetamide 6-methoxy-1,1-dimethyl-3,4-dihydronaphthalene-2(1H)-one oxime (0.1 g, 0.456 mmol) prepared in step 2 was dissolved in tetrahydrofuran, to which lithiumaluminum hydride (0.052 g, 1.37 mmol) was slowly added at 0° C., followed by heat-reflux at 70° C. Water was added to terminate the reaction, followed by extraction with ethylacetate. The organic layer was washed with brine and the remaining moisture was eliminated by drying over anhydrous magnesium sulfate, followed by concentration. The concentrated mixture was dissolved in dichloromethane (3 mL), to which triethylamine (0.064 mL, 0.684 mmol) and trifluoroacetic acid anhydride (0.077 mL, 0.547 mmol) were slowly added at 0° C., followed by stirring at room temperature for 1 hour. The reaction solution was diluted with dichloromethane, followed by washing with water and brine. The organic layer was dried over anhydrous magnesium sulfate to eliminate remaining moisture, followed by concentration. Then, purification was performed by silica gel column chromatography to give the target compound 2,2,2-trifluoro-N-(6-methoxy-1,1-dimethyl-7-nitro-1,2,3,4-tetrahydronaphthalene-2-yl)-acetamide (53%).

$^1$H NMR (300 MHz, CDCl$_3$) δ 7.25-7.20 (m, 1H), 6.78 (d, J=9, 1H), 6.61 (s, 1H), 6.19 (s, 1H), 3.78 (s, 3H), 3.33-3.23 (m, 1H), 2.98-2.90 (m, 2H), 2.12-1.91 (m, 2H), 1.33-1.24 (m, 6H).

Step 4: Preparation of 2,2,2-trifluoro-N-(6-methoxy-1,1-dimethyl-1,2,3,4-tetrahydronaphthalene-2-yl)-acetamide 2,2,2-trifluoro-N-(6-methoxy-1,1-dimethyl-7-nitro-1,2,3,4-tetrahydronaphthalene-2-yl)-acetamide (0.1 g, 0.33 mmol) prepared in step 3 was dissolved in trifluoroacetic acid (3 mL), to which potassium nitrate was added at 0° C., followed by stirring at room temperature. Trifluoroacetic acid was concentrated under reduced pressure, diluted with ethylacetate, and washed with water. The organic layer was washed with brine, and dried over anhydrous magnesium sulfate to eliminate remaining moisture, followed by concentration. Then, purification was performed by silica gel column chromatography to give the target compound 2,2,2-trifluoro-N-(6-methoxy-1,1-dimethyl-1,2,3,4-tetrahydronaphthalene-2-yl)-acetamide (32%).

$^1$H NMR (300 MHz, CDCl$_3$) δ 7.90 (s, 1H), 6.78 (s, 1H), 6.16-6.14 (m, 1H), 4.27-4.23 (m, 1H), 3.96 (s, 3H), 3.06-3.01 (m, 1H), 2.97-2.92 (m, 1H), 2.16-2.12 (m, 1H), 2.04-1.99 (m, 1H), 1.38 (s, 3H), 1.32 (s, 3H)

Step 5: Preparation of N-(7-amino-6-methoxy-1,1-dimethyl-1,2,3,4-tetrahydronaphthalene-2-yl)-2,2,2-trifluoroacetamide 2,2,2-trifluoro-N-(6-methoxy-1,1-dimethyl-1,2,3,4-tetrahydronaphthalene-2-yl)-acetamide prepared in step 4 and 10 weight % palladium/charcoal (Pd/C) were hydrogenated in the presence of methanol solvent. Upon completion of the reaction, the reactant was filtered with celite and then washed with ethylacetate. The filtered organic solvent was concentrated under reduced pressure. As a result, the target compound N-(7-amino-6-methoxy-1,1-dimethyl-1,2,3,4-tetrahydronaphthalene-2-yl)-2,2,2-trifluoroacetamide was obtained (78%).

$^1$H NMR (300 MHz, CDCl$_3$) δ 6.65 (s, 1H), 6.46 (s, 1H), 6.16 (m, 1H), 4.20-4.13 (m, 1H), 3.82 (s, 3H), 3.76-3.73 (m, 2H), 2.87-2.72 (m, 2H), 2.11-2.03 (m, 1H), 1.97-1.88 (m, 1H), 1.29-1.25 (m, 6H)

Preparative Example 5: Preparation of N-(6-amino-7-methoxy-1,1-dimethyl-1,2,3,4-tetrahydronaphthalene-2-yl)-2,2,2-trifluoroacetamide

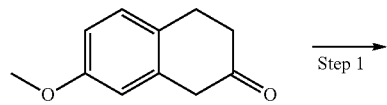

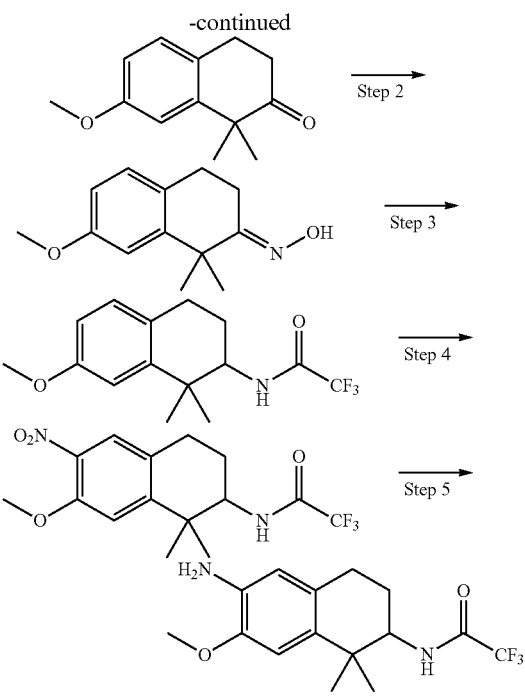

Step 1: Preparation of 7-methoxy-1,1-dimethyl-3,4-dihydronaphthalene-2(1H)-one 7-methoxy-3,4-dihydronaphthalene-2(1H)-one (2 g, 11.4 mmol) was dissolved in tetrahydrofuran, to which tetrabutylammonium sulfate (0.61 g, 1.8 mmol) and methane iodide (2.1 mL, 34.2 mmol) were added. Then, 50% potassium hydroxide solution (13 mL) was added thereto, followed by stirring for 1 hour. Upon completion of the reaction, the reaction solution was diluted with ethylacetate, followed by washing with water. The organic layer was dried over anhydrous magnesium sulfate to eliminate remaining moisture, followed by concentration. Then, purification was performed by silica gel column chromatography to give the target compound 7-methoxy-1,1-dimethyl-3,4-dihydronaphthalene-2(1H)-one (1.7 g, 71%).

$^1$H NMR (300 MHz, CDCl$_3$) δ 7.08 (d, J=8.31, 1H), 6.87 (d, J=2.58, 1H), 6.74 (dd, J=8.31, 2.61, 1H), 3.81 (s, 3H), 3.03 (t, J=6.84, 2H), 2.65 (t, J=6.87, 2H), 1.42 (s, 6H)

Step 2: Preparation of (E)-7-methoxy-1,1-dimethyl-3,4-dihydronaphthalene-2(1H)-one oxime 7-methoxy-1,1-dimethyl-3,4-dihydronaphthalene-2(1H)-one (1.7 g, 8.6 mmol) prepared in step 1 was dissolved in methanol, to which water (12.3 mL), hydroxylamine hydrochloride (1.7 g, 25.8 mmol), and sodium acetate (2.1 g, 25.8 mmol) were added, followed by stirring at 90° C. Upon completion of the reaction, the reaction solution was concentrated under reduced pressure, and diluted with ethylacetate, followed by washing with water. The organic layer was dried over anhydrous magnesium sulfate to eliminate remaining moisture, followed by concentration. Then, purification was performed by silica gel column chromatography to give the target compound (E)-7-methoxy-1,1-dimethyl-3,4-dihydronaphthalene-2(1H)-one oxime (74%).

$^1$H NMR (300 MHz, CDCl$_3$) δ 8.63 (s, 1H), 7.05 (d, J=8.31, 1H), 6.93 (d, J=2.52, 1H), 6.71 (dd, J=8.28, 2.58, 1H), 3.80 (s, 3H), 2.92-2.81 (m, 4H), 1.50 (s, 1H)

Step 3: Preparation of 2,2,2-trifluoro-N-(7-methoxy-1,1-dimethyl-1,2,3,4-tetrahydronaphthalene-2-yl)acetamide 7-methoxy-1,1-dimethyl-3,4-dihydronaphthalene-2(1H)-one oxime (0.1 g, 0.456 mmol) prepared in step 2 was dissolved in tetrahydrofuran, to which lithiumaluminum hydride (0.052 g, 1.37 mmol) was slowly added at 0° C., followed by heat-reflux at 70° C. Water was added to terminate the reaction, followed by extraction with ethylacetate. The organic layer was washed with brine and the remaining moisture was eliminated by drying over anhydrous magnesium sulfate, followed by concentration. The concentrated mixture was dissolved in dichloromethane (3 mL), to which triethylamine (0.064 mL, 0.684 mmol) and trifluoroacetic acid anhydride (0.077 mL, 0.547 mmol) were slowly added at 0° C., followed by stirring at room temperature for 1 hour. The reaction solution was diluted with dichloromethane, followed by washing with water and brine. The organic layer was dried over anhydrous magnesium sulfate to eliminate remaining moisture, followed by concentration. Then, purification was performed by silica gel column chromatography to give the target compound 2,2,2-trifluoro-N-(7-methoxy-1,1-dimethyl-1,2,3,4-tetrahydronaphthalene-2-yl)acetamide (0.1 g, 73%).

$^1$H NMR (300 MHz, CDCl$_3$) δ 7.02 (t, J=9.1 Hz, 1H), 6.87 (s, 1H), 6.83-6.70 (m, 1H), 6.25 (s, 1H), 4.21 (d, J=7.6 Hz, 1H), 3.80 (s, 3H), 3.31 (m, 1H), 3.16 (m, 0.4H), 3.03-2.74 (m, 1.6H), 2.22-1.91 (m, 1H), 1.36 (s, 3H), 1.31 (s, 3H).

Step 4: Preparation of 2,2,2-trifluoro-N-(7-methoxy-1,1-dimethyl-6-nitro-1,2,3,4-tetrahydronaphthalene-2-yl)acetamide 2,2,2-trifluoro-N-(7-methoxy-1,1-dimethyl-1,2,3,4-tetrahydronaphthalene-2-yl)acetamide (0.1 g, 0.33 mmol) prepared in step 3 was dissolved in trifluoroacetic acid (3 mL) to which potassium nitrate was added at 0° C., followed by stirring at room temperature. Trifluoroacetic acid was concentrated under reduced pressure, diluted with ethylacetate, and washed with water. The organic layer was dried over anhydrous magnesium sulfate to eliminate remaining moisture, followed by concentration. Then, purification was performed by silica gel column chromatography to give the target compound 2,2,2-trifluoro-N-(7-methoxy-1,1-dimethyl-6-nitro-1,2,3,4-tetrahydronaphthalene-2-yl)acetamide (0.05 g, 42%).

The compound 2,2,2-trifluoro-N-(7-methoxy-1,1-dimethyl-6-nitro-1,2,3,4-tetrahydronaphthalene-2-yl)acetamide obtained in step 4 contained a small amount of the structural isomer but this compound was used without isolation for the next reaction.

Step 5: Preparation of N-(6-amino-7-methoxy-1,1-dimethyl-1,2,3,4-tetrahydronaphthalene-2-yl)-2,2,2-trifluoroacetamide 2,2,2-trifluoro-N-(7-methoxy-1,1-dimethyl-6-nitro-1,2,3,4-tetrahydronaphthalene-2-yl)acetamide prepared in step 4 and 10 weight % palladium/charcoal (Pd/C) were hydrogenated in the presence of methanol solvent. Upon completion of the reaction, the reactant was filtered with celite and then washed with ethylacetate. The filtered organic solvent was concentrated under reduced pressure. As a result, the target compound N-(6-amino-7-methoxy-1,1-dimethyl-1,2,3,4-tetrahydronaphthalene-2-yl)-2,2,2-trifluoroacetamide was obtained.

$^1$H NMR (300 MHz, CDCl$_3$) δ 6.69 (s, 1H), 6.42 (s, 1H), 6.22 (d, J=7.9 Hz, 1H), 4.25-4.04 (m, 1H), 3.84 (s, 3H), 2.81-2.62 (m, 2H), 2.13-1.79 (m, 2H), 1.31 (s, 3H), 1.28 (s, 3H).

Preparative Example 6: Preparation of 6-amino-7-methoxy-1,1-dimethyl-3,4-dihydronaphthalene-2(1H)-one

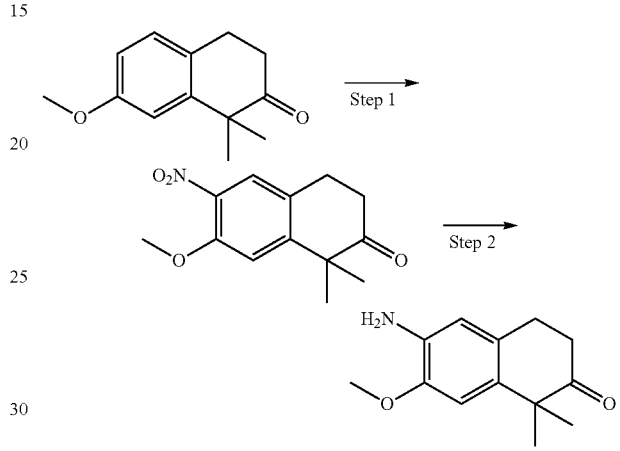

Step 1: Preparation of 7-methoxy-1,1-dimethyl-6-nitro-3,4-dihydronaphthalene-2(1H)-one 7-methoxy-1,1-dimethyl-3,4-dihydronaphthalene-2(1H)-one (0.1 g, 0.33 mmol) was dissolved in trifluoroacetic acid (3 mL), to which potassium nitrate was added at 0° C., followed by stirring at room temperature. Trifluoroacetic acid was concentrated under reduced pressure, diluted with ethylacetate, and washed with water. The organic layer was washed with brine, and dried over anhydrous magnesium sulfate to eliminate remaining moisture, followed by concentration. Then, purification was performed by silica gel column chromatography to give the target compound 7-methoxy-1,1-dimethyl-6-nitro-3,4-dihydronaphthalene-2(1H)-one.

Step 2: Preparation of 6-amino-7-methoxy-1,1-dimethyl-3,4-dihydronaphthalene-2(1H)-one 7-methoxy-1,1-dimethyl-6-nitro-3,4-dihydronaphthalene-2(1H)-one prepared in step 1 and 10 weight % palladium/charcoal (Pd/C) were hydrogenated in the presence of methanol solvent. Upon completion of the reaction, the reactant was filtered with celite and then washed with ethylacetate. The filtered organic solvent was concentrated under reduced pressure. As a result, the target compound 6-amino-7-methoxy-1,1-dimethyl-3,4-dihydronaphthalene-2(1H)-one was obtained.

$^1$H NMR (300 MHz, CDCl$_3$) δ 6.71 (s, 1H), 6.51 (s, 1H), 3.85 (s, 3H), 2.94 (t, J=6.84, 2H), 2.64 (t, J=6.84 Hz, 2H), 1.40 (s, 6H).

Preparative Example 7: Preparation of 7-amino-6-methoxy-1,1-dimethyl-3,4-dihydronaphthalene-2 (1H)-one

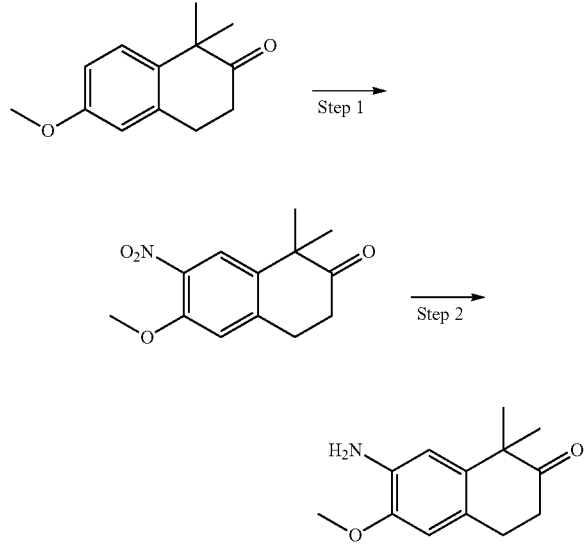 [SMILES: COc1ccc2c(c1)CCC(=O)C2(C)C ; COc1cc2c(cc1[N+](=O)[O-])C(C)(C)C(=O)CC2 ; COc1cc2c(cc1N)C(C)(C)C(=O)CC2]

Step 1: Preparation of 6-methoxy-1,1-dimethyl-7-nitro-3,4-dihydronaphthalene-2(1H)-one 6-methoxy-1,1-dimethyl-3,4-dihydronaphthalene-2(1H)-one (0.1 g, 0.33 mmol) was dissolved in trifluoroacetic acid (3 mL), to which potassium nitrate was added at 0° C., followed by stirring at room temperature. Trifluoroacetic acid was concentrated under reduced pressure, diluted with ethylacetate, and washed with water. The organic layer was washed with brine, and dried over anhydrous magnesium sulfate to eliminate remaining moisture, followed by concentration. Then, purification was performed by silica gel column chromatography to give the target compound 6-methoxy-1,1-dimethyl-7-nitro-3,4-dihydronaphthalene-2(1H)-one (0.05 g, 42%).

$^1$H NMR (300 MHz, CDCl$_3$) δ 7.86 (s, 1H), 6.88 (s, 1H), 3.96 (s, 3H), 3.14 (m, J=6.75, 2H), 2.70 (t, J=6.75, 2H), 1.44 (s, 6H)

Step 2: Preparation of 7-amino-6-methoxy-1,1-dimethyl-3,4-dihydronaphthalene-2(1H)-one 6-methoxy-1,1-dimethyl-7-nitro-3,4-dihydronaphthalene-2(1H)-one prepared in step 1 and 10 weight % palladium/charcoal (Pd/C) were hydrogenated in the presence of methanol solvent. Upon completion of the reaction, the reactant was filtered with celite and then washed with ethylacetate. The filtered organic solvent was concentrated under reduced pressure. As a result, the target compound 7-amino-6-methoxy-1,1-dimethyl-3,4-dihydronaphthalene-2(1H)-one was obtained.

$^1$H NMR (300 MHz, CDCl$_3$) δ 6.67 (s, 1H), 6.56 (s, 1H), 3.85 (s, 3H), 2.98 (t, J=6.6, 2H), 2.65 (t, J=6.6, 2H), 1.37 (s, 6H).

Example 1: Preparation of 5-chloro-N4-(2-(isopropylsulfonyl)phenyl)-N2-(3-methoxy-6-morpholino-5,6,7,8-tetrahydronaphthalene-2-yl)pyrimidine-2,4-diamine

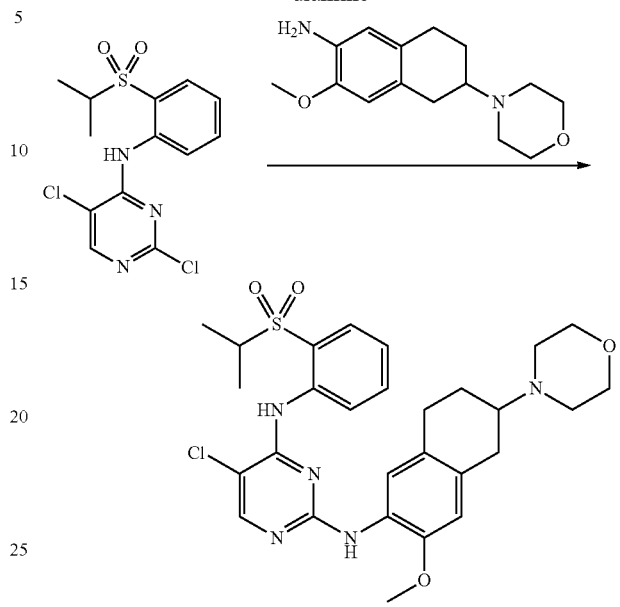

2,5-dichloro-N-(2-(isopropylsulfonyl)phenyl)pyrimidine-4-amine (1.2 eq) and the compound (1 eq) of preparative example 1 as an intermediate amine among the compounds of preparative examples were dissolved in ethoxy ethanol solution containing 0.08 M HCl dissolved therein, followed by heating at 100° C. The reaction was terminated by using sodium bicarbonate aqueous solution, followed by extraction with ethylacetate. The extracted organic layer was washed with brine, and dried over anhydrous magnesium sulfate to eliminate remaining moisture, followed by concentration. Then, purification was performed by silica gel column chromatography to give the target compound 5-chloro-N4-(2-(isopropylsulfonyl)phenyl)-N2-(3-methoxy-6-morpholino-5,6,7,8-tetrahydronaphthalene-2-yl)pyrimidine-2,4-diamine.

$^1$H NMR (300 MHz, CDCl$_3$) δ 7.51 (d, J=2.67 Hz, 1H), 7.34 (d, J=2.61 Hz, 1H), 7.16-7.14 (m, 2H), 7.08-7.06 (m, 2H), 6.89-6.86 (m, 1H), 4.31-4.22 (m, 5H), 3.82 (s, 3H), 3.59-3.54 (m, 1H), 2.98-2.94 (m, 1H), 2.75-2.70 (m, 3H), 2.56-2.51 (m, 3H), 2.36-2.34 (m, 3H), 2.34-2.30 (m, 1H), 1.37-1.26 (m, 6H)

Example 2: Preparation of 5-chloro-N4-(2-(isopropylsulfonyl)phenyl)-N2-(3-methoxy-6-(piperazine-1-yl)-5,6,7,8-tetrahydronaphthalene-2-yl)pyrimidine-2,4-diamine

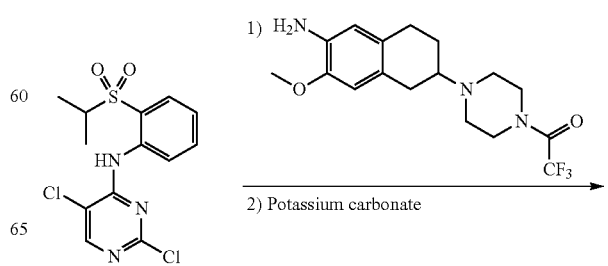

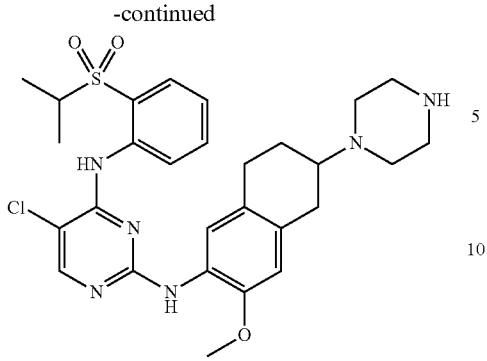
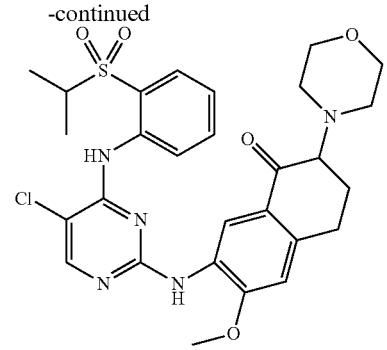

2,5-dichloro-N-(2-(isopropylsulfonyl)phenyl)pyrimidine-4-amine (1.2 eq) and the compound (1 eq) of preparative example 2 as an intermediate amine among the compounds of preparative examples were dissolved in ethoxy ethanol solution containing 0.08 M HCl dissolved therein, followed by heating at 100° C. The reaction was terminated by using sodium bicarbonate aqueous solution, followed by extraction with ethylacetate. The extracted organic layer was washed with brine, and dried over anhydrous magnesium sulfate to eliminate remaining moisture, followed by concentration. The compound obtained by purification with silica gel column chromatography was dissolved in methanol (3 mL), to which water (0.3 mL) and potassium carbonate (0.058 g, 0.184 mmol) were added, followed by stirring at 110° C. Upon completion of the reaction, the reaction solution was concentrated under reduced pressure, diluted with ethylacetate, and washed with water and brine. The organic layer was dried over anhydrous magnesium sulfate to eliminate remaining moisture, followed by concentration. Then, purification was performed by silica gel column chromatography to give the target compound 5-chloro-N4-(2-(isopropylsulfonyl)phenyl)-N2-(3-methoxy-6-(piperazine-1-yl)-5,6,7,8-tetrahydronaphthalene-2-yl)pyrimidine-2,4-diamine.

$^1$H NMR (300 MHz, CDCl$_3$) δ 9.50 (s, 1H), 8.55 (d, J=9.6, 1H), 8.15-8.14 (m, 1H), 7.94-7.90 (m, 1H), 7.59 (m, 1H), 7.59 (m, 1H), 7.49 (s, 1H), 6.57 (s, 1H), 3.85 (s, 3H), 3.72-3.60 (m, 4H), 3.55-3.53 (m, 1H), 3.25-3.24 (m, 1H), 2.86-2.70 (m, 7H), 2.09-2.03 (m, 1H), 1.64-1.57 (m, 1H), 1.38-1.19 (m, 6H).

Example 3: Preparation of 7-(5-chloro-4-(2-(isopropylsulfonyl)phenylamino)pyrimidine-2-ylamino)6-methoxy-2-morpholino-3,4-dihydronaphthalene-1(2H)-one

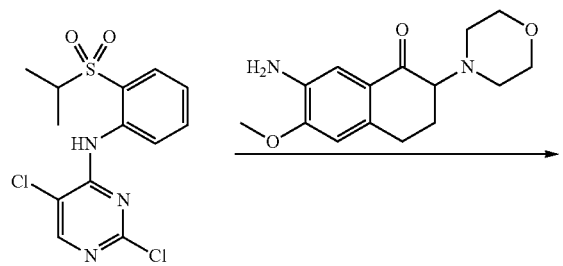

The target compound was synthesized by the same manner as described in example 1 except that 2,5-dichloro-N-(2-(isopropylsulfonyl)phenyl)pyrimidine-4-amine and the compound of preparative example 3 as an intermediate amine among the compounds of preparative examples were used.

$^1$H NMR (300 MHz, CDCl$_3$) δ 9.64 (s, 1H), 8.92 (s, 1H), 8.67 (d, J=9 Hz, 1H), 8.27 (s, 1H), 7.90 (d, J=9 Hz, 1H), 7.79 (s, 1H), 7.58-7.54 (m, 1H), 7.08 (s, 1H), 4.13-3.88 (m, 6H), 3.26-3.24 (m, 1H), 2.94 (s, 3H), 1.35-1.20 (m, 6H)

Example 4: Preparation of N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2,2,2-trifluoroacetamide

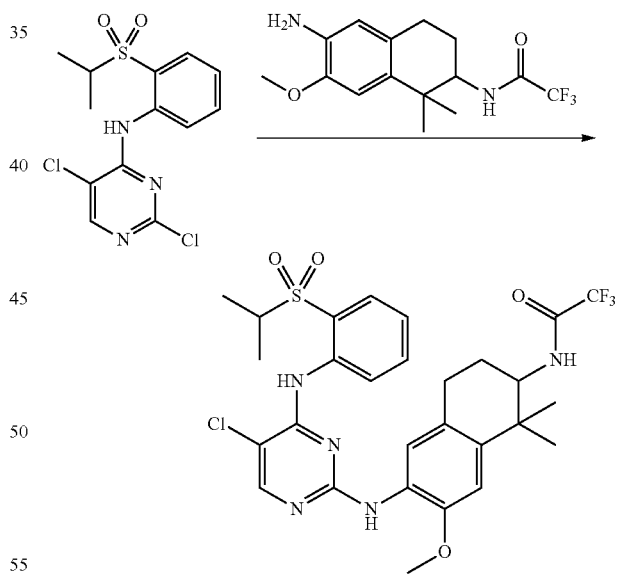

The target compound was synthesized by the same manner as described in example 1 except that 2,5-dichloro-N-(2-(isopropylsulfonyl)phenyl)pyrimidine-4-amine and the compound of preparative example 4 as an intermediate amine among the compounds of preparative examples were used.

$^1$H NMR (300 MHz, CDCl$_3$) δ 9.52 (s, 1H), 8.54 (d, J=8.3 Hz, 1H), 8.17 (s, 1H), 8.01-7.88 (m, 2H), 7.64 (t, J=7.9 Hz, 1H), 7.56 (s, 1H), 7.34-7.25 (m, 1H), 6.79 (s, 1H), 6.23 (d, J=9.3 Hz, 1H), 4.21 (t, J=7.3 Hz, 1H), 3.90 (s, 3H), 3.83-

3.48 (m, 1H), 3.29-3.21 (m, 1H), 2.80-2.55 (m, 2H), 2.15-1.85 (m, 2H), 1.47-1.14 (m, 12H)

Example 5: Preparation of 6-(5-chloro-4-(2-(isopropylsulfonyl)phenylamino)pyrimidine-2-ylamino)-7-methoxy-1,1-dimethyl-3,4-dihydronaphthalene-2(1H)-one

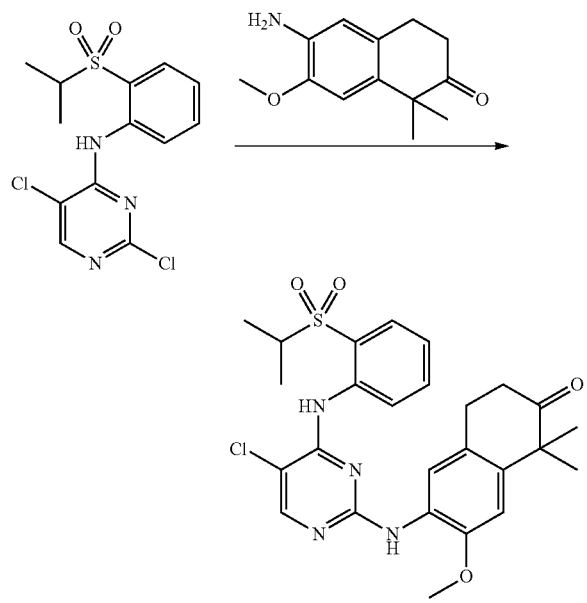

The target compound was synthesized by the same manner as described in example 1 except that 2,5-dichloro-N-(2-(isopropylsulfonyl)phenyl)pyrimidine-4-amine and the compound of preparative example 5 as an intermediate amine among the compounds of preparative examples were used.

$^1$H NMR (300 MHz, CDCl$_3$) δ 9.54 (s, 1H), 8.56 (d, J=8.4 Hz, 1H), 8.18 (s, 1H), 8.07 (s, 1H), 7.93 (d, J=7.8 Hz, 1H), 7.65-7.57 (m, 2H), 7.36 (t, J=7.65 Hz, 1H), 6.82 (s, 1H), 3.91 (s, 3H), 3.26 (sept, 1H, J=6.9 Hz, 1H), 2.92 (t, J=6.6 Hz, 2H), 2.66 (t, J=6.6 Hz, 2H), 1.44 (s, 6H), 1.32 (d, J=6.0 Hz, 6H)

Example 6: Preparation of 7-(5-chloro-4-(2-(isopropylsulfonyl)phenylamino)pyrimidine-2-ylamino)-6-methoxy-1,1-dimethyl-3,4-dihydronaphthalene-2(1H)-one

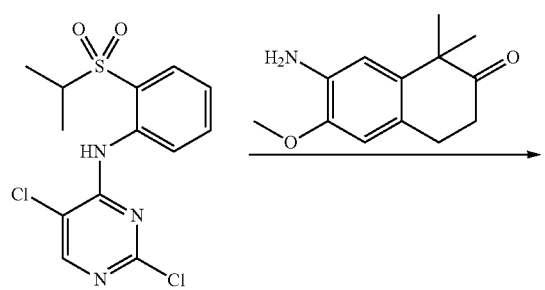

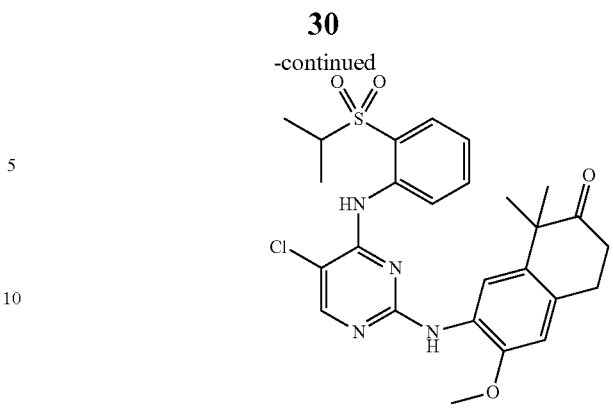

The target compound was synthesized by the same manner as described in example 1 except that 2,5-dichloro-N-(2-(isopropylsulfonyl)phenyl)pyrimidine-4-amine and the compound of preparative example 6 as an intermediate amine among the compounds of preparative examples were used.

$^1$H NMR (300 MHz, CDCl$_3$) δ 9.47 (s, 1H), 8.43 (d, J=8.4 Hz, 1H), 8.24 (s, 1H), 8.19 (s, 1H), 7.92 (d, J=8.1 Hz, 1H), 7.58 (t, J=7.8 Hz, 1H), 7.49 (s, 1H), 7.26 (t, J=7.8 Hz, 1H), 6.67 (s, 1H), 3.90 (s, 3H), 3.26 (sept, J=6.9 Hz, 1H), 3.04 (t, J=6.6 Hz, 2H), 2.66 (t, J=6.6 Hz, 2H), 1.31 (d, J=6.6 Hz, 6H), 1.22 (s, 6H)

Example 7: Preparation of N-(7-(5-chloro-4-(2-(isopropylsulfonyl)phenylamino)pyrimidine-2-ylamino)-6-methoxy-1,1-dimethyl-1,2,3,4-tetrahydronaphthalene-2-yl)-2,2,2-trifluoroacetamide

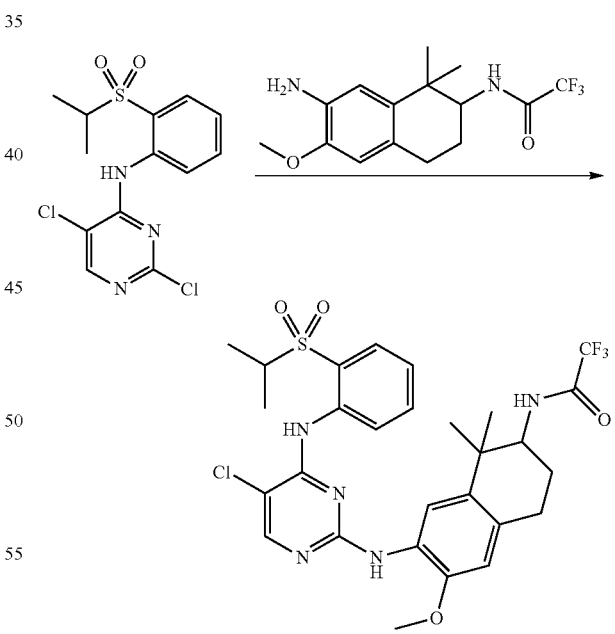

The target compound was synthesized by the same manner as described in example 1 except that 2,5-dichloro-N-(2-(isopropylsulfonyl)phenyl)pyrimidine-4-amine and the compound of preparative example 7 as an intermediate amine among the compounds of preparative examples were used.

$^1$H NMR (300 MHz, CDCl$_3$) δ 9.49 (s, 1H), 8.46 (d, J=8.4 Hz, 1H), 8.25 (s, 1H), 8.19 (s, 1H), 7.93-7.88 (m, 1H), 7.68-7.57 (m, 1H), 7.46 (s, 1H), 7.23 7.21 (m, 1H), 6.56 (s, 1H), 6.15 (d, J=9.6 Hz, 1H), 4.18-4.10 (m, 1H), 3.92 (s, 3H), 3.26 (sept, J=6.9 Hz, 1H), 2.93-2.77 (m, 2H), 2.12-2.04 (m, 1H), 1.99 1.90 (m, 1H), 1.31 (d, J=6.6, 6H), 1.22 (s, 6H)

LC/MS (ESI) m/z [M+H]$^+$ 626.2

Example 8: Preparation of (E)-6-(5-chloro-4-(2-(isopropylsulfonyl)phenylamino)pyrimidine-2-ylamino)-7-methoxy-1,1-dimethyl-3,4-dihydronaphthalene-2(1H)-one oxime

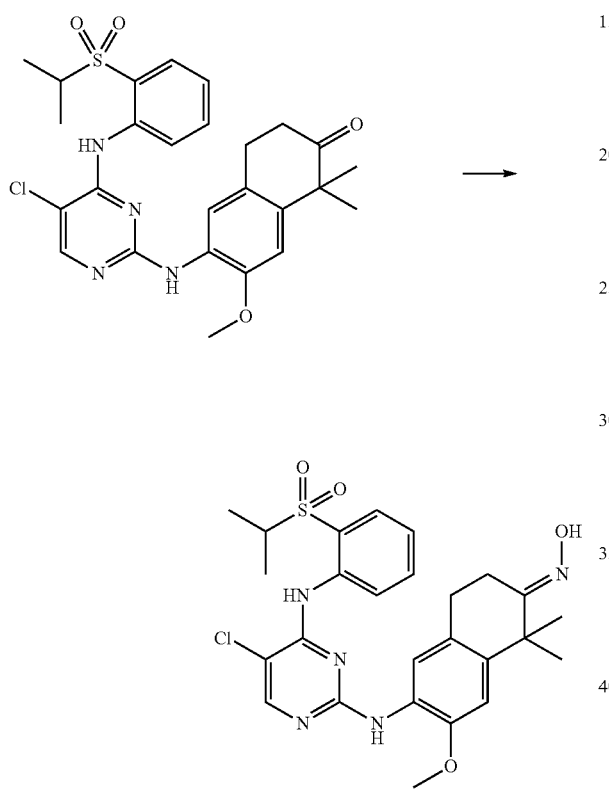

6-(5-chloro-4-(2-(isopropylsulfonyl)phenylamino)pyrimidine-2-ylamino)-7-methoxy-1,1-dimethyl-3,4-dihydronaphthalene-2(1H)-one (0.365 g, 0.69 mmol) was dissolved in methanol, to which water (3 mL), hydroxylamine hydrochloride (0.144 g, 2.07 mmol), and sodium acetate (0.17 g, 2.07 mmol) were added, followed by stirring at 90° C. Upon completion of the reaction, the reaction solution was concentrated under reduced pressure, and diluted with ethylacetate, followed by washing with water. The organic layer was dried over anhydrous magnesium sulfate to eliminate remaining moisture, followed by concentration. Then, purification was performed by silica gel column chromatography to give the target compound (E)-6-(5-chloro-4-(2-(isopropylsulfonyl)phenylamino)pyrimidine-2-ylamino)-7-methoxy-1,1-dimethyl-3,4-dihydronaphthalene-2(1H)-one oxime (0.215 g, 57%).

$^1$H NMR (300 MHz, CDCl$_3$) δ 9.54 (s, 1H), 8.56 (d, J=8.4 Hz, 1H), 8.18 (s, 1H), 8.07 (s, 1H), 7.93 (d, J=7.8 Hz, 1H), 7.65-7.57 (m, 2H), 7.36 (t, J=7.65, 1H), 6.82 (s, 1H), 3.91 (s, 3H), 3.26 (sept, J=6.9, 1H), 2.92 (t, J=6.6 Hz, 2H), 2.66 (t, J=6.6, 2H), 1.44 (s, 6H), 1.32 (d, J=6.0 Hz, 6H)

Example 9: Preparation of (E)-N-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)acetohydrazide

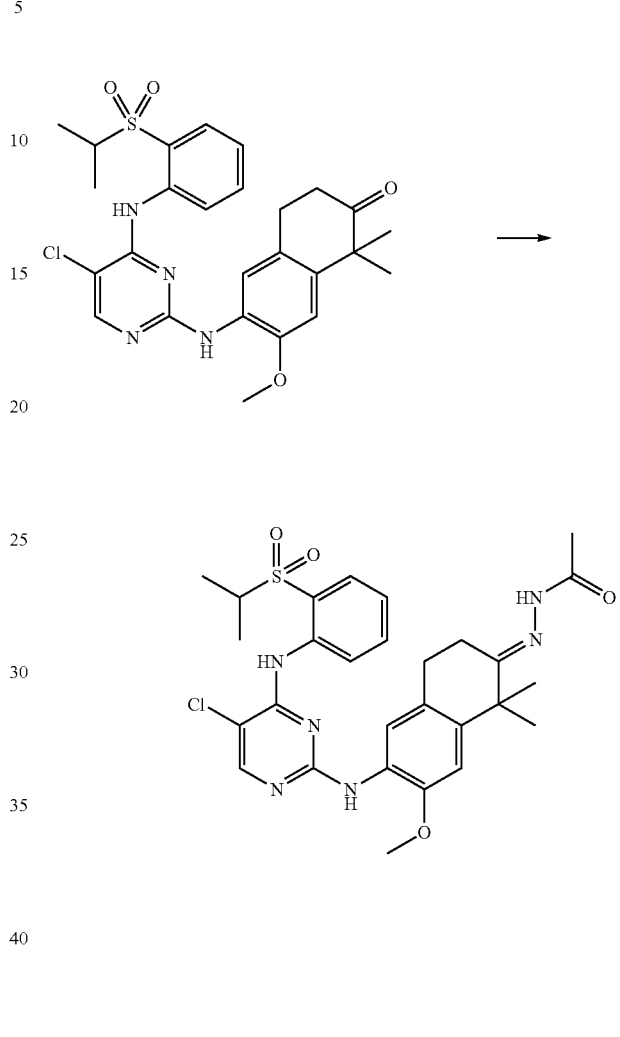

6-(5-chloro-4-(2-(isopropylsulfonyl)phenylamino)pyrimidine-2-ylamino)-7-methoxy-1,1-dimethyl-3,4-dihydronaphthalene-2(1H)-one (0.03 g, 0.057 mmol) was dissolved in ethanol, to which acetylhydrazide (0.013 g, 0.17 mmol) and concentrated sulfuric acid (catalytic amount) were added, followed by stirring at 80° C. for 18 hours. Upon completion of the reaction, the reaction solution was diluted with ethylacetate, followed by washing with water and brine. The organic layer was dried over anhydrous magnesium sulfate to eliminate remaining moisture, followed by concentration. Then, purification was performed by silica gel column chromatography to give the target compound (E)-N-6-(5-chloro-4-(2-(isopropylsulfonyl)phenylamino)pyrimidine-2-ylamino)-7-methoxy-1,1-dimethyl-3,4-dihydronaphthalene-2(1H)-one (0.0073 g, 22%).

$^1$H NMR (300 MHz, CDCl3) δ 9.55 (s, 1H), 8.57 (d, J=8.4 Hz, 1H), 8.42 (s, 1H), 8.17 (s, 1H), 8.06 (s, 1H), 7.95 (d, J=8.0 Hz, 1H), 7.69-7.48 (m, 2H), 7.34-7.28 (m, J=7.8 Hz, 1H), 6.91 (s, 1H), 3.92 (s, 3H), 3.35-3.19 (m, 1H), 2.92-2.78 (m, 2H), 2.52 (t, J=6.5 Hz, 2H), 2.31 (s, 3H), 1.51 (s, 5H), 1.33 (d, J=6.8 Hz, 6H).

Example 10: Preparation of (E)-2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrogencarboxamide

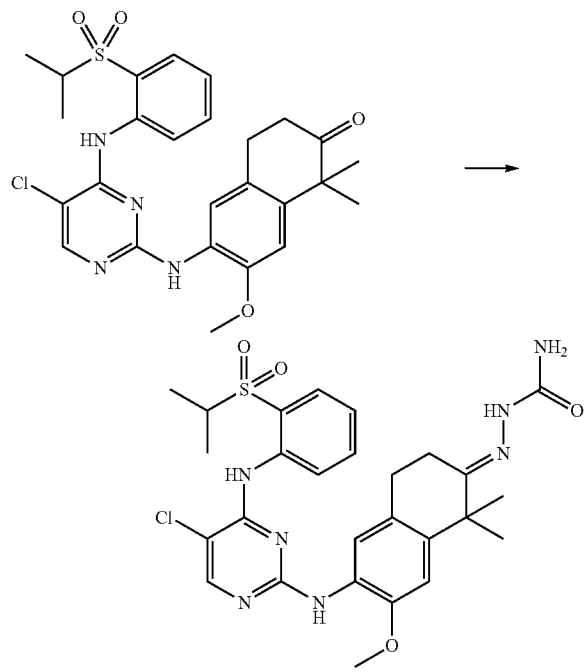

The target compound was synthesized by the same manner as described in example 9 except that 6-(5-chloro-4-(2-(isopropylsulfonyl)phenylamino)pyrimidine-2-ylamino)-7-methoxy-1,1-dimethyl-3,4-dihydronaphthalene-2(1H)-one and semicarbazide hydrochloride as an intermediate amine were used.

$^1$H NMR (300 MHz, CDCl$_3$) δ 9.55 (s, 1H), 8.57 (d, J=8.4 Hz, 1H), 8.17 (s, 1H), 8.06 (s, 1H), 7.95 (d, J=7.8 Hz, 1H), 7.86 (s, 1H), 7.61 (d, J=7.7 Hz, 1H), 7.56 (s, 1H), 7.35-7.28 (m, 1H), 6.90 (s, 1H), 6.35-5.91 (br, 1H), 5.13-4.60 (br, 1H), 4.37-4.21 (m, J=6.3 Hz, 1H), 3.92 (s, 3H), 3.35-3.19 (m, 1H), 2.94-2.77 (m, 2H), 2.63-2.48 (m, 2H), 1.51 (s, 6H), 1.31 (d, J=9.5 Hz, 6H)

Example 11: Preparation of (E)-2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrogencarboxamideamide

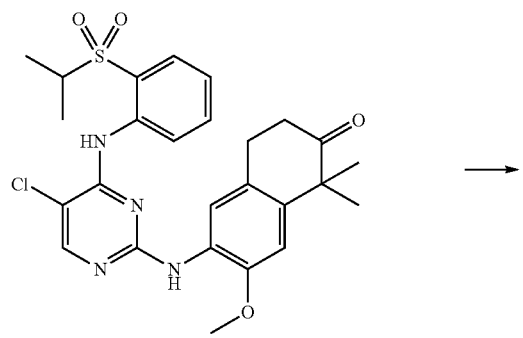

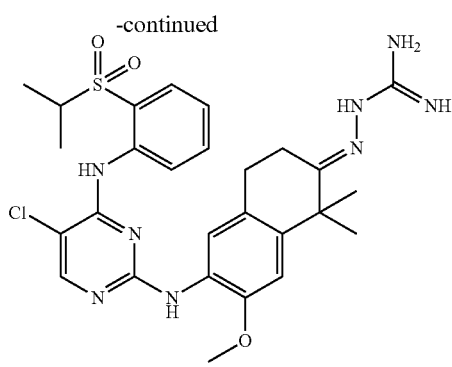

The target compound was synthesized by the same manner as described in example 9 except that 6-(5-chloro-4-(2-(isopropylsulfonyl)phenylamino)pyrimidine-2-ylamino)-7-methoxy-1,1-dimethyl-3,4-dihydronaphthalene-2(1H)-one and aminoguanidine hydrochloride as an intermediate amine were used.

$^1$H NMR (300 MHz, CDCl$_3$) δ 10.16 (s, 1H), 9.52 (s, 1H), 8.52 (d, J=8.1 Hz, 1H), 8.15 (s, 1H), 8.03 (s, 1H), 7.93 (d, J=7.6 Hz, 2H), 7.65 (t, J=7.8 Hz, 1H), 7.55 (s, 1H), 7.42 (s, 1H), 7.35 (t, J=7.9 Hz, 1H), 6.86 (s, 1H), 6.37 (s, 1H), 4.27-4.03 (m, 2H), 3.91 (s, 3H), 3.38-3.16 (m, 1H), 2.93-2.65 (m, 2H), 1.49 (s, 6H), 1.42-1.20 (m, 6H)

Example 12: Preparation of (E)-tert-뷰 2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrazinecarboxylate

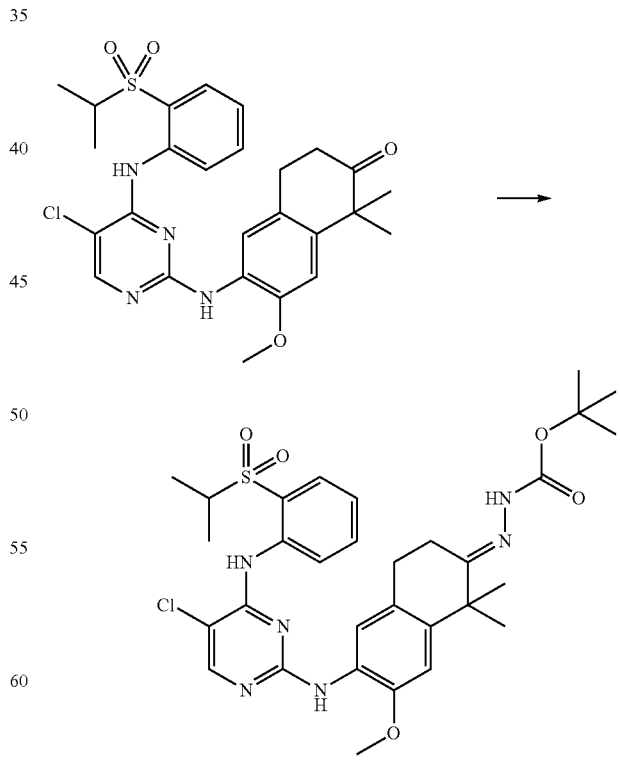

The target compound was synthesized by the same manner as described in example 9 except that 6-(5-chloro-4-(2-(isopropylsulfonyl)phenylamino)pyrimidine-2-ylamino)-7- methoxy-1,1-dimethyl-3,4-dihydronaphthalene-2(1H)-one and tert-butyl carbazate as an intermediate amine were used.

$^1$H NMR (300 MHz, CDCl$_3$) δ 9.52 (s, 1H), 8.56 (d, J=8.1 Hz, 1H), 8.16 (s, 1H), 8.03 (s, 1H), 7.9 (d, J=7.8 Hz, 1H), 7.62-7.51 (m, 3H), 7.29-7.25 (m, 1H), 6.92 (s, 1H), 3.91 (s, 3H), 3.26 (sept, J=6.9 Hz, 1H), 2.83 (t, J=6.6 Hz, 2H), 2.51 (t, J=6.6 Hz, 2H), 1.55 (s, 9H), 1.52 (s, 6H), 1.32 (d, J=6.6 Hz, 9H)

Example 13: Preparation of (E)-5-chloro-N2-(6-hydrazono-3-methoxy-5,5-dimethyl-5,6,7,8-tetrahydronaphthalene-2-yl)-N4-(2-(isopropylsulfonyl)phenyl)pyrimidine-2,4-diamine hydrochloride

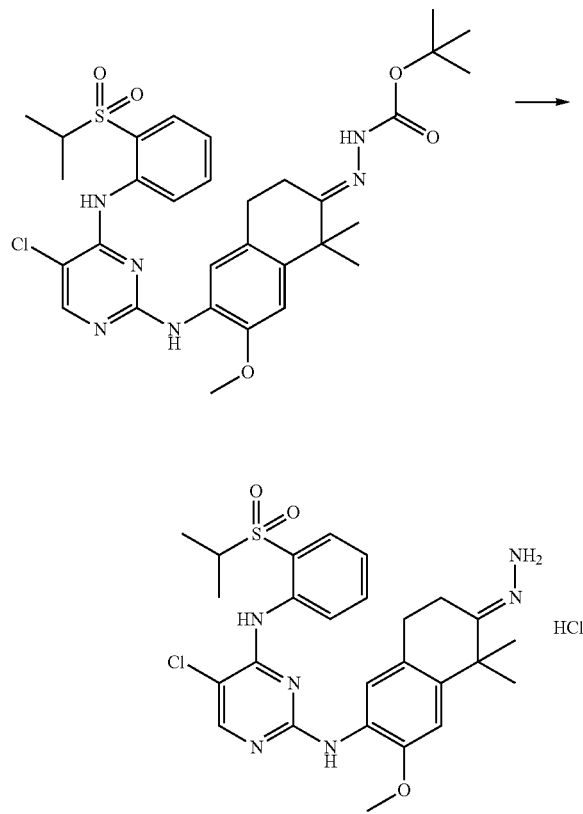

Tert-butyl 2-(6-(5-chloro-4-(2-(isopropylsulfonyl)phenylamino)pyrimidine-2-ylamino)-7-methoxy-1,1-dimethyl-3,4-dihydronaphthalene-2(1H)-one(1H)-yladene)hydrazinecarboxylate was dissolved in dichloromethane, to which 4 M HCl/dioxane solution was added, followed by stirring at room temperature. Upon completion of the reaction, the reaction solution was concentrated. As a result, the target compound (E)-5-chloro-N2-(6-hydrazono-3-methoxy-5,5-dimethyl-5,6,7,8-tetrahydronaphthalene-2-yl)-N4-(2-(isopropylsulfonyl)phenyl)pyrimidine-2,4-diamine hydrochloride was obtained.

$^1$H NMR (300 MHz, CDCl$_3$) δ 9.52 (s, 1H), 8.58 (d, J=8.4 Hz, 1H), 8.16 (s, 1H), 8.03 (s, 1H), 7.94 (d, J=7.8 Hz, 1H), 7.65 (t, J=7.6 Hz, 1H), 7.54 (s, 1H), 7.29 (t, J=7.6 Hz, 1H), 6.97 (s, 1H), 4.96 (s, 2H), 3.91 (s, 3H), 3.28-3.21 (m, 1H), 2.86 (t, J=6.7 Hz, 2H), 2.53 (t, J=6.7 Hz, 1H), 1.47 (s, 6H), 1.33 (d, J=6.9 Hz, 6H)

Example 14: Preparation of (E)-5-chloro-N4-(2-(isopropylsulfonyl)phenyl)-N2-(3-methoxy-5,5-dimethyl-6-(4-methylpiperazine-1-ylimino)-5,6,7,8-tetrahydronaphthalene-2-yl)pyrimidine-2,4-diamine

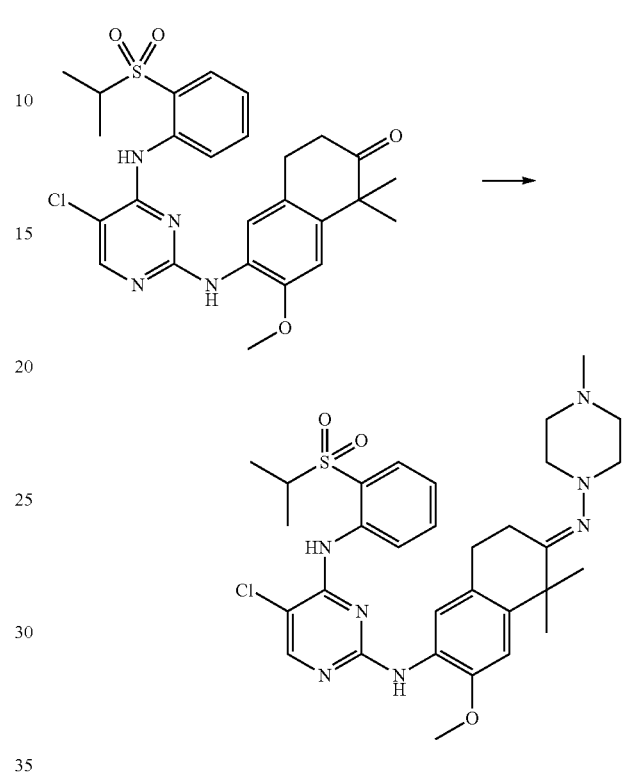

The target compound was synthesized by the same manner as described in example 9 except that 6-(5-chloro-4-(2-(isopropylsulfonyl)phenylamino)pyrimidine-2-ylamino)-7-methoxy-1,1-dimethyl-3,4-dihydronaphthalene-2(1H)-one and 1-amino-4-methylpiperazine as an intermediate amine were used.

$^1$H NMR (300 MHz, CDCl$_3$) δ 9.52 (s, 1H), 8.57 (d, J=8.1 Hz, 1H), 8.17 (s, 1H), 8.05-7.90 (m, 2H), 7.63 (t, J=7.2 Hz, 1H), 7.56 (s, 1H), 7.31 (s, 1H), 6.89 (s, 1H), 3.91 (s, 3H), 3.38-3.17 (m, 1H), 2.88-2.74 (m, 6H), 2.74-2.51 (m, 6H), 2.34 (s, 3H), 1.49 (s, 6H), 1.32 (d, J=6.8 Hz, 6H)

Example 15: Preparation of (E)-5-chloro-N4-(2-(isopropylsulfonyl)phenyl)-N2-(3-methoxy-5,5-dimethyl-6-(morpholinoimino)-5,6,7,8-tetrahydronaphthalene-2-yl)pyrimidine-2,4-diamine

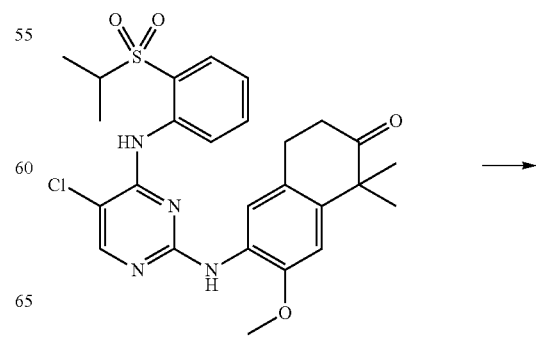

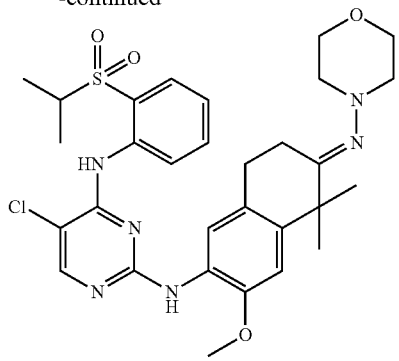

The target compound was synthesized by the same manner as described in example 9 except that 6-(5-chloro-4-(2-(isopropylsulfonyl)phenylamino)pyrimidine-2-ylamino)-7-methoxy-1,1-dimethyl-3,4-dihydronaphthalene-2(1H)-one and 1-aminomorpholine as an intermediate amine were used.

$^1$H NMR (300 MHz, CDCl$_3$) δ 9.52 (s, 1H), 8.57 (d, J=8.1 Hz, 1H), 8.16 (s, 1H), 7.98 (s, 1H), 7.93 (d, J=6.7 Hz, 1H), 7.63 (t, J=7.1 Hz, 1H), 7.56 (s, 1H), 7.34-7.27 (m, 1H), 6.89 (s, 1H), 3.91 (s, 3H), 3.88-3.77 (m, 4H), 3.39-3.16 (m, 1H), 2.90-2.77 (m, 2H), 2.77-2.59 (m, 6H), 1.55 (s, 6H), 1.32 (d, J=6.8 Hz, 6H).

Example 16: Preparation of (E)-7-(5-chloro-4-(2-(isopropylsulfonyl)phenylamino)pyrimidine-2-ylamino)-6-methoxy-1,1-dimethyl-3,4-dihydronaphthalene-2(1H)-one oxime

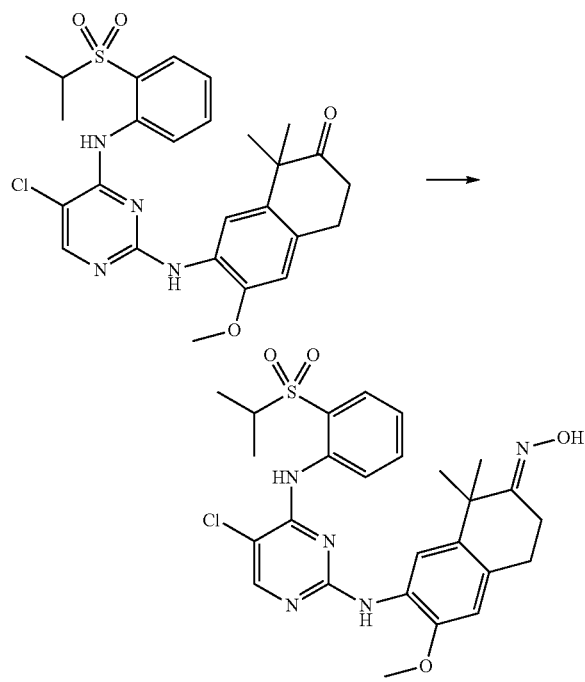

The target compound was synthesized by the same manner as described in example 1 except that 7-(5-chloro-4-(1-isopropylsulfonyl)phenylamino)pyrimidine-2-ylamino)-6-methoxy-1,1-dimethyl-3,4-dihydronaphthalene-2(1H)-one and the compound of preparative example 1 as an intermediate amine among the compounds of preparative examples were used.

$^1$H NMR (300 MHz, CDCl$_3$) δ 9.49 (s, 1H), 8.40 (d, J=8.1 Hz, 1H), 8.16 (s, 1H), 7.89 (d, J=7.8 Hz, 1H), 7.58-7.50 (m, 2H), 7.21 (t, J=7.8, 1H), 6.65 (s, 1H), 3.87 (s, 3H), 3.26 (sept, J=6.9, 1H), (dd, J=5.1, 4H) 1.32-1.28 (m, 12H)

Example 17: Preparation of (E)-5-chloro-N4-(2-(isopropylsulfonyl)phenyl)-N2-(3-methoxy-8,8-dimethyl-7-(morpholinoimino)-5,6,7,8-tetrahydronaphthalene-2-yl)pyrimidine-2,4-diamine

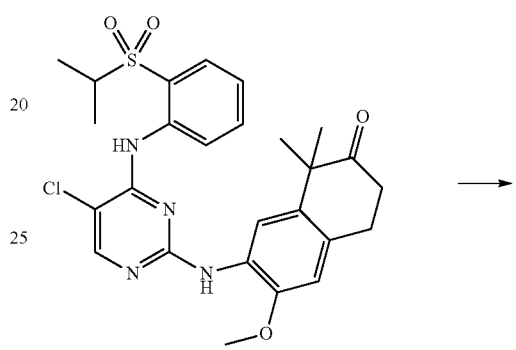

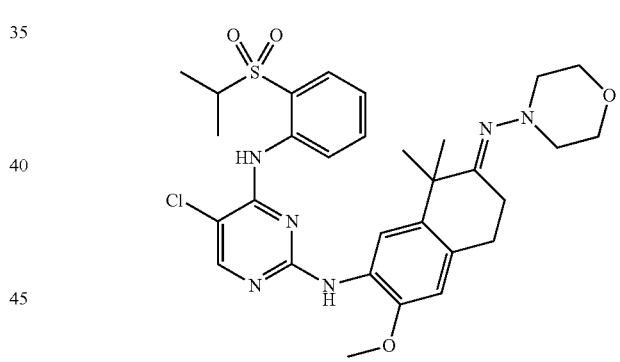

The target compound was synthesized by the same manner as described in example 15 except that 7-(5-chloro-4-(1-isopropylsulfonyl)phenylamino)pyrimidine-2-ylamino)-6-methoxy-1,1-dimethyl-3,4-dihydronaphthalene-2(1H)-one and 1-aminomorpholine as an intermediate amine were used.

$^1$H NMR (300 MHz, CDCl$_3$) δ 9.45 (s, 1H), 8.43 (d, J=8.4 Hz, 1H), 8.23 (s, 1H), 8.19 (s, 1H), 7.91 (dd, J=7.8, 1.2 Hz, 1H), 7.58 (t, J=7.5 Hz, 1H), 7.26 (t, J=7.5 Hz, 1H), 6.60 (s, 1H), 3.87 (s, 3H), 3.85-3.80 (m, 4H), 3.26 (sept, J=6.9 Hz, 1H) 2.83 (s, 4H), 2.70-2.67 (m, 4H), 1.31 (d, J=6.9 Hz, 6H), 1.12 (d, J=9.9 Hz, 6H)

Example 18: Preparation of (E)-2-(7-(5-chloro-4-(2-(isopropylsulfonyl)phenylamino)pyrimidine-2-ylamino)-6-methoxy-1,1-dimethyl-3,4-dihydronaphthalene-2(1H)-yladene)hydrogencarboxamideamide

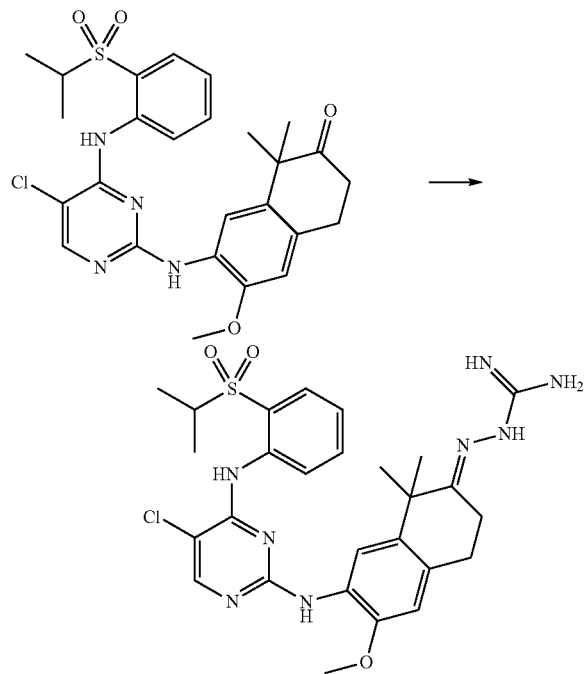

The target compound was synthesized by the same manner as described in example 11 except that 7-(5-chloro-4-(1-isopropylsulfonyl)phenylamino)pyrimidine-2-ylamino)-6-methoxy-1,1-dimethyl-3,4-dihydronaphthalene-2(1H)-one and aminoguanidine as an intermediate amine were used.

$^1$H NMR (300 MHz, CDCl$_3$) δ 9.51 (s, 1H), 8.47 (d, J=7.8 Hz, 1H), 8.26 (s, 1H), 8.18 (s, 1H), 7.91 (dd, J=7.8, 1.2 Hz, 1H), 7.72 (s, 2H), 7.56 (t, J=7.8 Hz, 1H), 7.43 (s, 1H), 7.22 (t, J=7.8 Hz, 1H), 6.64 (s, 1H), 3.88 (s, 3H), 3.26 (sept, J=6.9 Hz, 1H), 3.27 (t, J=6.45 Hz, 2H), 2.82 (t, J=6.45 Hz, 2H), 1.35-1.31 (m, 12H)

Example 19: Preparation of (E)-5-chloro-N4-(2-(isopropylsulfonyl)phenyl)-N2-(3-methoxy-8,8-dimethyl-7-(4-methylpiperazine-1-ylimino)-5,6,7,8-tetrahydronaphthalene-2-yl)pyrimidine-2,4-diamine

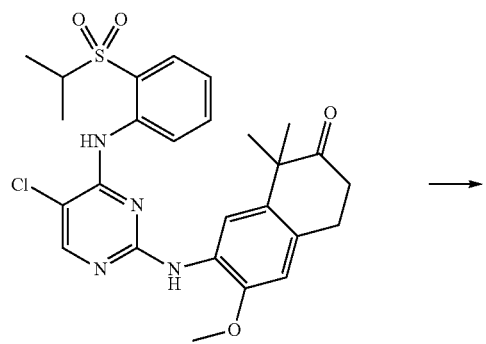

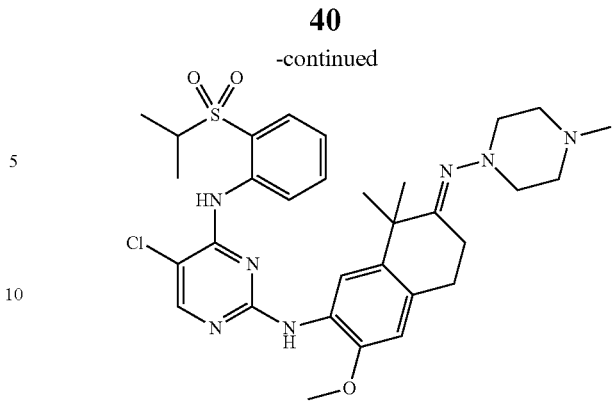

The target compound was synthesized by the same manner as described in example 14 except that 7-(5-chloro-4-(1-isopropylsulfonyl)phenylamino)pyrimidine-2-ylamino)-6-methoxy-1,1-dimethyl-3,4-dihydronaphthalene-2(1H)-one and 1-amino-4-methylpiperazine as an intermediate amine were used.

$^1$H NMR (300 MHz, CDCl$_3$) δ 9.44 (s, 1H), 8.43 (d, J=8.4 Hz, 1H), 8.22 (s, 1H), 8.18 (s, 1H), 7.91 (d, J=8.4 Hz, 1H), 7.57 (t, J=7.8 Hz, 1H), 7.43 (s, 1H), 7.23 (t, J=7.5 Hz, 1H), 6.60 (s, 1H), 3.87 (s, 3H), 3.26 (sept, J=6.9 Hz, 1H) 2.81 (s, 4H), 2.73-2.70 (m, 4H), 2.55 (s, 4H), 2.30 (s, 4H), 1.31 (d, J=6.6 Hz, 6H), 1.26 (s, 6H)

Example 20: Preparation of (E)-N-(7-(5-chloro-4-(2-(isopropylsulfonyl)phenylamino)pyrimidine-2-ylamino)-6-methoxy-1,1-dimethyl-3,4-dihydronaphthalene-2(1H)-yladene)acetohydrazide

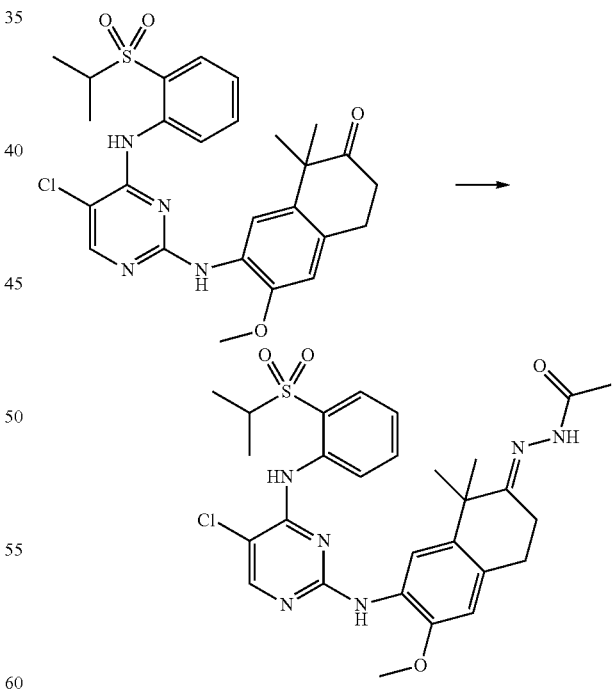

The target compound was synthesized by the same manner as described in example 14 except that 7-(5-chloro-4-(1-isopropylsulfonyl)phenylamino)pyrimidine-2-ylamino)-6-methoxy-1,1-dimethyl-3,4-dihydronaphthalene-2(1H)-one and 1-amino-4-methylpiperazine as an intermediate amine were used.

¹H NMR (300 MHz, CDCl₃) δ 9.46 (s, 1H), 8.99 (s, 1H), 8.44 (d, J=8.4 Hz, 1H), 8.28 (s, 1H), 8.19 (s, 1H), 7.91 (d, J=8.4 Hz, 1H), 7.58 (t, J=7.8 Hz, 1H), 7.47 (s, 1H), 7.23 (t, J=7.8 Hz, 1H), 7.12 (t, J=5.4 Hz, 1H), 6.61 (s, 1H), 3.87 (s, 3H), 3.26 (sept, J=6.9 Hz, 1H), 2.81 (t, J=6.6 Hz, 3H), 2.53 (t, J=6.6 Hz, 3H), 2.24 (s, 3H), 1.37-1.25 (m, 12H)

Example 21: Preparation of (E)-2-(7-(5-chloro-4-(2-(isopropylsulfonyl)phenylamino)pyrimidine-2-ylamino)-6-methoxy-1,1-dimethyl-3,4-dihydronaphthalene-2(1H)-yladene)hydragencarboxamide

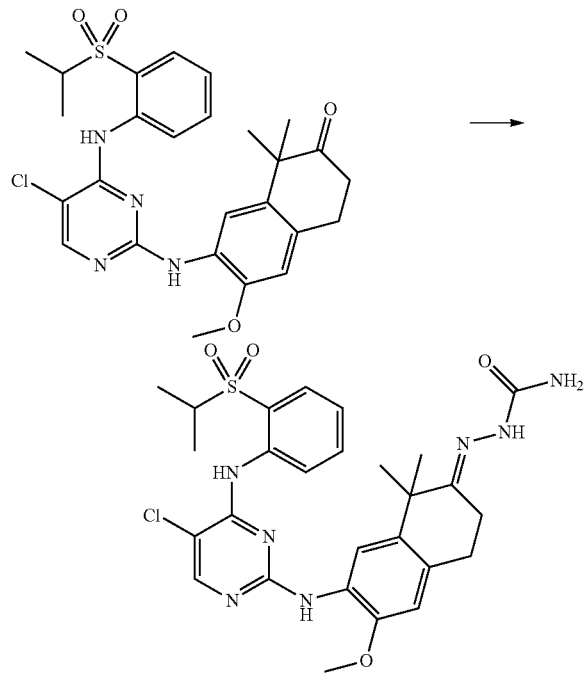

The target compound was synthesized by the same manner as described in example 14 except that 7-(5-chloro-4-(1-isopropylsulfonyl)phenylamino)pyrimidine-2-ylamino)-6-methoxy-1,1-dimethyl-3,4-dihydronaphthalene-2(1H)-one and 1-amino-4-methylpiperazine as an intermediate amine were used.

¹H NMR (300 MHz, CDCl₃) δ 9.50 (s, 1H), 8.45 (d, J=8.1, 1H), 8.23 (s, 1H), 8.18 (s, 1H), 7.91 (d, J=8.1, 1H), 7.85 (s, 1H), 7.53 (t, J=7.8, 1H), 7.43 (s, 1H), 7.25-7.06 (m, 2H), 6.67 (s, 1H), 3.88 (s, 3H), 3.26 (sept, J=6.9, 1H) 2.98 (t, J=6.35, 2H), 2.55 (t, J=6.35, 2H), 1.33-1.23 (m, 12H)

Example 22: Preparation of N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine

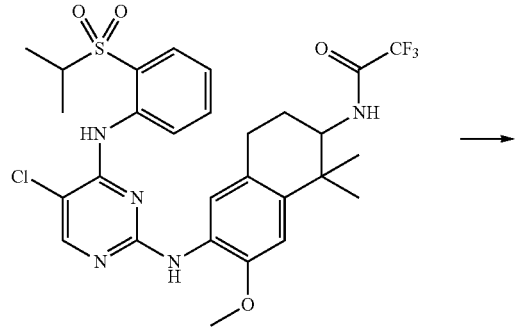

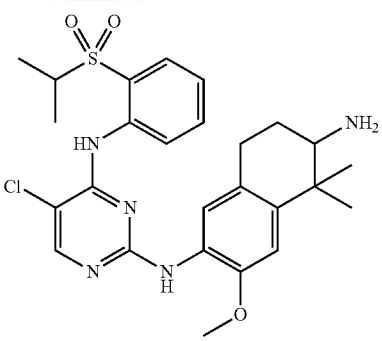

6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2,2,2-trifluoroacetamide (0.023 g, 0.037 mmol) was dissolved in methanol (3 mL), to which water (0.3 mL) and potassium carbonate (0.058 g, 0.184 mmol) were added, followed by stirring at 110° C. Upon completion of the reaction, the reaction solution was concentrated under reduced pressure, and diluted with ethylacetate, followed by washing with water and brine. The organic layer was dried over anhydrous magnesium sulfate to eliminate remaining moisture, followed by concentration. Then, purification was performed by silica gel column chromatography to give the target compound N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine.

¹H NMR (300 MHz, CDCl₃) δ 9.49 (s, 1H), 8.54 (d, J=8.3 Hz, 1H), 7.92 (dd, J=8.0, 1.4 Hz, 1H), 7.89 (s, 1H), 7.72-7.57 (m, 1H), 7.53 (s, 1H), 7.32-7.18 (m, 2H), 6.83 (s, 1H), 3.88 (s, 3H), 3.33-3.15 (m, 1H), 2.87 (dd, J=9.1, 2.8 Hz, 1H), 2.68 (t, J=6.6 Hz, 2H), 1.99-1.84 (m, 1H), 1.84-1.68 (m, 1H), 1.33 (d, J=4.9 Hz, 6H), 1.28 (s, 3H), 1.23 (s, 3H)

Example 23: Preparation of N2-(7-amino-3-methoxy-8,8-dimethyl-5,6,7,8-tetrahydronaphthalene-2-yl)-5-chloro-N4-(2-(isopropylsulfonyl)phenyl)pyrimidine-2,4-diamine

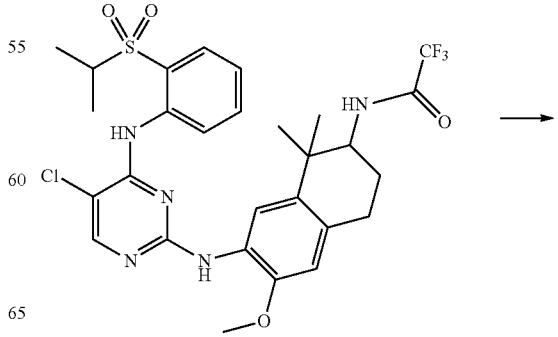

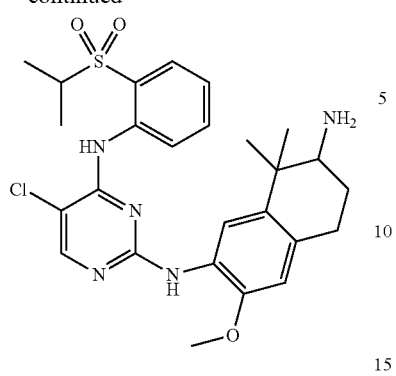

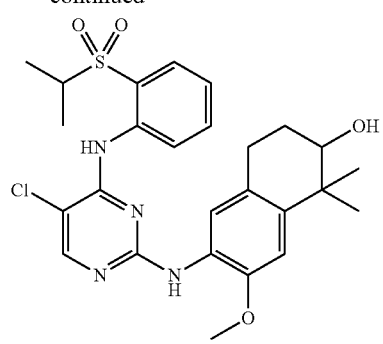

N-(7-(5-chloro-4-(2-(isopropylsulfonyl)phenylamino)pyrimidine-2-ylamino)-6-methoxy-1,1-dimethyl-1,2,3,4-tetrahydronaphthalene-2-yl)-2,2,2-trifluoroacetamide was dissolved in methanol (3 mL), to which water (0.3 mL) and potassium carbonate (0.058 g, 0.184 mmol) were added, followed by stirring at 110° C. Upon completion of the reaction, the reaction solution was concentrated under reduced pressure, and diluted with ethylacetate, followed by washing with water and brine. The organic layer was dried over anhydrous magnesium sulfate to eliminate remaining moisture, followed by concentration. Then, purification was performed by silica gel column chromatography to give the target compound N2-(7-amino-3-methoxy-8,8-dimethyl-5,6,7,8-tetrahydronaphthalene-2-yl)-5-chloro-N4-(2-(isopropylsulfonyl)phenyl)pyrimidine-2,4-diamine.

$^1$H NMR (300 MHz, CDCl$_3$) δ 9.44 (s, 1H), 8.45 (d, J=8.4 Hz, 1H), 8.23 (s, 1H), 8.18 (s, 1H), 7.90 (d, J=8.4 Hz, 1H), 7.59 (t, J=7.8, 1H), 7.42 (s, 1H), 7.22 (t, J=7.8, 1H), 6.54 (s, 1H), 3.85 (s, 3H), 3.26 (sept, J=6.9 Hz, 1H), 2.89-2.80 (m, 3H), 2.16-1.70 (m, 9H), 1.31 (d, J=6.6 Hz, 6H), 1.14 (s, 3H), 1.07 (s, 3H)

Example 24: Preparation of 6-(5-chloro-4-(2-(isopropylsulfonyl)phenylamino)pyrimidine-2-ylamino)-7-methoxy-1,1-dimethyl-1,2,3,4-tetrahydronaphthalene-2-ol 6-(5-chloro-4-(2-(isopropylsulfonyl)phenylamino)pyrimidine-2-ylamino)-7-methoxy-1,1-dimethyl-3,4-dihydronaphthalene-2(1H)-one(0.03 g, 0.57 mmol) was dissolved in tetrahydrofuran/methanol solution (1:1, 2 mL), to which sodium borohydride (0.0024 g, 0.063 mmol) was added at 0° C., followed by stirring at room temperature. Upon completion of the reaction, the reaction solution was diluted with ethylacetate and water. The organic layer was washed with brine and dried over anhydrous magnesium sulfate to eliminate remaining moisture, followed by concentration. Then, purification was performed by silica gel column chromatography to give the target compound 6-(5-chloro-4-(2-(isopropylsulfonyl)phenylamino)pyrimidine-2-ylamino)-7-methoxy-1,1-dimethyl-1,2,3,4-tetrahydronaphthalene-2-ol.

$^1$H NMR (300 MHz, CDCl$_3$) δ 9.49 (s, 1H), 8.54 (d, J=8.2 Hz, 1H), 8.14 (s, 1H), 7.98-7.84 (m, J=12.1 Hz, 2H), 7.64 (t, J=7.1 Hz, 1H), 7.55 (s, 1H), 7.32-7.21 (m, J=7.8 Hz, 1H), 6.82 (s, 1H), 3.88 (s, 3H), 3.75 (d, J=6.7 Hz, 1H), 3.34-3.17 (m, 1H), 2.80-2.58 (m, 2H), 2.03-1.86 (m, 2H), 1.81 (s, 1H), 1.41-1.27 (m, 12H)

Example 25: Preparation of 7-(5-chloro-4-(2-(isopropylsulfonyl)phenylamino)pyrimidine-2-ylamino)-6-methoxy-1,1-dimethyl-1,2,3,4-tetrahydronaphthalene-2-ol

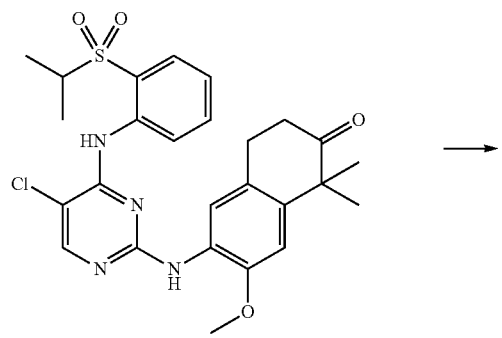

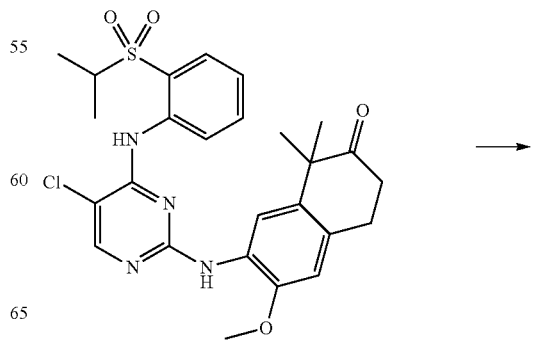

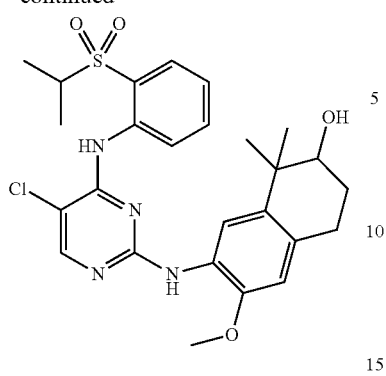
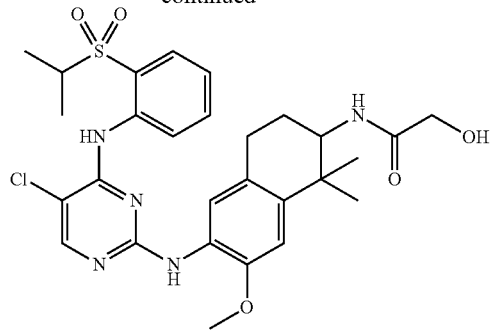

7-(5-chloro-4-(2-(isopropylsulfonyl)phenylamino)pyrimidine-2-ylamino)-6-methoxy-1,1-dimethyl-3,4-dihydronaphthalene-2(1H)-one (0.03 g, 0.57 mmol) was dissolved in tetrahydrofuran/methanol solution (1:1, 2 mL), to which sodium borohydride (0.0024 g, 0.063 mmol) was added at 0° C., followed by stirring at room temperature. Upon completion of the reaction, the reaction solution was diluted with ethylacetate and water. The organic layer was washed with brine and dried over anhydrous magnesium sulfate to eliminate remaining moisture, followed by concentration. Then, purification was performed by silica gel column chromatography to give the target compound 7-(5-chloro-4-(2-(isopropylsulfonyl)phenylamino)pyrimidine-2-ylamino)-6-methoxy-1,1-dimethyl-1,2,3,4-tetrahydronaphthalene-2-ol.

$^1$H NMR (300 MHz, CDCl$_3$) δ 9.43 (s, 1H), 8.44 (d, J=8.1 Hz, 1H), 8.18 (s, 1H), 7.91 (dd, J=8.1 Hz, 1.5, 1H), 7.60 (t, J=6.9 Hz, 1H), 7.44 (s, 1H), 7.22 (t, J=6.9 Hz, 1H), 6.55 (s, 1H), 3.85 (s, 3H), 3.69 (dd, J=8.4 Hz, 3, 1H), 3.26 (sept, J=6.9 Hz, 1H), 2.93-2.80 (m, 2H), 2.02-1.89 (m, 2H), 1.31 (d, J=6.9 Hz, 6H), 1.12 (d, J=9.9 Hz, 6H)

Example 26: Preparation of N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2-hydroxyacetamide N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine (50 mg, 0.09 mmol) was dissolved in dichloromethane (1 mL), to which glycolic acid (11 mg, 0.14 mmol), 1-ethyl-3-(3-dimethylaminopropyl)carbodiimideI (22 mg, 0.14 mmol), 1-hydroxybenzotriazol (19 mg, 0.14 mmol), and triethylamine (0.02 mL, 0.14 mmol) were added, followed by stirring at room temperature. The reaction solution was diluted with dichloromethane, followed by washing with water and brine. The organic layer was dried over anhydrous magnesium sulfate to eliminate remaining moisture, followed by concentration. Then, purification was performed by silica gel column chromatography to give the target compound N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2-hydroxyacetamide.

$^1$H NMR (CDCl$_3$, 300 MHz) δ 9.52 (s, 1H), 8.54 (d, J=8.4, 1H), 8.14 (s, 1H), 7.93 (s, 1H), 7.91 (s, 1H), 7.64 (d, J=7.8, 1H), 7.53 (s, 1H), 7.26 (t, J=7.65, 1H), 6.79 (s, 1H), 6.52 (d, J=9.6, 1H), 4.19 (s, 2H), 3.88 (s, 3H), 3.26 (sept, J=6.9, 1H), 2.78-2.63 (m, 3H), 2.12-2.00 (m, 2H), 1.90-1.83 (m, 1H), 1.32 (d, J=3.6, 6H), 1.26 (d, J=7.5, 6H).

Example 27: Preparation of N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2-(dimethylamino)acetamide

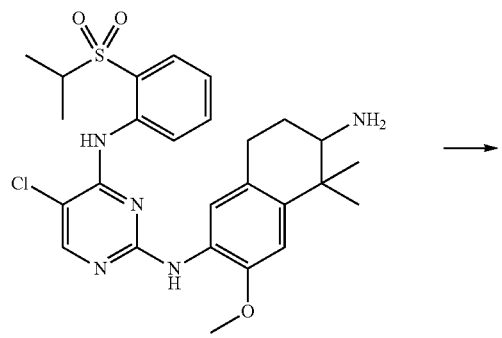
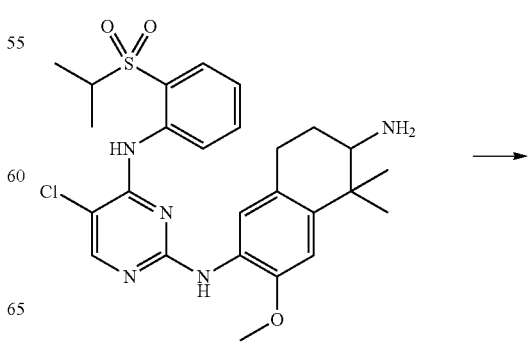

47

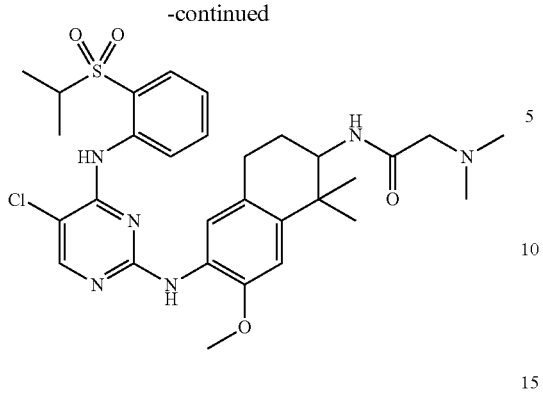

N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine (50 mg, 0.09 mmol) was dissolved in dichloromethane (1 mL), to which N,N-dimethyl glycine (14 mg, 0.14 mmol), 1-ethyl-3-(3-dimethylaminopropyl)carbodiimideI (22 mg, 0.14 mmol), 1-hydroxybenzotriazol (19 mg, 0.14 mmol), and triethylamine (0.02 mL, 0.14 mmol) were added, followed by stirring at room temperature. The reaction solution was diluted with dichloromethane, followed by washing with water and brine. The organic layer was dried over anhydrous magnesium sulfate to eliminate remaining moisture, followed by concentration. Then, purification was performed by silica gel column chromatography to give the target compound N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2-(dimethylamino)acetamide.

$^1$H NMR (300 MHz, CDCl$_3$) δ 9.51 (s, 1H), 8.54 (d, J=8.4, 1H), 8.15 (s, 1H), 7.93-7.92 (m, 1H), 7.66 (t, J=4.5, 1H), 7.55 (s, 1H), 7.28 (t, J=4.5, 1H), 7.13 (d, J=5.7, 1H), 6.80 (s, 1H), 4.18-4.15 (m, 1H), 3.89 (s, 3H), 3.26 (sept, J=6.9, 1H), 2.76-2.64 (m, 3H), 2.59 (s, 6H), 1.97-1.88 (m, 2H), 1.90-1.83 (m, 1H), 1.32 (d, J=1.2, 6H), 1.31 (d, J=1.2, 3H), 1.27 (s, 3H)

Example 28: Preparation of 5-chloro-N2-(6-(dimethylamino)-3-methoxy-5,5-dimethyl-5,6,7,8-tetrahydronaphthalene-2-yl)-N4-(2-(isopropylsulfonyl)phenyl)pyrimidine-2,4-diamine

48

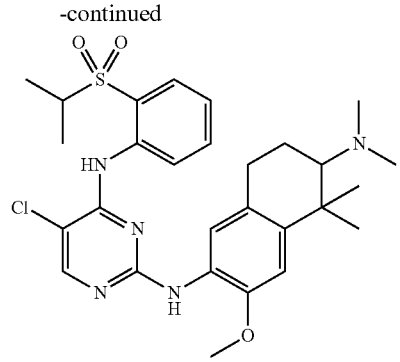

2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine (50 mg, 0.09 mmol) was dissolved in ethanol (1 mL), to which iodomethane (0.01 mL, 0.23 mmol) and N,N-diisopropylamine (0.04 mL, 0.23 mmol) were added, followed by stirring at room temperature. The reaction solution was diluted with dichloromethane, followed by washing with water and brine. The organic layer was dried over anhydrous magnesium sulfate to eliminate remaining moisture, followed by concentration. Then, purification was performed by silica gel column chromatography to give the target compound 5-chloro-N$^2$-(6-(dimethylamino)-3-methoxy-5,5-dimethyl-5,6,7,8-tetrahydronaphthalene-2-yl)-N$^4$-(2-(isopropylsulfonyl)phenyl)pyrimidine-2,4-diamine.

$^1$H NMR (300 MHz, CDCl$_3$) δ 9.53 (s, 1H), 8.57 (d, J=8.4, 1H), 8.18 (s, 1H), 7.95-7.94 (m, 2H), 7.66 (t, J=4.5, 1H), 7.57 (s, 1H), 7.28 (t, J=4.5, 1H), 6.82 (s, 1H), 4.21-4.17 (m, 1H), 3.91 (s, 3H), 3.26 (sept, J=6.9, 1H), 2.80-2.75 (m, 1H), 2.67-2.64 (m, 1H), 2.38 (s, 6H), 1.98-1.92 (m, 1H), 1.90-1.86 (m, 1H), 1.35 (d, J=2.7, 3H), 1.33 (d, J=1.2, 3H), 1.28 (s, 6H)

Example 29: Preparation of N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)formimideamide

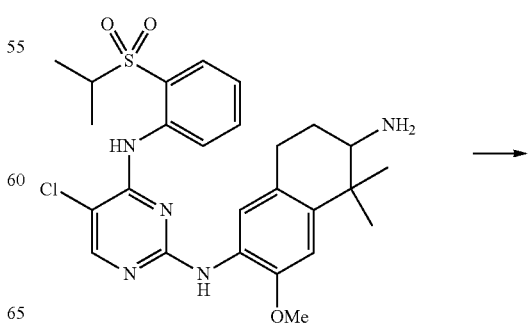

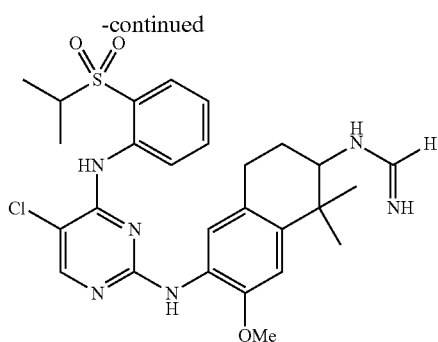

Ethylformimidate hydrochloride (7 mg, 0.056 mmol) was dissolved in N,N-dimethylformamide (0.5 mL), to which diisopropylamine (10 μL, 0.56 mmol), followed by stirring at 10 minutes. Then, N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine (25 mg, 0.047 mmol) was added thereto, followed by stirring at room temperature for 1 hour. Upon completion of the reaction, the reaction mixture was concentrated, extracted with ethylacetate (10 mL) and water (5 mL), dried over Na₂SO₄, filtered, and concentrated again. Then, purification was performed by silica gel column chromatography to give the target compound (4.5 mg, 17%).

$^1$H NMR (300 MHz, CdCl₃) δ 9.55 (s, 1H), 8.55 (d, J=9.0 Hz, 1H), 8.16 (s, 1H), 7.95 (m, 2H), 7.81 (m, 1H), 7.73 (m, 1H), 7.54 (s, 1H), 7.26 (m, 1H), 6.78 (s, 1H), 3.91 (s, 3H), 3.42 (m, 1H), 3.30 (m, 1H), 2.81 (m, 2H), 2.06 (m, 3H), 1.34 (m, 12H); LC/MS (M+1) calculated for C27H33ClN6O3S 557.1, found 558.1.

Example 30: Preparation of N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)acetimideamide

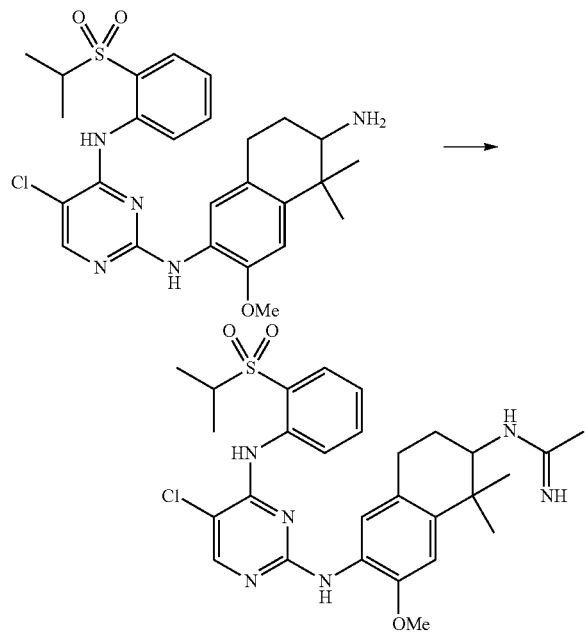

Ethylacetimidate hydrochloride (10 mg, 0.081 mmol) was dissolved in N,N-dimethylformamide (2 mL), to which diisopropylamine (20 μL, 0.114 mmol) was added, followed by stirring for 10 minutes. Then, N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine (30 mg, 0.057 mmol) was added thereto, followed by stirring at room temperature for 1 hour. Upon completion of the reaction, the reaction mixture was concentrated, extracted with ethylacetate (10 mL) and water (5 mL), dried over Na₂SO₄, filtered, and concentrated again. Then, purification was performed by silica gel column chromatography to give the target compound (8 mg, 25%).

$^1$H NMR (300 MHz, CdCl₃) δ 9.90 (s, 1H), 9.56 (s, 1H), 8.55 (m, 1H), 8.18 (s, 1H), 7.95 (m, 2H), 7.74 (m, 1H), 7.55 (m, 1H), 7.26 (m, 1H), 6.80 (s, 1H), 3.92 (s, 3H), 3.54 (m, 1H), 3.28 (m, 1H), 3.05 (m, 1H), 2.80 (m, 1H), 2.37 (s, 3H), 2.06 (m, 1H), 1.34 (m, 12H); LC/MS (M+1) calculated for C28H35ClN9O3S 571.4, found 572.4.

Example 31: Preparation of N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)guanidine

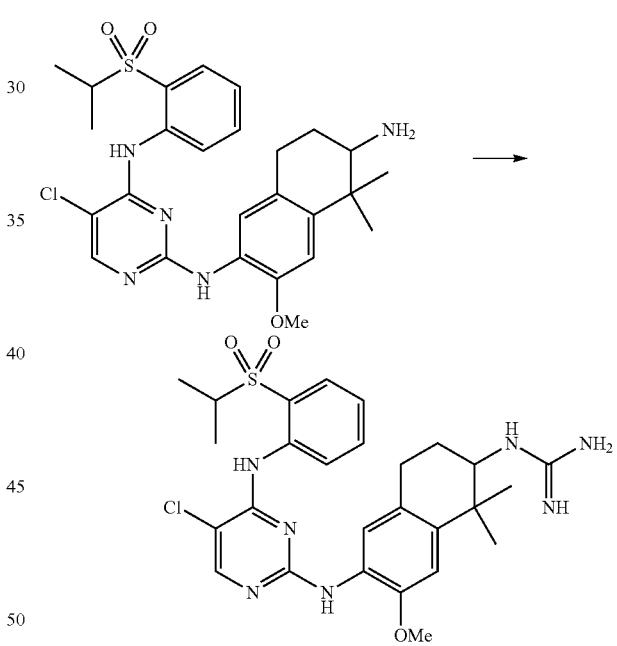

N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine (0.050 g, 0.094 mmol) was dissolved in dimethylform amide (1 ml), to which pyrazole carboxamide hydrochloride (0.020 g, 0.14 mmol) and diaisopropylethylamine (0.024 ml, 0.14 mmol) were added, followed by stirring at room temperature. Upon completion of the reaction, the reaction mixture was concentrated under reduced pressure, diluted with ethylacetate, and washed with water. The organic layer was dried over anhydrous magnesium sulfate, and filtered. Then, purification was performed by silica gel column chromatography to give the target compound (0.025 g, 47%).

$^1$H NMR (CDCl₃, 300 MHz) δ 9.54 (s, 1H), 8.54 (d, J=9 Hz, 1H), 7.99 (s, 1H), 7.80-7.68 (m, 3H), 7.54 (m, 1H), 7.28

(s, 1H), 7.22 (m, 1H), 6.73 (s, 1H), 3.85 (s, 3H), 3.64 (br s, 1H), 3.26-3.19 (m, 1H), 2.88-2.86 (m, 1H), 2.74 (m, 1H), 2.04-1.96 (m, 2H), 1.52-1.2 (m, 12H); LC/MS (ESI) m/z 572.2 [M+H]$^+$

The chemical formulae of the compounds prepared in examples 1~31 are shown in Table 1.

TABLE 1

| Example | Structure |
|---|---|
| 1 | 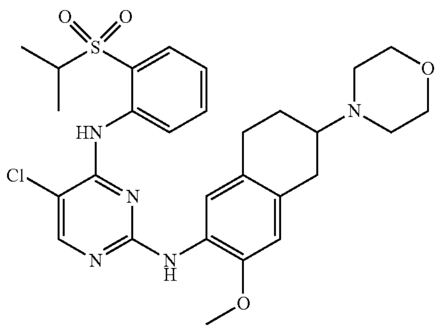 [SMILES: COc1cc2c(cc1Nc1ncc(Cl)c(Nc3ccccc3S(=O)(=O)C(C)C)n1)CCC(N1CCOCC1)C2] |
| 2 | 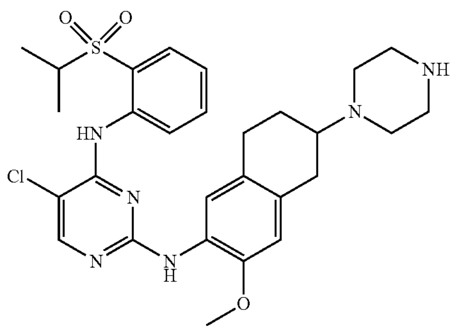 [SMILES: COc1cc2c(cc1Nc1ncc(Cl)c(Nc3ccccc3S(=O)(=O)C(C)C)n1)CCC(N1CCNCC1)C2] |
| 3 | 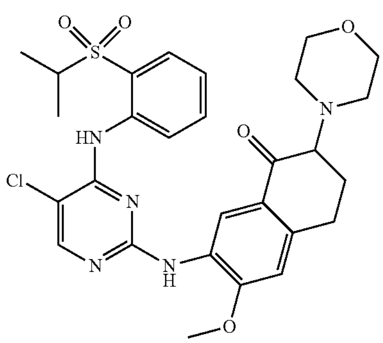 [SMILES: COc1cc2c(cc1Nc1ncc(Cl)c(Nc3ccccc3S(=O)(=O)C(C)C)n1)C(=O)C(N1CCOCC1)CC2] |
| 4 | 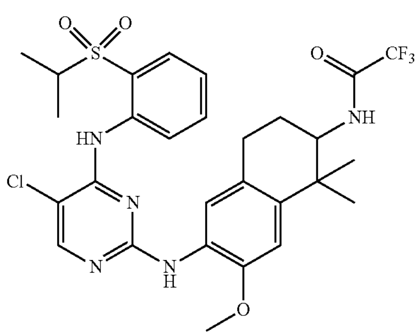 [SMILES: COc1cc2c(cc1Nc1ncc(Cl)c(Nc3ccccc3S(=O)(=O)C(C)C)n1)CCC(NC(=O)C(F)(F)F)C2(C)C] |
| 5 | |
| 6 | |
| 7 | |
| 8 | |

TABLE 1-continued

| Example | Structure |
|---------|-----------|
| 9 | 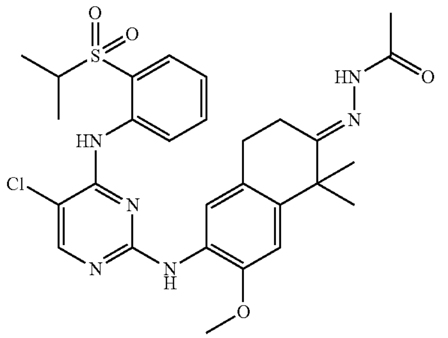 [SMILES: COc1cc2c(cc1Nc1ncc(Cl)c(Nc3ccccc3S(=O)(=O)C(C)C)n1)CC/C(=N\NC(C)=O)C2(C)C] |
| 10 | 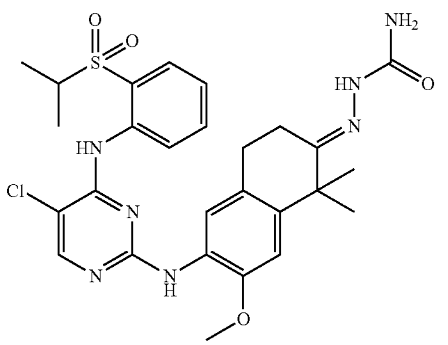 [SMILES: COc1cc2c(cc1Nc1ncc(Cl)c(Nc3ccccc3S(=O)(=O)C(C)C)n1)CC/C(=N\NC(N)=O)C2(C)C] |
| 11 | 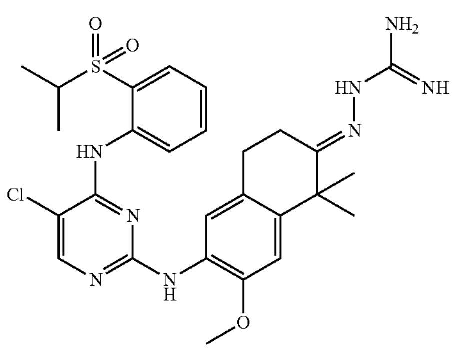 [SMILES: COc1cc2c(cc1Nc1ncc(Cl)c(Nc3ccccc3S(=O)(=O)C(C)C)n1)CC/C(=N\NC(=N)N)C2(C)C] |
| 12 | 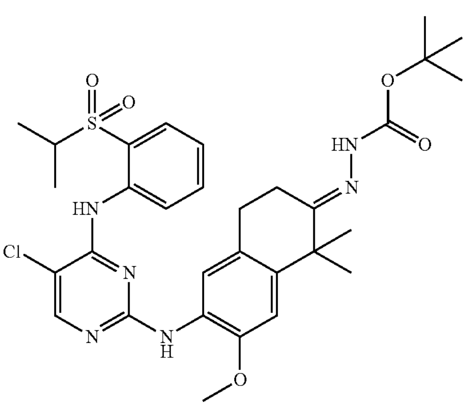 [SMILES: COc1cc2c(cc1Nc1ncc(Cl)c(Nc3ccccc3S(=O)(=O)C(C)C)n1)CC/C(=N\NC(=O)OC(C)(C)C)C2(C)C] |
| 13 | |
| 14 | |
| 15 | |
| 16 | |

TABLE 1-continued
| Example | Structure |
|---------|-----------|
| 17 | 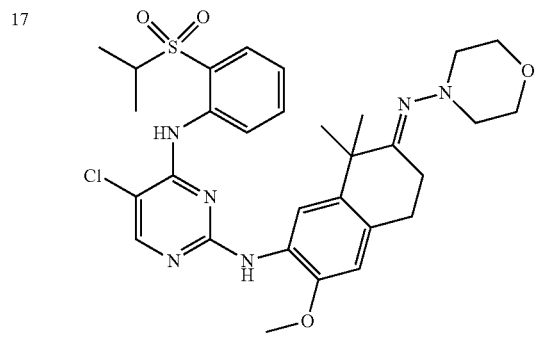 |
| 18 | 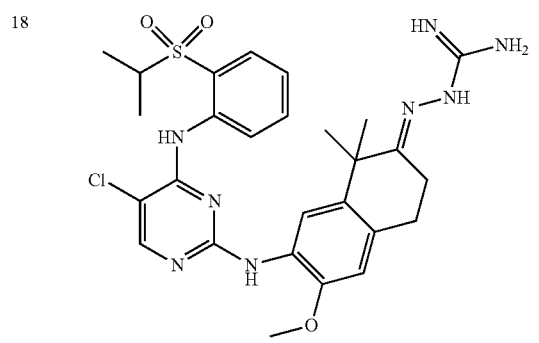 |
| 19 | 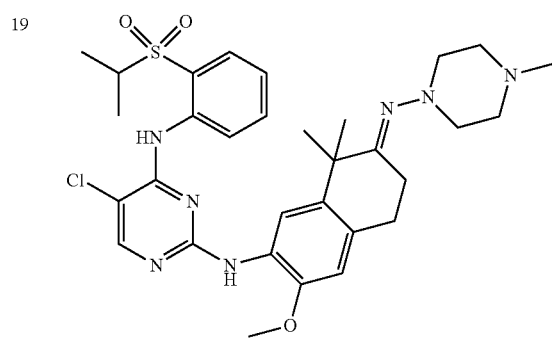 |
| 20 | 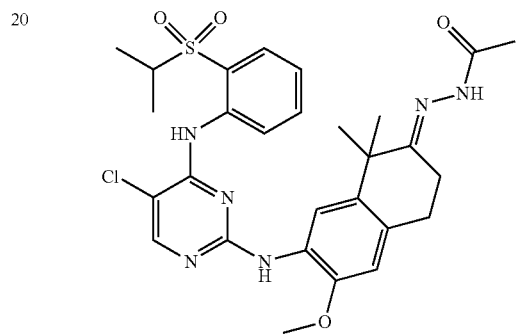 |
| 21 | 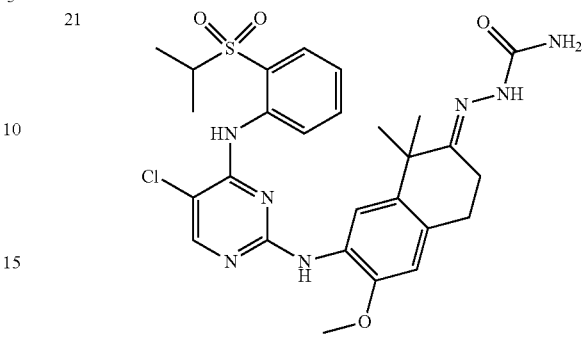 |
| 22 | 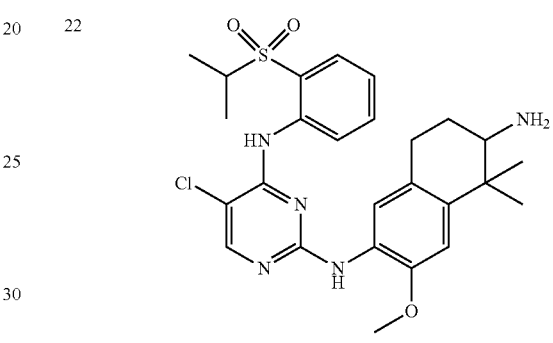 |
| 23 | 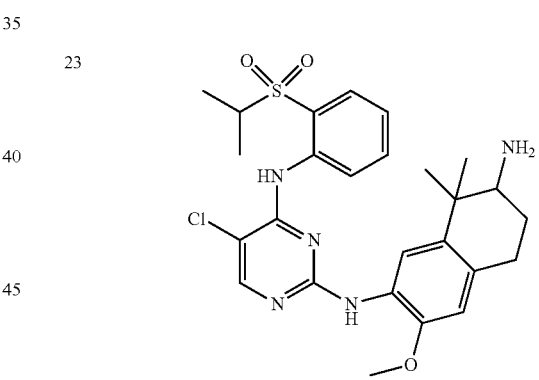 |
| 24 | 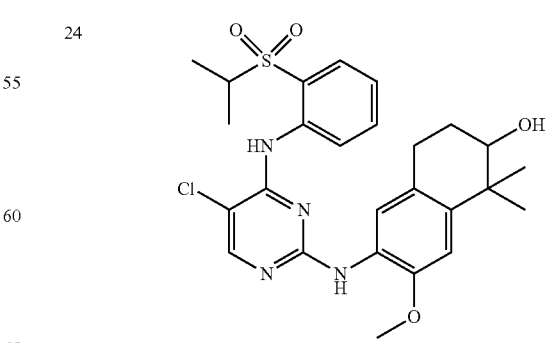 |

TABLE 1-continued

| Example | Structure |
|---|---|
| 25 | 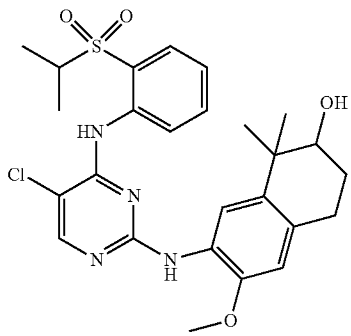 [SMILES: COc1cc2c(cc1Nc1ncc(Cl)c(Nc3ccccc3S(=O)(=O)C(C)C)n1)C(C)(C)C(O)CC2] |
| 26 | 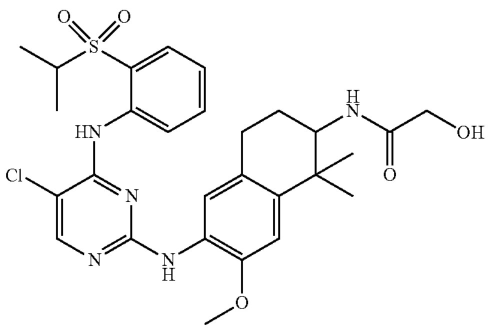 [SMILES: COc1cc2c(cc1Nc1ncc(Cl)c(Nc3ccccc3S(=O)(=O)C(C)C)n1)CCC(NC(=O)CO)C2(C)C] |
| 27 | 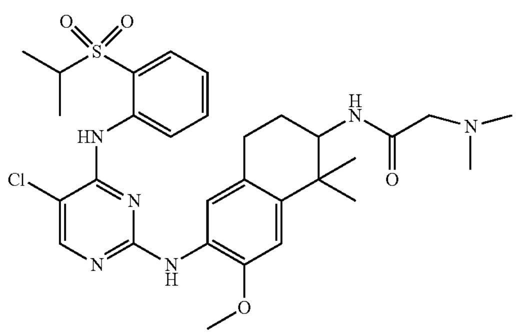 [SMILES: COc1cc2c(cc1Nc1ncc(Cl)c(Nc3ccccc3S(=O)(=O)C(C)C)n1)CCC(NC(=O)CN(C)C)C2(C)C] |
| 28 | 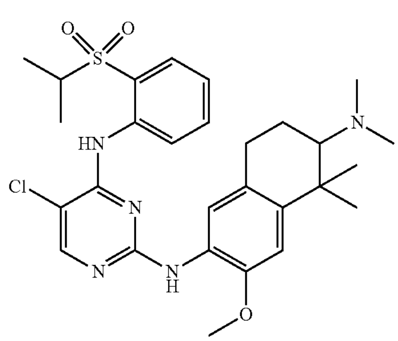 [SMILES: COc1cc2c(cc1Nc1ncc(Cl)c(Nc3ccccc3S(=O)(=O)C(C)C)n1)CCC(N(C)C)C2(C)C] |
| 29 | 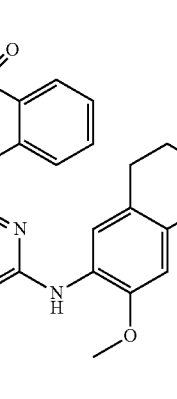 |
| 30 | |
| 31 | |

Experimental Example 1: Evaluation of Anaplastic Lymphoma Kinase Inhibitory Activity The following experiment was performed in order to measure the activity of the 4-(2-amino-tetrahydronaphthaleneyl)pyrimidine derivative represented by formula 1 of the present invention to inhibit anaplastic lymphoma kinase (ALK) activity.

To measure the activity to inhibit ALK, each of the compounds of the invention was loaded in a 96 well round bottom plate at the concentration of 1230 μM. Then, each of the compounds was mixed with ALK enzyme (1 μl) and biotin conjugated peptide substrate (2 μl), followed by culture for 15 minutes. ATP solution (5 μl) was added thereto, followed by kinase reaction at room temperature for 30 minutes. Streptavidin conjugated XL 665 (5 μl) dissolved in ethylenediaminetetraacetic acid solution and europium ($Eu^{3+}$) conjugated anti-phosphotyrosine antibody (5 μl) were added to the reaction solution to terminate the reaction. Upon completion of the reaction, one hour culture was performed, followed by analysis using homogeneous time-resolved fluorescence (HTRF, Cisbio). $OD_{615/665}$ was measured with Wallac Envision 2103. $IC_{50}$ of each compound was determined by using prism software (Version 5.01, Graphpad).

When the ALK activity was reduced up to 50%, it was considered the inhibitory activity was confirmed. So, $IC_{50}$ of each compound was presented in Table 2. At this time, in Table 2, when the inhibitory activity was observed at the concentration over 0.1 M, it was indicated as '+', and when the inhibitory activity was observed at the concentration range of 0.1~0.01 M, it was indicated as '++', and also when the inhibitory activity was observed at the concentration under 0.01 M, it was indicated as '+++'.

As shown in table 2, the compounds of the present invention displayed excellent anaplastic lymphoma kinase (ALK) inhibitory activity. Particularly, the compounds prepared in examples 1, 2, 14, 21, 22, 26, 27, and 28 exhibited excellent anaplastic lymphoma kinase (ALK) inhibitory activity at the concentration of 0.01 μM or less.

Therefore, the 4-(2-amino-tetrahydronaphthaleneyl)pyrimidine derivative represented by formula 1 of the present invention was confirmed to significantly inhibit the ALK activity, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 2: Evaluation of Anaplastic Lymphoma Kinase Inhibitory Activity in ALK L1196M To measure the activity of the 4-(2-amino-tetrahydronaphthaleneyl)pyrimidine derivative represented by formula 1 of the present invention to inhibit anaplastic lymphoma kinase (ALK) activity in ALK L1196M, the following experiment was performed.

Particularly, 4,000 ALK L1196M cells containing ALK enzyme were distributed in each well of a 96 well plate together with 100 μl of DMEM (Dulbecco's Modified Eagle's Medium). One day later, the compound of the present invention was added to each well at different concentrations of 10 μM, 2 μM, 0.4 μM, 0.08 μM, 0.0016 μM, and 0.00032 μM. DMSO (dimethylsulfoxide) was added to the well that was not loaded with the compound by the same amount as the compound. Three days after the addition of the compound, DMEM was eliminated. 10% TCA (trichloroacetic acid) was added to fix the cells. The wells were washed with running water three times and the live cells were stained with SRB solution (1× sulphorodamine B). Then, OD was measured to calculate the population of the live cells. $IC_{50}$ of the experimental compound used in the experiment above was calculated by using prism software (Version 5.01, Graphpad). When the activity of ALK L1196M containing ALK enzyme was reduced under 50%, it was considered that the compound demonstrated the inhibitory activity. $IC_{50}$ values of the compound are shown in Table 2 below.

Table 2 presents the ALK inhibitory activity of the compounds of the examples of the present invention in ALK L1196M containing ALK enzyme. When the inhibitory activity was observed at the concentration more than 0.1 M, it was indicated as '+', when the inhibitory activity was observed at the concentration range between 0.1 and 0.01 M, it was indicated as "++', and when the inhibitory activity was observed at the concentration under 0.01 M, it was indicated as "+++".

As shown in Table 2, the compounds prepared in examples of the present invention were confirmed to have ALK inhibitory activity in ALK L 1196M containing ALK enzyme. In particular, the compounds prepared in examples 2, 14, 22, 26, 27, and 28 demonstrated excellent ALK inhibitory activity in ALK L 1196M containing ALK enzyme at the concentration of 0.01 μM or less.

Therefore, the 4-(2-amino-tetrahydronaphthaleneyl)pyrimidine derivative represented by formula 1 of the present invention was confirmed to significantly inhibit the ALK activity, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 3: Evaluation of Anaplastic Lymphoma Kinase Inhibitory Activity in H3122

To measure the ALK inhibitory inhibiting activity of the 4-(2-amino-tetrahydronaphthaleneyl)pyrimidine derivative represented by formula 1 of the present invention in H3122, the non-small cell lung cancer cell line, the following experiment was performed by the same manner as described in experimental example 2 except that H3122 was used instead of ALK L1196M and the results are shown in Table 2.

Table 2 presents the ALK inhibitory activity of the compounds of the examples of the present invention in H3122 containing ALK enzyme. When the inhibitory activity was observed at the concentration more than 0.1 M, it was indicated as '+', when the inhibitory activity was observed at the concentration range between 0.1 and 0.01 M, it was indicated as "++', and when the inhibitory activity was observed at the concentration under 0.01 M, it was indicated as "+++".

As shown in Table 2, the compounds prepared in examples of the present invention were confirmed to have ALK inhibitory activity in H3122 containing ALK enzyme. In particular, the compounds prepared in examples 1, 2, 5, 13, 14, 15, 22, 24, 26, 27, and 28 demonstrated excellent ALK inhibitory activity in H3122 containing ALK enzyme at the concentration range between 0.01 and 0.1 μM.

Therefore, the 4-(2-amino-tetrahydronaphthaleneyl)pyrimidine derivative represented by formula 1 of the present invention was confirmed to significantly inhibit the ALK activity in H3122, the non-small cell lung cancer cell line, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

Experimental Example 4: Evaluation of Anaplastic Lymphoma Kinase Inhibitory Activity in Ba/F3 EML4-ALK L1196M To measure the ALK inhibitory inhibiting activity of the 4-(2-amino-tetrahydronaphthaleneyl)pyrimidine derivative represented by formula 1 of the present invention in Ba/F3 EML4-ALK L1196M, the following experiment was performed by the same manner as described in experimental example 2 except that Ba/F3 EML4-ALK L1196M was used instead of ALK L1196M and the results are shown in Table 2.

Table 2 presents the ALK inhibitory activity of the compounds of the examples of the present invention in Ba/F3 EML4-ALK L1196M containing ALK enzyme. When the inhibitory activity was observed at the concentration more than 0.1 M, it was indicated as '+', when the inhibitory activity was observed at the concentration range between 0.1 and 0.01 M, it was indicated as "++', and when the inhibitory activity was observed at the concentration under 0.01 M, it was indicated as "+++".

As shown in Table 2, the compounds prepared in examples of the present invention were confirmed to have ALK inhibitory activity in Ba/F3 EML4-ALK L1196M. In particular, the compounds prepared in examples 1, 2, 14, 22, 26, 27, and 28 demonstrated excellent ALK inhibitory activity in Ba/F3 EML4-ALK L1196M at the concentration range between 0.01 and 0.1 μM.

Therefore, the 4-(2-amino-tetrahydronaphthaleneyl)pyrimidine derivative represented by formula 1 of the present invention was confirmed to significantly inhibit the ALK activity in Ba/F3 EML4-ALK L1196M, so that it can be effectively used as a pharmaceutical composition for the prevention or treatment of such cancers as non-small cell lung cancer, neuroblastoma, inflammatory myeloid fibroblastic tumor, rhabdomysarcoma, myofibroblastoma, breast cancer, stomach cancer, lung cancer, and melanoma.

TABLE 2

| Example | ALK | ALK L1196M | Non-small cell lung cancer cell line H3122 | Ba/F3 EML4-ALK L1196M |
|---|---|---|---|---|
| 1 | +++ | ++ | ++ | ++ |
| 2 | +++ | +++ | ++ | ++ |
| 3 | ++ | + | + | + |
| 4 | + | + | + | + |
| 5 | ++ | + | ++ | + |
| 6 | + | + | + | + |
| 7 | + | + | + | + |
| 8 | + |   | + | + |
| 9 | ++ | ++ | + | + |
| 10 | ++ | ++ | + | + |
| 11 | ++ | ++ | + | + |
| 12 | + |   | + | + |
| 13 | ++ | ++ | ++ | + |
| 14 | +++ | +++ | ++ | ++ |
| 15 | ++ | ++ | ++ | + |
| 16 | + | + | + | + |
| 17 | + | + | + | + |
| 18 | ++ | ++ | + | + |
| 19 | ++ | + | + | + |
| 20 | ++ | + | + | + |
| 21 | +++ | ++ | + | + |
| 22 | +++ | +++ | ++ | ++ |
| 23 | ++ | ++ | + | + |
| 24 | ++ | ++ | ++ | + |
| 25 | ++ | ++ | + | + |
| 26 | +++ | +++ | ++ | ++ |
| 27 | +++ | +++ | ++ | ++ |
| 28 | +++ | +++ | ++ | ++ |
| 29 |   | +++ | ++ | + |
| 30 |   | +++ | ++ | + |
| 31 |   | +++ | + | + |

+: >0.1 μM (IC$_{50}$);
++: 0.1-0.01 μM (IC$_{50}$); and
+++: <0.01 μM (IC$_{50}$).

Experimental Example 5: In Vivo Xenograft Evaluation for H3122 Induced Lung Cancer <5-1> Experiment Preparation The nude mice (BALB/c nu/nu, female) used in this experiment were purchased from Charles River Japan, Inc. and raised and tested under SPF (Specific Pathogen Free) control. The human non-small cell lung cancer cell line H3122 maintained by Korea Research Institute of Chemical Technology was used in this experiment.

<5-2> Experiment Method

The female nude mice adapted to the laboratory were implanted with cancer. Particularly, H3122 cells grown to the appropriate size for passage were cut into 3×3×3 mm$^3$, which was transplanted (s.c.) under the right side of the nude mouse. When the size of the implanted cancer reached about 200 mm$^3$, administration of the compound of example 58 was started; this was the first day (day 1). For the control, 20% PEG 400+3% Tween 80 in DDW was orally administered. For the experimental group (7 mice/group), the compound was dissolved in the same solvent of the control, which was orally administered 14 times in total (q.d.×14). The size of the cancer was measured every 2~3 days after the administration using a caliper and the diameters (long diameter (a), short diameter (b)) of the cancer were measured. The size of the cancer (volume, V) was calculated according to mathematical formula 1.

$$\text{Volume (mm}^3\text{)}=a \times b^2/2 \qquad \text{[Mathematical Formula 1]}$$

In the mathematical formula 1, a represents the horizontal length of the cancer; and b represents the vertical short length of the cancer.

The results are shown in FIGS. 1 and 2.

FIG. 1 is a graph showing the results of observing the size of cancer in the control group (CONTROL), the LDK378-treated group, and the group treated with the compound of example 14 over the time.

FIG. 2 is a graph showing the results of observing the size of cancer in the control group (CONTROL), the LDK378-treated group, and the group treated with the compound of example 22 over the time.

As shown in FIGS. 1 and 2, the cancer size was significantly increased in the control group not treated with LDK378 or the compound of the invention. In the meantime, when the compound of example 14 or example 22 of the present invention was treated, the effect of inhibiting cancer size was excellent, similar to LDK378.

Manufacturing Example 1: Preparation of Powders

| Compound of formula 1 | 2 g |
|---|---|
| Lactose | 1 g |

Powders were prepared by mixing all the above components, which were filled in airtight packs according to the conventional method for preparing powders.

Manufacturing Example 2: Preparation of Tablets

| Compound of formula 1 | 100 g |
|---|---|
| Corn starch | 100 g |
| Lactose | 100 g |
| Magnesium stearate | 2 mg |

Tablets were prepared by mixing all the above components by the conventional method for preparing tablets.

Manufacturing Example 3: Preparation of Capsules

| | |
|---|---|
| Compound of formula 1 | 100 g |
| Corn starch | 100 g |
| Lactose | 100 g |
| Magnesium stearate | 2 mg |

Capsules were prepared by mixing all the above components, which were filled in gelatin capsules according to the conventional method for preparing capsules.

Manufacturing Example 4: Preparation of Injectable Solution

| | |
|---|---|
| Compound of formula 1 | 500 g |
| Mannitol | 180 g |
| $Na_2HPO_4 \cdot 2H_2O$ | 26 g |
| Distilled water | 2974 mg |

Injectable solutions were prepared by mixing all the above components according to the conventional method for preparing injectable solutions.

Manufacturing Example 5: Preparation of Health Functional Food

| | |
|---|---|
| Compound of formula 1 | 500 g |
| Vitamin complex | proper amount |
| Vitamin A acetate | 70 mg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinic acid amide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

Manufacturing Example 6: Preparation of Health Beverages

| | |
|---|---|
| Compound of formula 1 | 500 g |
| Citric acid | 1000 mg |
| Oligosaccharide | 100 mg |
| Maesil (Prunus mume) Extract | 2 mg |
| Taurine | 1 mg |
| Purified water | 900 ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

INDUSTRIAL APPLICABILITY

The 4-(2-amino-tetrahydronaphthaleneyl)pyrimidine derivative, the optical isomer thereof, or the pharmaceutically acceptable salt thereof of the present invention is very effective in suppressing anaplastic lymphoma kinase (ALK) activity and as a result it can improve the effectiveness of treatment on cancer cells having anaplastic lymphoma kinase (ALK) fusion proteins such as EML4-ALK and NPM-ALK, so that it can be effectively used as a pharmaceutical composition for preventing or treating cancer.

What is claimed is:

1. A compound represented by formula 1 or a pharmaceutically acceptable salt of the same:

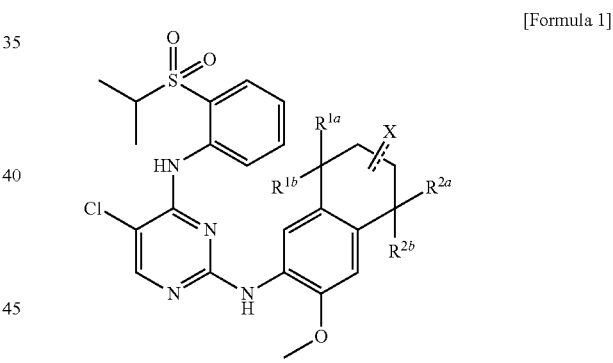

[Formula 1]

In the formula 1, $R^{1a}$, $R^{1b}$, $R^{2a}$ and $R^{2b}$ are independently hydrogen or $C_{1-5}$ straight or branched alkyl, and $R^{1a}$ and $R^{1b}$ or $R^{2a}$ and $R^{2b}$ can form oxo group (=O);

---- indicates either single bond or double bond;

when ---- is single bond,

X is —OH or —$NR^3R^4$, wherein, $R^3$ and $R^4$ are independently hydrogen, $C_{1-5}$ straight or branched alkyl, —(C=NH)—$R^5$, or —(C=O)$(CH_2)_nR^5$, wherein, $R^5$ is hydrogen, methyl, —OH, —$N(CH_3)_2$, —$NH_2$, or trihalomethyl, and n is an integer of 0-3, $R^3$ and $R^4$ can form 5-8 membered unsubstituted or substituted heterocycloalkyl containing one or more hetero atoms selected from the group consisting of N, O, and S along with the nitrogen atoms conjugated to the same;

when ---- is double bond,

X is =O, =N—OH or =N—$NR^6R^7$, wherein, $R^6$ and $R^7$ are independently hydrogen, $C_{1-5}$ straight or branched alkyl, —(C=O)R⁸ or —(C=NH)R⁸, wherein, R⁸ is methyl, —NH₂ or $C_{1-5}$ straight or branched alkoxy, R⁶ and R⁷ can form 5-8 membered unsubstituted or substituted heterocycloalkyl containing one or more hetero atoms selected from the group consisting of N, O, and S along with the nitrogen atoms conjugated to the same, and the substituted heterocycloalkyl can be substituted with —(C=O)CF₃ or $C_{1-5}$ straight or branched alkyl.

2. The compound represented by formula 1 or the pharmaceutically acceptable salt of the same according to claim 1, wherein:

$R^{1a}$, $R^{1b}$, $R^{2a}$ and $R^{2b}$ are independently hydrogen or $C_{1-3}$ straight or branched alkyl, and $R^{1a}$ and $R^{1b}$ can form oxo group (=O);

--- indicates either single bond or double bond;

when --- is single bond,

X is —OH or —NR³R⁴, wherein, R³ and R⁴ are independently hydrogen, $C_{1-3}$ straight or branched alkyl, —(C=NH)—R⁵, or —(C=O)(CH₂)ₙR⁵, wherein, R⁵ is hydrogen, methyl, —OH, —N(CH₃)₂, or —CF₃, and n is an integer of 0-1, R³ and R⁴ can form 6 membered unsubstituted or substituted heterocycloalkyl containing one or more hetero atoms selected from the group consisting of N and O along with the nitrogen atoms conjugated to the same, and the substituted heterocycloalkyl can be substituted with —(C=O)CF₃;

when --- is double bond,

X is =O, =N—OH or =N—NR⁶R⁷, wherein, R⁶ and R⁷ are independently hydrogen, $C_{1-3}$ straight or branched alkyl, —(C=O)R⁸ or —(C=NH)R⁸, wherein, R⁸ is methyl, —NH₂ or $C_{1-3}$ straight or branched alkoxy, R⁶ and R⁷ can form 6 membered unsubstituted or substituted heterocycloalkyl containing one or more hetero atoms selected from the group consisting of N and O along with the nitrogen atoms conjugated to the same, and the substituted heterocycloalkyl can be substituted with —(C=O)CF₃ or $C_{1-3}$ straight or branched alkyl.

3. The compound represented by formula 1 or the pharmaceutically acceptable salt of the same according to claim 1, wherein:

$R^{1a}$, $R^{1b}$, $R^{2a}$ and $R^{2b}$ are independently hydrogen or methyl, and $R^{1a}$ and $R^{1b}$ can form oxo group (=O);

--- indicates either single bond or double bond;

when --- is single bond,

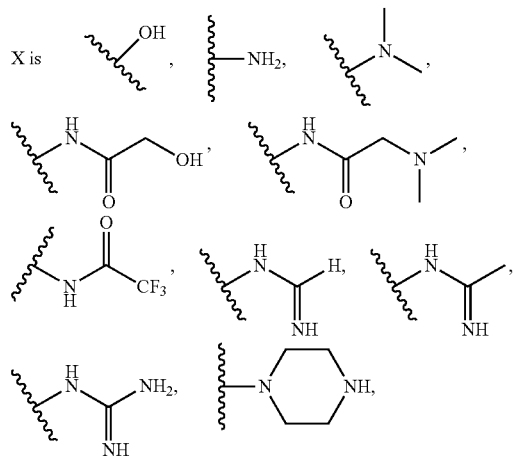

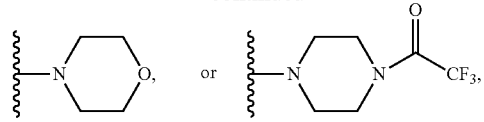

when --- is double bond,

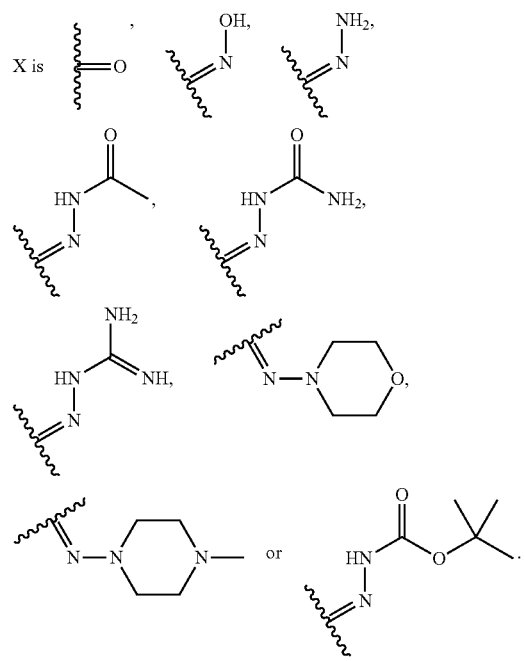

4. The compound represented by formula 1 or the pharmaceutically acceptable salt of the same according to claim 1, wherein the compound represented by formula 1 is selected from the group consisting of the following compounds:

(1) 5-chloro-N4-(2-(isopropylsulfonyl)phenyl)-N2-(3-methoxy-6-morpholino-5,6,7,8-tetrahydronaphthalene-2-yl)pyrimidine-2,4-diamine;

(2) 5-chloro-N4-(2-(isopropylsulfonyl)phenyl)-N2-(3-methoxy-6-(piperazine-1-yl)-5,6,7,8-tetrahydronaphthalene-2-yl)pyrimidine-2,4-diamine;

(3) 7-(5-chloro-4-(2-(isopropylsulfonyl)phenylamino)pyrimidine-2-ylamino)-6-methoxy-2-morpholino-3,4-dihydronaphthalene-1(2H)-one;

(4) N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2,2,2-trifluoroacetamide;

(5) 6-(5-chloro-4-(2-(isopropylsulfonyl)phenylamino)pyrimidine-2-ylamino)-7-methoxy-1,1-dimethyl-3,4-dihydronaphthalene-2(1H)-one;

(6) 7-(5-chloro-4-(2-(isopropylsulfonyl)phenylamino)pyrimidine-2-ylamino)-6-methoxy-1,1-dimethyl-3,4-dihydronaphthalene-2(1H)-one;

(7) N-(7-(5-chloro-4-(2-(isopropylsulfonyl)phenylamino)pyrimidine-2-ylamino)-6-methoxy-1,1-dimethyl-1,2,3,4-tetrahydronaphthalene-2-yl)-2,2,2-trifluoroacetamide;

(8) (E)-6-(5-chloro-4-(2-(isopropylsulfonyl)phenylamino)pyrimidine-2-ylamino)-7-methoxy-1,1-dimethyl-3,4-dihydronaphthalene-2(1H)-one oxime;

(9) (E)-N'-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)acetohydrazide;
(10) (E)-2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrazinecarboxamide;
(11) (E)-2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrazinecarboxamideamide;
(12) (E)-tert-butyl 2-(6-(5-chloro-4-(2-(isopropylsulfonyl)phenylamino)pyrimidine-2-ylamino)-7-methoxy-1,1-dimethyl-3,4-dihydronaphthalene-2(1H)-yladene)hydrazinecarboxylate;
(13) (E)-5-chloro-N2-(6-hydrazono-3-methoxy-5,5-dimethyl-5,6,7,8-tetrahydronaphthalene-2-yl)-N4-(2-(isopropylsulfonyl)phenyl)pyrimidine-2,4-diamine hydrochloride;
(14) (E)-5-chloro-N4-(2-(isopropylsulfonyl)phenyl)-N2-(3-methoxy-5,5-dimethyl-6-(4-methylpiperazine-1-ylimino)-5,6,7,8-tetrahydronaphthalene-2-yl)pyrimidine-2,4-diamine;
(15) (E)-5-chloro-N4-(2-(isopropylsulfonyl)phenyl)-N2-(3-methoxy-5,5-dimethyl-6-(morpholinoimino)-5,6,7,8-tetrahydronaphthalene-2-yl)pyrimidine-2,4-diamine;
(16) (E)-7-(5-chloro-4-(2-(isopropylsulfonyl)phenylamino)pyrimidine-2-ylamino)-6-methoxy-1,1-dimethyl-3,4-dihydronaphthalene-2(1H)-one oxime;
(17) (E)-5-chloro-N4-(2-(isopropylsulfonyl)phenyl)-N2-(3-methoxy-8,8-dimethyl-7-(morpholinoimino)-5,6,7,8-tetrahydronaphthalene-2-yl)pyrimidine-2,4-diamine;
(18) (E)-2-(7-(5-chloro-4-(2-(isopropylsulfonyl)phenylamino)pyrimidine-2-ylamino)-6-methoxy-1,1-dimethyl-3,4-dihydronaphthalene-2(1H)-yladene)hydrazinecarboxamideamide;
(19) (E)-5-chloro-N4-(2-(isopropylsulfonyl)phenyl)-N2-(3-methoxy-8,8-dimethyl-7-(4-methylpiperazine-1-ylimino)-5,6,7,8-tetrahydronaphthalene-2-yl)pyrimidine-2,4-diamine;
(20) (E)-N'-(7-(5-chloro-4-(2-(isopropyl sulfonyl)phenylamino)pyrimidine-2-ylamino)-6-methoxy-1,1-dimethyl-3,4-dihydronaphthalene-2(1H)-yladene)acetohydrazide;
(21) (E)-2-(7-(5-chloro-4-(2-(isopropylsulfonyl)phenylamino)pyrimidine-2-ylamino)-6-methoxy-1,1-dimethyl-3,4-dihydronaphthalene-2(1H)-yladene)hydrazinecarboxamide;
(22) N2-(6-amino-3-methoxy-5,5-dimethyl-5,6,7,8-tetrahydronaphthalene-2-yl)-5-chloro-N4-(2-(isopropylsulfonyl)phenyl)pyrimidine-2,4-diamine;
(23) N2-(7-amino-3-methoxy-8,8-dimethyl-5,6,7,8-tetrahydronaphthalene-2-yl)-5-chloro-N4-(2-(isopropylsulfonyl)phenyl)pyrimidine-2,4-diamine;
(24) 6-(5-chloro-4-(2-(isopropylsulfonyl)phenylamino)pyrimidine-2-ylamino)-7-methoxy-1,1-dimethyl-1,2,3,4-tetrahydronaphthalene-2-ol;
(25) 7-(5-chloro-4-(2-(isopropylsulfonyl)phenylamino)pyrimidine-2-ylamino)-6-methoxy-1,1-dimethyl-1,2,3,4-tetrahydronaphthalene-2-ol;
(26) N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2-hydroxyacetamide;
(27) N-(6-(5-chloro-4-(2-(isopropylsulfonyl)phenylamino)pyrimidine-2-ylamino)-7-methoxy-1,1-dimethyl-1,2,3,4-tetrahydronaphthalene-2-yl)-2-(dimethylamino)acetamide;
(28) 5-chloro-N2-(6-(dimethylamino)-3-methoxy-5,5-dimethyl-5,6,7,8-tetrahydronaphthalene-2-yl)-N4-(2-(isopropylsulfonyl)phenyl)pyrimidine-2,4-diamine;
(29) N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)formimideamide;
(30) N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)acetimideamide; and
(31) N-(6-((5-chloro-4-((2-(isopropylsulfonyl)phenyl)amino)pyridine-2-yl)amino)-7-methoxy-1,1-dimethyl-1,2,3,4-tetrahydronaphthalene-2yl)guanidine.

5. A method for preparing the compound represented by formula 1 of claim 1 containing the step of preparing the compound represented by formula 1 by reacting the compound represented by formula 2 with the compound represented by formula 3 as shown in reaction formula below.

[Reaction Formula 1]

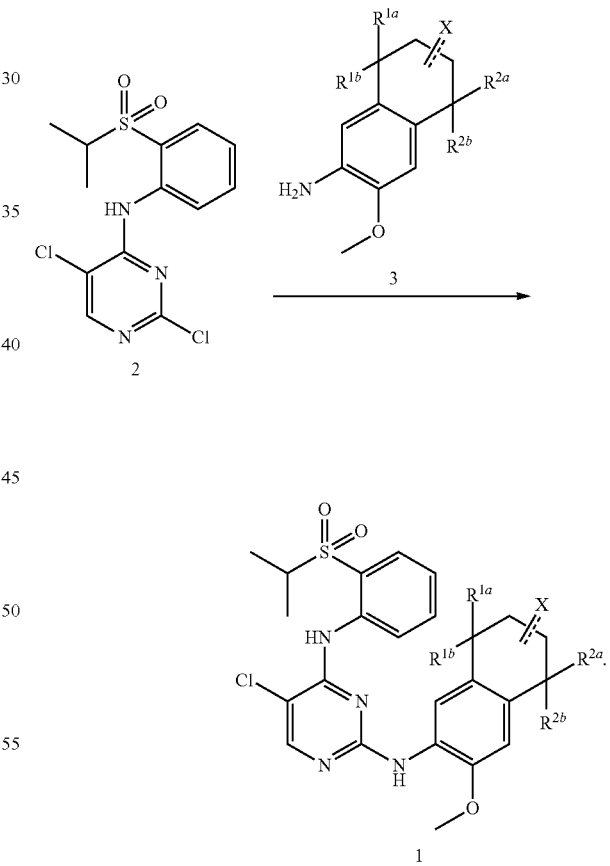

6. A method for preparing the compound represented by formula 1 of claim 1 containing the step of preparing the compound represented by formula 1b by hydrolyzing the ketone compound represented by formula 1a with the amine compound represented by formula 4 in the presence of an acid as shown in reaction formula 2 below:

[Reaction Formula 2]

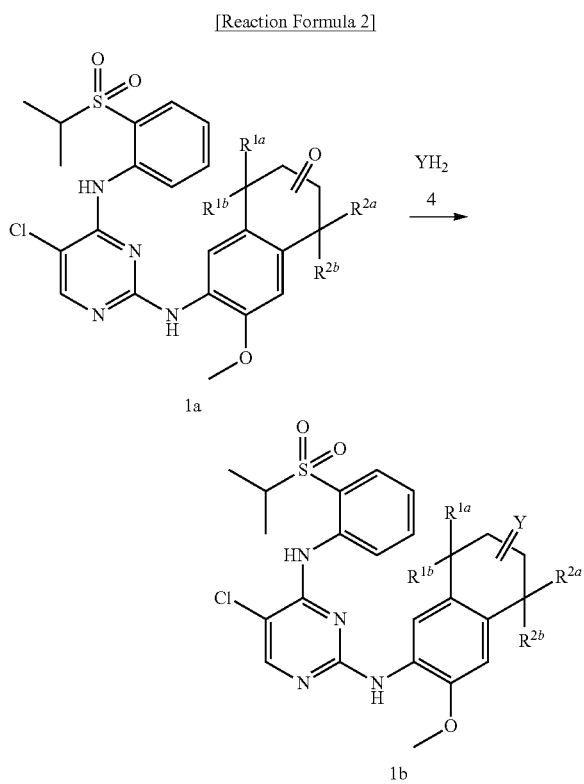

In the reaction formula 2,

Y is N—OH or N—NR$^6$R$^7$, wherein, R$^6$ and R$^7$ are independently hydrogen, C$_{1-5}$ straight or branched alkyl, —(C═O)R$^8$ or —(C═NH)R$^8$, wherein, R$^8$ is methyl, —NH$_2$ or C$_{1-5}$ straight or branched alkoxy, R$^6$ and R$^7$ can form 5-8 membered unsubstituted or substituted heterocycloalkyl containing one or more hetero atoms selected from the group consisting of N, O, and S along with the nitrogen atoms conjugated to the same, and the substituted heterocycloalkyl can be substituted with —(C═O)CF$_3$ or C$_{1-5}$ straight or branched alkyl; and The compound represented by formula 1a or formula 1b is any one of the compounds represented by Formula 1 of claim 1.

7. The method for preparing the compound represented by formula 1 of claim 1 according to claim 6, wherein the acid is at least one selected from the group consisting of acetic acid, trifluoroacetic acid, hydrochloric acid, sulfuric acid, and toluene sulfonic acid, either singly or in combination.

8. A pharmaceutical composition for the treatment of cancer comprising the compound represented by formula 1 or the pharmaceutically acceptable salt thereof of claim 1 as an active ingredient.

9. A method of treating non-small cell lung cancer comprising administering a pharmaceutically effective amount of the compound represented by formula 1 of claim 1 or the pharmaceutically acceptable salt thereof to a subject in need thereof.

* * * * *